US011439685B2

(12) United States Patent
Grinstaff et al.

(10) Patent No.: US 11,439,685 B2
(45) Date of Patent: Sep. 13, 2022

(54) FORMULATIONS FOR TREATING A FIBROTIC DISEASE

(71) Applicants: TRUSTEES OF BOSTON UNIVERSITY, Boston, MA (US); BETH ISRAEL DEACONESS MEDICAL CENTER, Boston, MA (US)

(72) Inventors: Mark W. Grinstaff, Brookline, MA (US); William Blessing, Boston, MA (US); Amanda Williamson, Boston, MA (US); Jack Kirsch, Boston, MA (US); Katherine Cook, Wheaton, IL (US); Ara Nazarian, Boston, MA (US); Edward K. Rodriguez, Boston, MA (US)

(73) Assignees: TRUSTEES OF BOSTON UNIVERSITY, Boston, MA (US); BETH ISRAEL DEACONESS MEDICAL CENTER, Boston, MA (US)

( * ) Notice: Subject to any disclaimer, the term of this patent is extended or adjusted under 35 U.S.C. 154(b) by 0 days.

(21) Appl. No.: 17/327,011

(22) Filed: May 21, 2021

(65) Prior Publication Data
US 2021/0361745 A1 Nov. 25, 2021

Related U.S. Application Data

(60) Provisional application No. 63/028,961, filed on May 22, 2020.

(51) Int. Cl.
*A61K 31/22* (2006.01)
*A61K 38/22* (2006.01)
(Continued)

(52) U.S. Cl.
CPC ........ *A61K 38/2221* (2013.01); *A61K 9/0024* (2013.01); *A61K 9/1635* (2013.01);
(Continued)

(58) Field of Classification Search
CPC .......................... A61K 38/2221; A61K 9/0024
See application file for complete search history.

(56) References Cited

U.S. PATENT DOCUMENTS 9,314,499 B2    4/2016  Wang et al.
2005/0244435 A1 11/2005 Shone et al.
(Continued)

FOREIGN PATENT DOCUMENTS

DE    102009008252 A1    8/2010
KR      100452752 B1    10/2004
(Continued)

OTHER PUBLICATIONS

Blessing et al., Intraarticular Injection of Relaxin-2 Alleviates Arthrofibrosis, Proceedings of National Academy of Sciences, 116(25):12183-12192. (Year: 2019).*
(Continued)

*Primary Examiner* — Carlos A Azpuru
(74) *Attorney, Agent, or Firm* — Nixon Peabody LLP; Ronald I. Eisenstein; Jeanne Jodoin

(57) ABSTRACT

The present invention provides formulations for the treatment of fibrotic diseases and disorders. In some embodiments, the formulation comprises a microparticle that includes an antifibrotic.

16 Claims, 13 Drawing Sheets
(13 of 13 Drawing Sheet(s) Filed in Color)
Specification includes a Sequence Listing.

(51) Int. Cl.
*A61K 9/16* (2006.01)
*A61K 9/00* (2006.01)
*A61P 19/02* (2006.01)
*A61P 19/04* (2006.01)

(52) U.S. Cl.
CPC ............ *A61K 9/1647* (2013.01); *A61P 19/02* (2018.01); *A61P 19/04* (2018.01)

(56) References Cited

U.S. PATENT DOCUMENTS

| | | |
|---|---|---|
| 2014/0140992 A1 | 5/2014 | Wong et al. |
| 2014/0205665 A1 | 7/2014 | Ross et al. |
| 2015/0038411 A1 | 2/2015 | Dschieizig |
| 2018/0133148 A1 | 5/2018 | Tellier et al. |
| 2019/0256570 A1 | 8/2019 | Dubowchik et al. |
| 2019/0282665 A1 | 9/2019 | Nazarian et al. |
| 2020/0046645 A1 | 2/2020 | Kim et al. |

FOREIGN PATENT DOCUMENTS

| | | |
|---|---|---|
| KR | 20070042598 A | 4/2007 |
| WO | 2008140477 A9 | 11/2008 |
| WO | 20170186073 A1 | 11/2017 |
| WO | 2018039318 A1 | 3/2018 |
| WO | 2018068047 A1 | 4/2018 |

OTHER PUBLICATIONS

Blessing et al. "Intraarticular injection of relaxin-2 alleviates shoulder arthrofibrosis." Proceedings of the National Academy of Sciences 116(25): 12183-12192 (2019).

Castellarin et al. "Manipulation and arthroscopy under general anesthesia and early rehabilitative treatment for frozen shoulders." Archives of Physical Medicine and Rehabilitation 85(8): 1236-1240 (2004).

Blessing. "The Anti-Fibrotic Properties of Relaxin-2 and its Novel Use for Treating Arthrofibrosis." Dissertation Defense. Boston University. Aug. 26, 2019, 103 pages.

Griggs et al. "Idiopathic adhesive capsulitis: a prospective functional outcome study of nonoperative treatment." The Journal of Bone and Joint Surgery-American vol. 82(10): 1398-1407 (2000).

Hand et al. "Long-term outcome of frozen shoulder." Journal of Shoulder and Elbow Surgery 17(2): 231-236 (2008).

Hsu et al. "Arthroscopic distension in the management of frozen shoulder." International Orthopaedics 15(2): 79-83 (1991).

Neviaser et al. "Adhesive capsulitis of the shoulder." JAAOS—Journal of the American Academy of Orthopaedic Surgeons 19(9): 536-542 (2011).

Parker et al. "Frozen Shoulder: Part II: Treatment by Manipulation Under Anesthesia." Orthopedics 12(7): 989-990 (1989).

Ryans et al. "A randomized controlled trial of intra-articular triamcinolone and/or physiotherapy in shoulder capsulitis." Rheumatology 44(4): 529-535 (2005).

Shaffer et al. "Frozen shoulder. A long-term follow-up." The Journal of Bone and Joint Surgery American vol. 74 (5): 738-746 (1992).

Arnau et al. "Current strategies for the use of affinity tags and tag removal for the purification of recombinant proteins." Protein Expression and Purification 48(1): 1-13 (2006).

Nilsson et al. "Affinity fusion strategies for detection, purification, and immobilization of recombinant proteins." Protein Expression and Purification 11(1): 1-16 (1997).

Poterski. "Synthesis of recombinant human relaxin H2 in bacteria and its effects on differentiation of carcinoembryonic stem cells." Diss. University of Guelph, 2017. 273 pages.

Xu et al. "[24] Fusions to self-splicing inteins for protein purification." Methods in Enzymology. vol. 326. Academic Press: 376-418 (2000).

\* cited by examiner

FORMULATIONS FOR TREATING A FIBROTIC DISEASE

CROSS-REFERENCE TO RELATED APPLICATIONS

This application claims benefit under 35 U.S.C. § 119(e) of U.S. Provisional Application No. 63/028,961 filed May 22, 2020, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 6, 2021, is named 701586-097700US-PT_SL.txt and is 22,186 bytes in size.

TECHNICAL FIELD

The technology described herein relates to methods and compositions for treating a fibrotic disease.

BACKGROUND

Joint stiffness is a significant public health issue with current treatment options providing varied and limited outcomes. Joint stiffness can affect any joint in the body, such as a shoulder joint, an elbow joint, a wrist joint, a finger joint, a hip joint, a knee joint, an ankle joint, a toe joint, the spine and the jaw A shoulder joint is often affected by joint stiffness, which is also termed a shoulder contracture, and is also known as "frozen shoulder".

Shoulder contracture is considered a self-limiting disease, but recovery is protracted and arduous, with a significant number of patients never regaining full ROM. The reported outcomes of conservative therapy (i.e., physical therapy) vary considerably and are highly dependent on how they are measured (Neviaser A. S. and Neviaser R. J., *J. Am. Acad. Orthop. Surg.* 2011, 19(9):536-42). Results tend to be more favorable with subjective outcome measures than with objective outcome measures. In one study, 90% of patients treated with minimal therapy reported satisfaction with their shoulder function (Griggs S. M. et al., *J. Bone Joint Surg. Am.* 2000, 82-A(10):1398-407). However, another that used objective outcomes reported residual pain in 50% of patients and motion deficit in 60% (Shaffer B. et al., *J. Bone Joint Surg. Am.* 1992; 74(5):738-46). Mild to moderate symptoms can persist after 4.4 years following symptom onset of shoulder contracture. For those experiencing severe disease, such functional impairment interferes with daily activities and work-related responsibilities (Hand C. et al., *Journal of Shoulder and Elbow Surgery* 2008, 17(2):231-6). When patients do not respond to conservative management, other treatment options are available. Operative intervention in the form of manipulation under anesthesia may restore motion and decrease pain, but it has been associated with complications such as fracture, tendon rupture, and neurologic injury (Castellarin G. et al., *Archives of Physical Medicine and Rehabilitation* 2004, 85(8):1236-40; Hsu S. Y. and Chan K. M., *International Orthopaedics,* 1991, 15(2):79-83; Parker R. D. et al., *Orthopedics,* 1989, 12(7):989-90). There are reports that manipulation or capsular release do not offer reliable and consistent results (Shaffer B. et al., *J. Bone Joint Surg. Am.* 1992, 74(5):738-46; Ryans I. et al., *Rheumatology* 2005, 44(4):529-35). Accordingly, a more effective and consistent therapy for joint stiffness is needed.

See also, PCT Application No US2017/055799; PCT Application No U.S. Ser. No. 14/380,163; and Disseration defense of William Blessing dated Aug. 26, 2019; the contents of which are incorporated herein by reference in their entireties.

SUMMARY

One aspect described herein provides a formulation comprising microparticles comprising an aliphatic polyester and an antifibrotic agent, wherein (i) said microparticles have a diameter of 1-100 m; (ii) the antifibrotic agent is relaxin and is present in an amount that is 0.01-33% of total mass; (iii) said aliphatic polyester is of molecular weight 10,000-200,000 Daltons; or (iv) the microparticles further comprise a vinyl polymer.

In one embodiment of any aspect herein, said antifibrotic agent is an agonist of the receptor RXFP1.

In one embodiment of any aspect herein, said antifibrotic agent is human relaxin-2 or an analog or variant.

In one embodiment of any aspect herein, the aliphatic polyester is poly-lactide-co-glycolide.

In one embodiment of any aspect herein, the aliphatic polyester is polycaprolactone.

In one embodiment of any aspect herein, said aliphatic polyester is terminated by an ester functional group, an alkyl-ester functional group, an amine functional group, an isocyanate functional group, an isothiocyanate functional group, a benzoyl fluoride functional group, a maleimide functional group, an iodoacetamide functional group, a 2-thiopyridine functional groups, a 3-arylpropiolonitrile functional group, a diazonium salt, an aldehyde, a ketone, an azide, an alkyne, a cyclooctyne, a phosphine or a carboxylic acid functional group.

In one embodiment of any aspect herein, said formulation comprises a vinyl polymer that is poly(vinyl alcohol) or poly(pyrrolidone).

In one embodiment of any aspect herein, said formulation comprises a vinyl polymer that is of molecular weight 10,000-200,000 Daltons.

In one embodiment of any aspect herein, the diameter of said microparticles is 1-75 µm; or 1-50 µm; or 5-50 µm; or 25-50 µm; or 30-50 µm; or 40-50 µm.

In one embodiment of any aspect herein, said aliphatic polyester is poly-lactide-co-glycolide with a molar ratio of 15:85-25:75, lactide:glycolide.

In one embodiment of any aspect herein, the formulation comprises the vinyl polymer in an amount of 0.01-1.0% of total mass.

In one embodiment of any aspect herein, said antifibrotic agent is 0.005-5% of the total formulation mass.

In one embodiment of any aspect herein, said antifibrotic agent is a relaxin.

In one embodiment of any aspect herein, said formulation comprises microparticles suspended in a liquid solution.

In one embodiment of any aspect herein, said formulation comprises microparticles suspended in a sodium chloride liquid solution or a sodium carboxymethylcellulose solution.

In one embodiment of any aspect herein, said formulation is a sustained release formulation.

In one embodiment of any aspect herein, said formulation is a sustained release formulation and wherein the antifibrotic agent is released over an extended period of time.

In one embodiment of any aspect herein, said formulation is a sustained release formulation wherein the antifibrotic agent is released over an extended period of least 1 day.

In one embodiment of any aspect herein, the formulation is formulated for administration via inhalation as an aerosol, administration via intra-articular injection or administration via intramuscular injection.

In one embodiment of any aspect herein, the formulation is administered to the subject such that the antifibrotic agent is administered to a subject at a dose between 1-2000 µg/kg body weight.

In some embodiment of any aspect herein, the formulation as provided herein is suspended in a liquid solution. In some embodiments the microparticle formulation is suspended in a liquid solution wherein the microparticle is about 0.0001-0.001% of the total solution; or is about 0.001-0.01% of the total solution; or about 0.01-0.05% of the total solution; or is about 0.05-0.1% of the total solution; or is about 0.1-1% of the total solution; or is about 1-10% of the total solution; or is about 10-20% of the total solution; or is about 20-30% of the total solution; or is about 30-50% of the total solution; or is about 50-75% of the total solution; or is about 75-90% of the total solution. In some embodiments the aforementioned percentages are by weight, in other embodiments, the aforementioned percentages are by volume.

In one embodiment of any aspect herein, the formulation comprises microparticles having an aliphatic polyester and an antifibrotic agent, wherein the microparticles have a diameter of 1-100 µm.

In one embodiment of any aspect herein, the formulation comprises microparticles having an aliphatic polyester and an antifibrotic agent, wherein the antifibrotic agent is relaxin and is present in an amount that is 0.01-33% of total mass.

In one embodiment of any aspect herein, the formulation comprises microparticles having an aliphatic polyester and an antifibrotic agent, wherein said aliphatic polyester is of molecular weight 10,000-200,000 daltons.

In one embodiment of any aspect herein, the formulation comprises microparticles having an aliphatic polyester, a vinyl polymer and an antifibrotic agent.

In one embodiment of any aspect herein, the formulation comprises microparticles having an aliphatic polyester, a vinyl polymer and an antifibrotic agent, wherein said microparticles have a diameter of 1-100 µm.

A method of treating a fibrotic disease, the method comprising administering to a subject in need thereof any formulation described herein.

A method, said method comprising identifying a subject diagnosed with one or more diseases selected from the group of diseases listed in Table 1 or Table 2 and administering any formulation described herein to the subject.

In one embodiment of any aspect herein, the disease is selected from the group consisting of Duchenne Muscular Dystrophy, Becker Muscular Dystrophy, Spinal Muscular Atrophy (Type I, II, III, or IV), Cerebral Palsy, Stroke, Traumatic Brain Injury, peripheral nerve injury, Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature, cellulite and interstitial lung disease.

In one embodiment of any aspect herein, said administering is via inhalation as an aerosol, via intra-articular injection, via peri-articular injection, via intramuscular injection, via perimuscular injection, via intradermal injection, via subcutaneous injection, via intracapsular injection, via pericapsular injection, via intraligamentous injection, via periligamentous injection, via intratendinous injection, via peritendinous injection, via intramusculotendionous injection, via perimusculotendinous injection, via intraosteotendinous injection, via periosteotendinous injection.

In one embodiment of any aspect herein, the disease is Duchene's muscular dystrophy and said administering is via intramuscular injection; the disease is Duchene's muscular dystrophyand said administering is via intraarticular injection; the disease is Becker's muscular dystrophy and said administering is via intramuscular injection; the disease is Becker's muscular dystrophy and said administering is via intraarticular injection; the disease is Spinal Muscular Dystrophy and said administering is via intramuscular injection; the disease is Spinal Muscular Dystrophy and said administering is via intraarticular injection; the disease is Arthrogryposis Multiplex Congenita and said administering is via intramuscular injection; the disease is Arthrogryposis Multiplex Congenita and said administering is via intraarticular injection; the disease is Cerebral Palsy and said administering is via intramuscular injection; the disease is Cerebral Palsy and said administering is via intraarticular injection; the disease is Stroke and said administering is via intramuscular injection; the disease is Stroke and said administering is via intraarticular injection; the disease is Traumatic Brain Injury and said administering is via intramuscular injection; the disease is Traumatic Brain Injury and said administering is via intraarticular injection; the disease is peripheral nerve injury and said administering is via intramuscular injection; the disease is peripheral nerve injury and said administering is via intraarticular injection.

In one embodiment of any aspect herein, microparticles are of sizes between 1 um-10 um and said administering is via inhalation as an aerosol; the microparticles are of sizes between 20 um-100 um and said administering is via intramuscular injection; the microparticles are of sizes between 5 um-50 um and said administering is via intraarticular injection.

In one embodiment of any aspect herein, the disease is interstitial lung disease, the diameter of the microparticle is 1-10 um, and said administering is via inhalation as an aerosol; the disease is Duchene's Muscular Dystrophy, the diameter of the microparticle is 10-30 um, and said administering is via intraarticular injection; the disease is Duchene's Muscular Dystrophy, the diameter of the microparticle is 25-50 um, and said administering is via intraarticular injection; the disease is Duchene's Muscular Dystrophy, the diameter of the microparticle is 10-30 um, and said administering is via intramuscular injection; the disease is Duchene's Muscular Dystrophy, the diameter of the microparticle is 25-50 um, and said administering is via intramuscular injection; the disease is Spinal Muscular Atrophy, the diameter of the microparticle is 10-30 um, and said administering is via intraarticular injection; the disease is Spinal Muscular Atrophy, the diameter of the microparticle is 25-50 um, and said administering is via intraarticular injection; the disease is Spinal Muscular Atrophy, the diameter of the microparticle is 10-30 um, and said administering is via intramuscular injection; the disease is Spinal Muscular Atrophy, the diameter of the microparticle is 25-50 um, and said administering is via intramuscular injection; the disease is joint arthrofibrosis, the diameter of the microparticle is 10-30 um, and said administering is via intraarticular injection; the disease is joint arthrofibrosis, the diameter of the microparticle is 25-50 um, and said administering is via intraarticular injection, the disease is joint Cerebral Palsy, the diameter of the microparticle is 10-30 um, and said administering is via intraarticular injection; the disease is joint Cerebral Palsy, the diameter of the microparticle is 25-50 um, and said administering is via intraarticular injection; the disease is joint Stroke, the diameter of the microparticle is 10-30 um, and said administering is via intraarticular injection; the disease is joint Stroke, the diameter of the microparticle is 25-50 um, and said administering is via intraarticular injection; the disease is Traumatic Brain Injury, the diameter of the microparticle is 10-30 um, and said administering is via intraarticular injection; the disease is Traumatic Brain Injury, the diameter of the microparticle is 25-50 um, and said administering is via intraarticular injection; the disease is peripheral nerve injury, the diameter of the microparticle is 10-30 um, and said administering is via intraarticular injection; the disease is peripheral nerve injury, the diameter of the microparticle is 25-50 um, and said administering is via intraarticular injection.

In one embodiment of any aspect herein, the formulation is administered to the subject such that the antifibrotic agent is administered to a subject at a dose between 1-2000 μg/kg body weight.

Definitions

For convenience, the meaning of some terms and phrases used in the invention, examples, and appended claims, are provided. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

As used herein, an "effective amount," is intended to include the amount of the agent e.g., relaxin or an analog, a fragment or a variant thereof, that, when administered to a subject via a depot having a stiffened joint, is sufficient to affect treatment of the stiffened joint (e.g., by diminishing, ameliorating or maintaining the stiffened joint or one or more symptoms of the stiffened joint). The "effective amount" may vary depending on the sequence of the agent, how the agent is administered, the severity of the joint stiffness and the history, age, weight, family history, genetic makeup, the types of preceding or concomitant treatments, if any, and other individual characteristics of the subject to be treated.

The term "effective amount," as used herein, is also intended to include the amount of agent e.g., relaxin or an analog, a fragment or a variant thereof, that, when administered to a subject in a depot with a stiffened joint, and either currently or not yet experiencing or displaying symptoms of the stiffened joint, such as pain on movement or restriction of the movement or range of movement of the joint affected by the joint stiffness, and/or a subject at risk of developing a stiffened joint, is sufficient to prevent or ameliorate the stiffened joint or one or more of its symptoms. Ameliorating the stiffened joint includes slowing the course of the progression of the joint stiffness or reducing the severity of later-developing joint stiffness.

As used herein, a "subject" is an animal, such as a mammal, including a primate (e.g., a human), a non-human primate, (e.g., a monkey and a chimpanzee), a non-primate (e.g., a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being assessed for a stiffened joint, a human at risk for developing a stiffened joint, a human having a stiffened joint, and/or a human being treated for a stiffened joint.

As used herein, the terms "treat," "treatment," "treating," or "amelioration" refer to therapeutic treatments, wherein the object is to reverse, alleviate, ameliorate, inhibit, slow down or stop the progression or severity of a condition, e.g., a condition associated with fibrosis, e.g. a fibrotic disease and disorder. The term "treating" includes reducing or alleviating at least one adverse effect or symptom of a fibrotic disease and disorder (e.g., inflammation, stiffening of a joint, contracture of a joint, contracture of a joint not caused by muscle contracture, contracture of a joint associated with muscle contracture, pain, loss of mobility, difficulty breathing, muscle stiffness, muscle dysfunction, skin dimpling, keloid scarring, burn-associated scarring). Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "prevention" or "preventing," when used in reference to a stiffened joint, refers to a reduction in the likelihood that a subject, e.g., a human subject, will develop a symptom associated with such a stiffened joint, or a reduction in the frequency and/or duration of a symptom associated with a stiffened joint. The likelihood of developing a stiffened joint is reduced, for example, when a subject having one or more risk factors for a stiffened joint either fails to develop a stiffened joint or develops a stiffened joint with less severity relative to a population having the same risk factors and not receiving treatment as described herein. The failure to develop a stiffened joint, or the reduction in the development of a symptom associated with stiffened joint (e.g., by at least about 10%), or the exhibition of delayed symptoms (e.g., delayed by days, weeks, months or years) is considered effective prevention.

As used herein, the term "administering," refers to the placement of a therapeutic (e.g., an microcapsule comprising an antifibrotic agent described herein) or composition as disclosed herein into a subject by a method or route which results in at least partial delivery of the agent to the subject. Compositions, e.g., pharmaceutical composition comprising agents as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., a disease or disorder associated with fibrosis. A subject can be male or female.

A subject can be one who has been previously diagnosed with or identified as suffering from or having a disease or disorder in need of treatment (e.g., a disease or disorder associated with fibrosis) or one or more complications related to such a disease or disorder, and optionally, have already undergone treatment for the disease or disorder or the one or more complications related to the disease or disorder. Alternatively, a subject can also be one who has not been previously diagnosed as having such disease or disorder (e.g., a disease or disorder associated with fibrosis) or related complications. For example, a subject can be one who exhibits one or more risk factors for the disease or disorder or one or more complications related to the disease or disorder or a subject who does not exhibit risk factors.

The term "microparticle" includes but is not limited to microsphere, microgranules, microsponges, or any non-spherical particles within the specified dimensions with an internal matrix capable of encapsulation of the agent e.g., relaxin.

The term "microparticle" refers to particles with a diameter that is preferably less than 500 um, and more preferably between 1 um and 50 um. Microparticles may also include nanoparticles. Nanoparticles refer to a particle having a diameter that is preferably less than 1 um and greater than 10 nm.

As used herein, an "agent" refers to e.g., a molecule, protein, peptide, antibody, or nucleic acid, that inhibits expression of a polypeptide or polynucleotide, or binds to, partially or totally blocks stimulation, decreases, prevents, delays activation, inactivates, desensitizes, or down regulates the activity of the polypeptide or the polynucleotide. Agents that inhibit SerpinB1, e.g., inhibit expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

Methods and compositions described herein comprise an antifibrotic agent, e.g., relaxin or functional variant thereof. As used herein, "Relaxin 2" refers to the gene encodes a member of the relaxin subfamily and insulin superfamily of peptide hormones. Sequences for relaxin 2, also known as H2; RLXH2; H2-RLX; bA12D24.1.1; and bA12D24.1.2, are known for a number of species, e.g., human relaxin 2 (NCBI Gene ID: 6019) polypeptide (e.g., NCBI Ref Seq NP_001316120.1) and mRNA (e.g., NCBI Ref Seq NM_001329191.2). Relaxin 2 can refer to human Relaxin 2, including naturally occurring variants, molecules, and alleles thereof. Relaxin 2 refers to the mammalian Relaxin 2 of, e.g., mouse, rat, rabbit, dog, cat, cow, horse, pig, and the like.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increase", "enhance", or "activate" are all used herein to mean an increase by a reproducible statistically significant amount. In some embodiments, the terms "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, a 20 fold increase, a 30 fold increase, a 40 fold increase, a 50 fold increase, a 6 fold increase, a 75 fold increase, a 100 fold increase, etc. or any increase between 2-fold and 10-fold or greater as compared to an appropriate control. In the context of a marker, an "increase" is a reproducible statistically significant increase in such level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a fibrotic disease or disorder, or a biological sample that has not been contacted with an agent disclosed herein).

As used herein, an "appropriate control" refers to an untreated, otherwise identical cell or population (e.g., a patient who was not administered an agent described herein, or was administered by only a subset of agents described herein, as compared to a non-control cell).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

As used herein the term "aliphatic polyester" refers to the following without limitation, poly(lactide), poly(glycolide), poly(lactide-co-glycolide), poly(γ-valerolactone), polyethylene glycol (PEG), alginate, agarose, poly(hydroxyvalerate), poly(hydroxybutyrate), poly(3-hydroxybutyrate-co-4-hydroxybutyrate), poly(hydroxyhexanoate), poly(butylene succinate), poly(alkylene alkanoate), poly(propylene succinate), poly(ethylene succinate), poly(ε-caprolactone), poly(ethylene glycol dimethacrylate), gelatin, collagen, agarose, pectin, poly(lysine), bolaamphiphiles, glycosyl-nucleosides, and fluorocarbon chains.

As used herein the term "vinyl polymer" refers to molecules including without limitation, poly(vinyl alcohols) poly(vinyl chlorides), poly(ethylene), poly(propylene), poly(styrene), poly(styrene sulfonate), poly(vinyl chloride), poly(vinyl alcohol), poly(vinyl acetate), poly(vinyl cyanide), poly(vinyl fluoride), poly(vinyl nitrate), poly(vinyl toluene), poly(vinylpyrrolidone), poly(vinylpolypyrrolidone), pluronic polyol, polyoxamer, poly(uronic acid), poly(anhydride), polyNIPAM, poly(acrylates, poly(acrylamides), poly(betaines), tween (20, 40, 60, 80), decyl glucoside glycerol monostearate, glycerol monolaurate, sorbitan monolaurate, sorbitan monostearate, triton x-100, carboxylmethylcellulose, hypromellose, and pluronic F-127. In some embodiments, the listed molecules may be utilized for their emulsification and stabilization properties.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
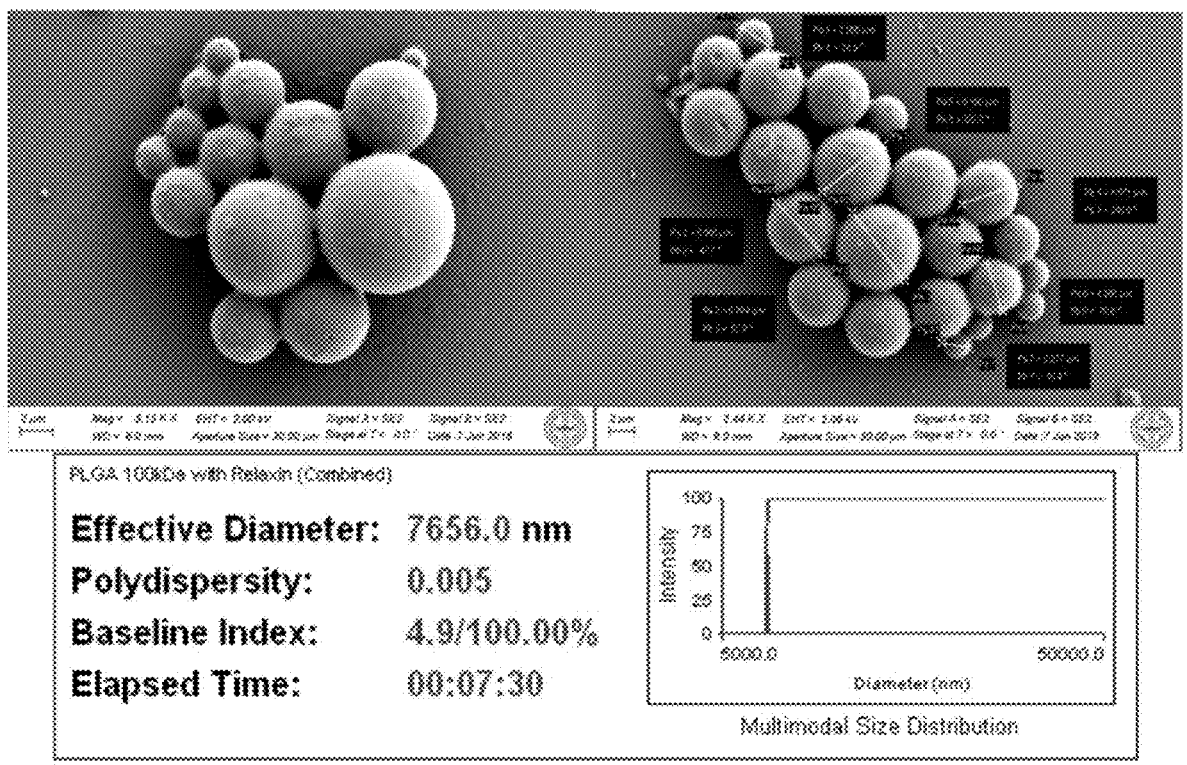
FIG. 1 shows microparticles are prepared with batch-to-batch consistency and low polydispersity. (top) PLGA microparticles encapsulating relaxin-2 show spherical morphology. (bottom) They are synthesized with low polydispersity and a hydrodynamic radius of 7.6 μm as indicated by dynamic light scattering analysis.

Shoulder contracture affects approximately 2% of the U.S. population, or approximately six million individuals. While women are more often affected than men, there is no known genetic or racial predilection (Robinson C. M. et al., *J. Bone Joint Surg. Br.* 2012, 94(1):1-9; Ewald A., *Am. Fam. Physician* 2011, 83(4):417-22). Shoulder contracture recovery is arduous and protracted with a significant number of patients never regaining full joint function. The condition affects both quality of life and productivity. Its predominant feature is painful, gradual loss of both active and passive glenohumeral motion resulting from progressive fibrosis of the glenohumeral joint capsule. The contracted capsule causes pain, especially when it is stretched suddenly, and produces a mechanical restraint to motion. The disease course of primary (idiopathic) shoulder contracture begins with the slow onset (over 2 to 9 months) of pain and stiffness that progressively restricts both passive and active range of motion (ROM) in the glenohumeral joint (Sharma S., *Annals of the Royal College of Surgeons of England* 2011 93(5): 343-4; discussion 5-6). The pain may sharpen at night, leaving patients unable to sleep on the affected side. Subsequently, the pain generally abates over a period of 4 to 12 months, but stiffness severely restricts ROM, particularly in the external rotational plane. There is a slow improvement in ROM over a period of 2 to 4 years. Secondary shoulder contracture has a similar presentation and progression but results from a known intrinsic or extrinsic cause (Sheridan M. A. and Hannafin J. A., *Orthop. Clin. North Am.* 2006, 37(4):531-9). Secondary shoulder contracture following trauma or surgery has a 100% incidence to varying degrees after these events and requires prolonged physical therapy, with original motion not always restored.

Shoulder contracture pathology is a thickened glenohumeral joint capsule with adhesions obliterating the axillary fold. The fibrotic capsule adheres to itself and the anatomic neck of the humerus, intraarticular volume is diminished, and synovial fluid in the joint is significantly decreased (Hand G. C. et al., *J. Bone Joint Surg. Br.* 2007, 89(7):928-32). Biopsy of the capsule shows a chronic inflammatory infiltrate, an absence of synovial lining, and subsynovial fibrosis (Ozaki J. et al., *J Bone Joint Surg. Am.* 1989, 71(10):1511-5; Wiley A. M., *Arthroscopy* 1991, 7(2): 138-43; Rodeo S. A. et al., *J. Orthop. Res.* 1997, 15(3):427-36). Patient biopsy samples confirm the presence of T-cells, B-cells, synovial cells, fibroblasts and transforming myofibroblasts, along with type-I and type-III collagen (Rodeo S. A. et al., *J. Orthop. Res.* 1997, 15(3):427-36; Bunker T. D. et al., *J. Bone Joint Surg. Br.* 2000, 82(5):768-73). Gene and protein expression assays have found products related to fibrosis, inflammation, and chondrogenesis (Hagiwara Y. et al., *Osteoarthritis Cartilage* 2012, 20(3):241-9), including increased COL1A1 and COL1A3, interleukin-6, platelet-derived growth factor (PDGF), fibroblast growth factors (FGF) and inhibitors of the matrix metalloproteinases (TIMPs), as well as decreased activity of matrix metalloproteinases (MMPs). These data indicate that inflammatory changes initiate the recruitment of fibroblasts and immune cells, precipitating the fibrotic process and inappropriate deposition of collagen. Alternatively, fibrotic changes may occur first, followed by inflammation. In this case, fibrosis may result from an underlying disease process, in which cell signaling pathways governing collagen remodeling may be defective (Bunker T. D. et al., *J. Bone Joint Surg. Br.* 2000, 82(5):768-73). For example, patients treated with marimastat, a synthetic TIMP, developed shoulder contractures, and when the marimastat was stopped, the disease regressed (Hutchinson J. W. et al., *J. Bone Joint Surg. Br.* 1998, 80(5):9078).

Shoulder contracture is considered a self-limiting disease, but recovery is protracted and arduous, with a significant number of patients never regaining full ROM. The reported outcomes of conservative therapy (i.e., physical therapy) vary considerably and are highly dependent on how they are measured (Neviaser A. S. and Neviaser R. J., *J. Am. Acad. Orthop. Surg.* 2011, 19(9):536-42). Results tend to be more favorable with subjective outcome measures than with objective outcome measures. In one study, 90% of patients treated with minimal therapy reported satisfaction with their shoulder function (Griggs S. M. et al., *J. Bone Joint Surg. Am.* 2000, 82-A(10):1398-407). However, another that used objective outcomes reported residual pain in 50% of patients and motion deficit in 60% (Shaffer B. et al., *J. Bone Joint Surg. Am.* 1992; 74(5):738-46). Mild to moderate symptoms can persist after 4.4 years following symptom onset of shoulder contracture. For those experiencing severe disease, such functional impairment interferes with daily activities and work-related responsibilities (Hand C. et al., *Journal of Shoulder and Elbow Surgery* 2008, 17(2):231-6). When patients do not respond to conservative management, other treatment options are available. Operative intervention in the form of manipulation under anesthesia may restore motion and decrease pain, but it has been associated with complications such as fracture, tendon rupture, and neurologic injury (Castellarin G. et al., *Archives of Physical Medicine and Rehabilitation* 2004, 85(8):1236-40; Hsu S. Y. and Chan K. M., *International Orthopaedics*, 1991, 15(2):79-83; Parker R. D. et al., *Orthopedics,* 1989, 12(7):989-90). There are reports that manipulation or capsular release do not offer reliable and consistent results (Shaffer B. et al., *J. Bone Joint Surg. Am.* 1992, 74(5):738-46; Ryans I. et al., *Rheumatology* 2005, 44(4):529-35). Accordingly, a more effective and consistent therapy for joint stiffness is needed Aspects described herein provide a microparticle for delivering an antifibrotic agent. For example, a microparticle comprising an aliphatic polyester and an antibribriotic agent. In certain embodiments, the microparticle further comprises a vinyl polymer.

Another aspect of the invention provides a composition or formulation that comprises, consists of, or consists essentially of any of the microparticles described herein.

Other aspects of the invention provide a method for treating a subject having a disease or disorder associated with fibrosis, the method comprising administering to said subject in need thereof any of the microparticles described herein, any of the compositions described herein, or any of formulations described herein to the subject.

Antifibrotic Agents

Described herein are microparticles that comprise an antifibrotic agent

In one embodiment, the antifibrotic agent is an agonist of the receptor RXFP1. In one embodiment, the antifibrotic agent is human relaxin-2 or an analog or variant.

The term "relaxin" as used herein, refers to a polypeptide belonging to the relaxin family (e.g., relaxin-2), a relaxin analog (e.g., a polypeptide that binds to a relaxin receptor), or a fragment (e.g., a bioactive fragment) or variant of any of the foregoing and/or any agent that is an agonist of an agent that binds the relaxin receptor family of proteins (RXFP1, RXFP2, RXFP3, RXFP4).

Relaxin is an approximately 6-kDa protein belonging to the insulin superfamily (Sherwood O. D., *Endocr. Rev.* 2004, 25(2):205-34). Like insulin, relaxin is processed from a prepro-form to the mature hormone, containing A and B peptide chains connected by two interchain disulfide bridges and one intrachain disulfide within the A chain (Chan L. J. et al., *Protein Pept. Lett.* 2011, 18(3):220-9). Relaxin readily decreases collagen secretion and increases collagen degradation by increasing the expression of MMPs and decreasing the expression of TIMPs (Samuel C. S. et al., *Cell Mol. Life Sci.* 2007, 64(12):1539-57). This hormone is involved in reproduction, where it inhibits uterine contraction and induces growth and softening of the cervix to assist child delivery (Parry L. J. et al., *Adv. Exp. Med. Biol.* 2007, 612:34-48). Recently, a highly purified recombinant form of H2 relaxin, or human relaxin-2, has been tested in a number of in vitro and in vivo systems to evaluate both its ability to modify connective tissue and its potential antifibrotic properties. Several studies report that relaxin-2 acts at multiple levels to inhibit fibrogenesis and collagen overexpression associated with fibrosis and is able to prevent and treat pulmonary, renal, cardiac, and hepatic fibrosis (Bennett R. G., *Transl. Res.* 2009, 154(1):1-6). Relaxin treatment of human fibroblasts caused a reduction in levels of collagen types I and III and fibronectin (Unemori E. N. et al., *The Journal of Clinical Investigation* 1996, 98(12):2739-45). In vivo, relaxin-2 decreased collagen build-up in the lung induced by bleomycin and improved the overall amount of fibrosis (Unemori E. N. et al., *The Journal of Clinical Investigation* 1996, 98(12):2739-45). In cultured renal fibroblasts, epithelial cells and mesangial cells, relaxin-2 decreased TGF-β-induced fibronectin levels and increased fibronectin degradation (McDonald G. A. et al., *American Journal of Physiology Renal Physiology* 2003, 285(1):F59-67). Relaxin-2 has been shown to have a rapid pharmacokinetic profile. Previous clinical trials investigating relaxin-2 as a treatment for scleroderma, acute heart failure, and for the induction of labor through cervical ripening, utilized continuous infusion of relaxin-2 via either intravenous administration or subcutaneous administration through a minipump. Efficacy of relaxin-2 requires activation of a transmembrane relaxin receptor for downstream signalling. Previous clinical trials utilized continuous infusion in an attempt to overcome pharmacokinetic limitations. The localized, sustained release of relaxin-2 achieves sustained receptor activation without necessitating continuous administration.

Unless specified to the contrary, the term "relaxin" as used herein encompasses a relaxin or an analog, a fragment (e.g., a bioactive fragment) or a variant thereof. The term "relaxin or an analog, a fragment or a variant thereof" encompasses any member of the relaxin-like peptide family which belongs to the insulin superfamily. The relaxin-like peptide family includes relaxin-like (RLN) peptides, e.g., relaxin-1 (RLN1), relaxin-2 (RLN2) and relaxin-3 (RLN3), and the insulin-like (INSL) peptides, e.g., INSL3, INSL4, INSL5 and INSL6. Representative sequences of human RLN1 are listed herein as SEQ ID NOS: 4-7; representative sequences of human RLN2 are listed herein as SEQ ID NOS: 1-3; representative sequences of human RLN3 are listed herein as SEQ ID NOS: 8-10; a representative sequence of human INSL3 is listed herein as SEQ ID NO: 11; representative sequences of human INSL4 are listed herein as SEQ ID NOS: 12-13; representative sequences of human INSL5 are listed herein as SEQ ID NOS. 14-15; and a representative sequence of human INSL6 is listed herein as SEQ ID NO: 16. In some embodiments, the term "relaxin or an analog, a fragment or a variant thereof may encompass any polypeptide having at least 70%, e.g., at least 75%, at least 80%, at least 85%, at least 90%, at least 95%, 96%, 97%, 98% or at least 99% sequence identity with any of SEQ ID NOS: 1-16, as well as any polypeptide sequence that comprises any of SEQ ID NOS: 1-16. In one embodiment of the invention, the relaxin includes RLN1, RLN2 or RLN3. In one embodiment, the relaxin is relaxin-1. In another embodiment, the relaxin is relaxin-3. In a preferred embodiment, the relaxin is relaxin-2. In another embodiment of the invention, the relaxin includes INSL3, INSL4, INSL5 or INSL6. In one embodiment, the relaxin is INSL3. In one embodiment, the relaxin is INSL4. In one embodiment, the relaxin is INSL5. In one embodiment, the relaxin is INSL6.

In some embodiments, the relaxin is recombinantly produced, for example in a bacterial, mammalian or yeast host cell. In other aspects the relaxin has been fully or partially chemically synthesized.

In some embodiments, the term relaxin encompasses any natural, synthetic, or semi-synthetic composition that is capable of interacting with a relaxin family protein receptors (RXFP1, RXFP2, RXFP3, RXPF4) that impacts the form, function, or activity of the receptor. These compounds include but are not limited to native relaxin-2, relaxin-2 variants, polypeptides, DNA or RNA polynucleotides, small molecules, as well as any of the previously listed compounds conjugated to, or associated with, the relaxin-2 protein.

The term "relaxin or an analog, a fragment or a variant thereof" may also encompass any member the relaxin-like peptide family includes relaxin-like (RLN) peptides, e.g., relaxin-1 (RLN1), relaxin-2 (RLN2) and relaxin-3 (RLN3), and the insulin-like (INSL) peptides, e.g., INSL3, INSL4, INSL5 and INSL6. Representative sequences of human RLN1 are listed herein as SEQ ID NOS: 4-7; representative sequences of human RLN2 are listed herein as SEQ ID NOS: 1-3; representative sequences of human RLN3 are listed herein as SEQ ID NOS: 8-10; representative sequence of human INSL3 is listed herein as SEQ ID NO: 11; representative sequences of human INSL4 are listed herein as SEQ ID NOS: 12-13; representative sequences of human INSL5 are listed herein as SEQ ID NOS. 14-15; and representative sequence of human INSL6 is listed herein as SEQ ID NO: 16. The term "relaxin or an analog, a fragment or a variant thereof" also in some embodiments encompasses any polypeptide having at least 70%, e.g., at least 75%, at least 80%, at least 85%, at least 90%, at least 95% or at least 99% sequence identity with any of SEQ ID NOS: 1-16, as well as any polypeptide sequence that comprises any of SEQ ID NOS: 1-16. In one embodiment of the formulation, the relaxin includes RLN1, RLN2 or RLN3. In one embodiment, the relaxin is relaxin-2. In another embodiment, the relaxin includes INSL3, INSL4, NSL5 or INSL6.

The term "relaxin or an analog, a fragment or a variant thereof" also in some embodiments may encompass any mutant member of the relaxin-like peptide family. Such mutant may be, e.g., a RLN1, RLN2, RLN3, INSL3, INSL4, INSL5 or INSL6 comprising one or more mutations, e.g., substitutions, additions or deletions of one or more amino acids (native or non-native) in the known sequence of RLN1, RLN2, RLN3, INSL3, INSL4, INSL5 or INSL6. For example, a mutant member of the relaxin-like peptide family may comprise any naturally occurring or artificially produced variants of RLN1, RLN2, RLN3, INSL3, INSL4, INSL5 or INSL6.

The term "relaxin fragment" or "a fragment of relaxin" as used herein encompasses a fragment of a relaxin, i.e., a partial sequence of any member of the relaxin-like peptide family, that retains its ability to treat stiffened joints through interaction with the relaxin family receptors. Examples include those sequences described in European Patent Office Application No. EP1641824B1 (Relaxin superfamily peptide analogues), the entire contents of which are incorporated herein by reference.

The term "relaxin analog" or an "analog of relaxin" includes any non-relaxin polypeptide sequence that possesses the biological activity of relaxin, i.e., the ability to interact with the relaxin family receptors. In one embodiment, such polypeptide sequence may comprise prolactin or an analog, a fragment or a variant thereof. In another embodiment, such sequence may comprise the truncated B-chain analogue of relaxin known as B7-33, described in ACS Appl. Mater. Interfaces 2019, 11, 49, 45511-45519.

In some embodiments, the term agent or "relaxin analog" also includes a relaxin receptor agonist, e.g., any agent, such as a small molecule, a polypeptide, a polynucleotide or a polysaccharide, that can bind to and activate a relaxin receptor, e.g., one or more of RXFP1, RXFP2, RXFP3 and RXFP4. For example, a relaxin receptor agonist may be a polypeptide comprising the receptor binding site of relaxin. A relaxin receptor agonist may also be a polypeptide comprising any other sequence capable of binding to and activating the relaxin receptor, e.g., RXFP1, RXFP2, RXFP3 and RXFP4. Other examples include those agonists described in US Patent Application No. US20130237481A1 (Modified relaxin polypeptides and their uses), US Patent Application No. US20180222960A 1 (Modified relaxin polypeptides comprising a pharmacokinetic enhancer and uses thereof), U.S. Pat. No. 8,445,635B2 (Modified H2 relaxin for tumor suppression), European Patent Office Application No. EP3067365A1 (Human relaxin analogue, pharmaceutical composition of same, and pharmaceutical application of same), and US Patent Application No. US20180222960A1 (Modified relaxin polypeptides comprising a pharmacokinetic enhancer and uses thereof) the entire contents of which are incorporated herein by reference.

The term "relaxin or an analog, a fragment or a variant thereof" includes any recombinantly produced relaxin, such as, e.g., Serelaxin (RLX030) developed by Novartis. Methods for producing recombinant relaxin, e.g., relaxin-2, are described, .e.g., in U.S. Pat. No. 5,464,756, the entire contents of which are incorporated herein by reference. The recombinantly produced relaxin or analog, fragment or variant thereof may comprise a relaxin sequence, e.g., RLN1, RLN2, RLN3, INSL3, INSL4, INSL5 or INSL6, and a histidine (His) tag to aid in the purification of the relaxin after being recombinantly produced.

The relaxin or analog, fragment or variant thereof may also comprise one or more chemical modifications, e.g., chemical groups covalently attached to the relaxin or an analog, a fragment or a variant thereof. Such chemical groups may include, e.g., carbohydrates or other polymers, e.g., polyethylene glycol (PEG), e.g., polypeptide, e.g. one or more lipids (Design and Synthesis of Potent, Long-Acting Lipidated Relaxin-2 Analogs, Bioconjugate Chem. 2019, 30, 1, 83-89). Other examples include fragments or variants described in US Patent Application No. US2018/0326079 (NOVEL FATTY ACIDS AND THEIR USE IN CONJUGATION TO BIOMOLECULES), U.S. Pat. No. 9,931,372B2 (SYNTHETIC APELIN FATTYACID CONJUGATES WITH IMPROVED HALF-LIFE), the entire contents of which are incorporated herein by reference.

In some embodiments, relaxin or an analog, a fragment or a variant thereof is co-administered with ML290 or its analog, fragment or a variant to prolong or enhance the effects of RXLP1 activation (Kocan, M., et al. Sci. Rep., 2017).

In some embodiments, the term relaxin includes relaxin attached, e.g., covalently attached, to an immunoglobulin or a fragment of an immunoglobulin, e.g., an antibody or a fragment of an antibody, for example, the immunoglobulin fusion proteins described in WO 2017/100540. In other embodiments, the term relaxin does not include relaxin attached, e.g., covalently attached, to an immunoglobulin or a fragment of an immunoglobulin.

Microparticles, and Compositions and Formulations Thereof

Aspects described herein relate to a microparticle comprising an aliphatic polyester and an antifibriotic agent. Exemplary aliphatic polyesters include poly-lactide-co-glycolide, or polycaprolactone.

In one embodiment, the microparticle further comprises a vinyl polymer. Exemplary vinyl polymers include poly (vinyl alcohol) or poly(pyrrolidone).

Another aspect herein is a microparticle comprising an aliphatic polyester and an antifibrotic agent, the microparticles have a diameter of 1-100 µm.

Another aspect herein is a microparticle comprising an aliphatic polyester and an antifibrotic agent, the antifibrotic agent is relaxin and is present in an amount that is 0.01-33% of total mass.

Another aspect herein is a microparticle comprising an aliphatic polyester and an antifibrotic agent, the aliphatic polyester is of molecular weight 10,000-200,000 daltons.

Another aspect herein is a microparticle comprising an aliphatic polyester, a vinyl polymer and an antifibrotic agent.

Another aspect herein is a microparticle comprising an aliphatic polyester, a vinyl polymer and an antifibrotic agent, the microparticles have a diameter of 1-100 µm.

Another aspect herein is a microparticle comprising an aliphatic polyester, a vinyl polymer and an antifibrotic agent, the antifibrotic agent is relaxin and is present in an amount that is 0.01-33% of total mass.

Another aspect herein is a microparticle comprising an aliphatic polyester, a vinyl polymer and an antifibrotic agent, the aliphatic polyester is of molecular weight 10,000-200,000 daltons.

Another aspect herein is a PLGA microparticle comprising an aliphatic polyester and an antifibrotic agent, the microparticles have a diameter of 1-100 m.

Another aspect herein is a PLGA microparticle comprising an aliphatic polyester and an antifibrotic agent, the antifibrotic agent is relaxin and is present in an amount that is 0.01-33% of total mass.

Another aspect herein is a PLGA microparticle comprising an aliphatic polyester and an antifibrotic agent, the aliphatic polyester is of molecular weight 10,000-200,000 daltons.

Another aspect herein is a PLGA microparticle comprising an aliphatic polyester, a vinyl polymer and an antifibrotic agent, the microparticles have a diameter of 1-50 µm.

Another aspect herein is a PLGA microparticle comprising an aliphatic polyester, a vinyl polymer and an antifibrotic agent, the antifibrotic agent is relaxin and is present in an amount that is 0.1-33% of total mass.

Another aspect herein is a PLGA microparticle comprising an aliphatic polyester, a vinyl polymer and an antifibrotic agent, the aliphatic polyester is of molecular weight 10,000-200,000 daltons.

In one embodiment, where a feature of a formulation (such as an antifibrotic agent, a relaxin, a vinyl polymer, an aliphatic polyester, etc) is in a specified amount expressed in a mass percentage; percent-by-weight; percent of total mass or the like; unless indicated otherwise, the percentage is based on microparticles that are not suspended in a solution. In such situations where a claimed formulation includes microparticles suspended in a solution, the mass percentage still refers to the mass percentage in the microparticles, and not the total solution that includes the microparticles and the suspension solution.

Pharmaceutical Compositions

Various aspects herein relate to a composition comprising any of the microparticles described herein. In various embodiments, the composition is a pharmaceutical composition.

As used herein, the term "pharmaceutical composition" can include any material or substance that, when combined with an active ingredient (e.g., an antifibrotic agent, such as relaxin), allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups and elixirs. In addition, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In some embodiments, the liquid dosage form is prepared at or near the point of care by reconstituting or resuspending a provided lyophilisate or lyophilized powder of a formulation disclosed herein using a diluent solution.

Solid dosage forms for oral administration include capsules, tablets, pills, powders, and granules. In such solid dosage forms, the agents described herein are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragées, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

In some embodiments, the solid dosage form is a lyophilized powder.

In some dosage forms, the lyophilized powder solid dosage form is intended to be resuspended or reconstituted with diluent.

The agent can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms, the agent can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present invention can be formulated for colonic or rectal administration.

The present invention provides sustained release formulations for delivering a polypeptide therapeutic to a subject in need thereof. The sustained release formulations of the invention consist of a hydrogel, microparticle or some matrix encapsulation of the agent. One example of the agent is relaxin. The sustained release comprises the agent e.g., relaxin encapsulated by or chemically bound to the depot support material via a linker. The linker may, comprise a polymer, a non-cleavable linker, or a cleavable linker, either through chemical or enzymatic means. The depot may be formed in situ following mixing of the agent with the material. The depot may be formed prior to mixing of the relaxin with the material.

The sustained release formulation comprising the agent e.g., relaxin may be in the form of a hydrogel or microparticle which comprises one or more polymers. The polymers that may be used in a sustained release relaxin formulation may include, without limitation, polyethylene glycol (PEG), alginate, agarose, poly(ethylene glycol dimethacrylate), polylactic acid, polyglycolic acid, poly-lactide-co-glycolide, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly (uronic acid), poly(anhydride), poly(vinylpyrrolidone), bolaamphiphiles, glycosyl-nucleosides, and fluorocarbon chains.

In some embodiments of any of the aspects described herein, an agent is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533;

5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm & Haas, Spring House, Pa. USA).

In some embodiments, any aforementioned polymers, prior to or after loading of relaxin, may be characterized (e.g. size, molecular weight, charge, secondary structure, and purity) by techniques including, but not limited to, gel permeation chromatography, high performance liquid chromatography, ultra-performance liquid chromatography, MALDI-TOF mass spectroscopy, viscometry, and light scattering (e.g. multi-angle, low angle laser).

In some embodiments, the rate of release of relaxin may be characterized by techniques including, but not limited to, high performance liquid chromatography, ultra-performance liquid chromatography, fast protein liquid chromatography, enzyme linked immunosorbent assay, and ligand binding assay. In some embodiments, the release rate of relaxin is measured as the concentration of relaxin in any biologically relevant liquid solution or suspension or medium (e.g. saline, mammalian cell culture media, synthetic synovial fluid, synovial fluid, serum, synthetic serum, plasma, synthetic plasma and deionized water) that the formulation is also in. In specific embodiments, the formulation and biologically relevant liquid solution or suspension is maintained at a specific temperature. In specific embodiments, the formulation and biologically relevant liquid solution or suspension is agitated or mixed at a set or varying rate of motion. In specific embodiments, the concentration of relaxin released into the biologically relevant liquid solution or suspension is measured using a direct enzyme linked immunosorbent assay. In specific embodiments, the concentration of relaxin released into the biologically relevant liquid solution or suspension is measured using an indirect enzyme linked immunosorbent assay. In specific embodiments, the concentration of relaxin released into the biologically relevant liquid solution or suspension is measured using a sandwich enzyme linked immunosorbent assay. In a preferred embodiment, the concentration of relaxin released into the biologically relevant liquid solution or suspension is measured using the Human Relaxin-2 Quantikine ELISA Kit from Bio-techne corporation.

In some embodiments, the size and morphology (e.g. diameter, sphericity, and porosity) of relaxin microparticles may be characterized by techniques including, but not limited to, dynamic light scattering, coulter counter, microscopy, sieve analysis, dynamic image analysis, static image analysis, and laser diffraction.

In some embodiments, the total loaded content of relaxin in relaxin microparticles (e.g. percent of relaxin as weight/volume, percent of relaxin as weight/weight) may be characterized by techniques including, but not limited to, mass balance, high performance liquid chromatography, ultra-performance liquid chromatography, fast protein liquid chromatography, enzyme linked immunosorbent assay, and ligand binding assay. In some embodiments, the formulation may be purified and dissolved to assess total loaded content of relaxin.

In some embodiments, the total loaded content (i.e. mass) of relaxin in relaxin microparticles is measured as the concentration of relaxin in any liquid solution, suspension or medium (e.g. saline, mammalian cell culture media, synthetic synovial fluid, synovial fluid, serum, synthetic serum, plasma, synthetic plasma, methylene chloride, acetonitrile, ethyl acetate, and deionized water) that the total formulation may be dissolved in. In specific embodiments, the concentration of relaxin after formulation dissolution in the liquid solution, suspension, or medium is measured using a direct enzyme linked immunosorbent assay. In specific embodiments, the concentration of relaxin after formulation dissolution in the liquid solution, suspension, of medium is measured using an indirect enzyme linked immunosorbent assay. In specific embodiments, the concentration of relaxin after formulation dissolution in the liquid solution, suspension, of medium is measured using a sandwich enzyme linked immunosorbent assay. In a preferred embodiment, the concentration of relaxin after formulation dissolution in the liquid solution, suspension, of medium is measured using the Human Relaxin-2 Quantikine ELISA Kit from Bio-techne corporation.

In certain embodiments, the sustained release formulation comprises of PEG, e.g., a linear PEG or a branched PEG. In certain embodiments, the molecular weight of the PEG is more than 0.2 kDa, more than 0.5 kDa, more than 1 kDa, more than 5 kDa, more than 10 kDa, or more than 20 kDa In some embodiments, the hydrogel comprises of PEG-based crosslinkers with an internal thioester that will be reacted with dendrons to prepare hydrogels. These hydrogels may be prepared in varying weight percent to modulate mechanical properties. In specific embodiments the internal thioester allows for controlled dissolution through the use of a cysteine methyl ester solution. In specific embodiments, the gels material properties including, but not limited to, release profile, young's modulus, sheer modulus, hydrophobicity, and, elasticity can be varied through modification of the thioester moiety to modulate material properties of hydrogel.

In one embodiment of any aspect herein, the aliphatic polyester is poly-lactide-co-glycolide.

In one embodiment of any aspect herein, the aliphatic polyester is polycaprolactone.

In one embodiment of any aspect herein, the aliphatic polyester is of molecular weight 10,000-200,000 daltons; 10,000-150,000 daltons; or 25,000-125,000 daltons; or 40,00-100,000 daltons; 10,000-30,000 daltons; 30,000-50,000 daltons; 50,000-70,000 daltons; 70,000-90,000 daltons; 90,000-120,000 daltons; or 120,000-150,000 daltons.

In one embodiment of any aspect herein, the aliphatic polyester is terminated by an ester functional group.

In one embodiment of any aspect herein, the aliphatic polyester is terminated by an alkyl-ester functional group.

In one embodiment of any aspect herein, the aliphatic polyester is terminated by a carboxylic acid functional group.

In one embodiment of any aspect herein, the aliphatic polyester is terminated by an amine functional group, an isocyanate functional group, an isothiocyanate functional group, a benzoyl fluoride functional group, a maleimide functional group, an iodoacetamide functional group, a 2-thiopyridine functional groups, a 3-arylpropiolonitrile functional group, a diazonium salt, an aldehyde, a ketone, an azide, an alkyne, a cyclooctyne, or a phosphine. In one embodiment of any aspect herein, these functional groups that allow for bioconjuntion between the PLGA and a biomolecule.

In one embodiment of any aspect herein, the formulation comprises a vinyl polymer that is poly(vinyl alcohol).

In one embodiment of any aspect herein, the formulation comprises a vinyl polymer that is poly(pyrrolidone).

In one embodiment of any aspect herein, the formulation comprises a vinyl polymer that is of molecular weight 10,000-200,000 daltons; 10,000-150,000 daltons; or 25,000-125,000 daltons; or 40,00-100,000 daltons; 10,000-30,000 daltons; 30,000-50,000 daltons; 50,000-70,000 daltons; 70,000-90,000 daltons; 90,000-120,000 daltons; or 120,000-150,000 daltons.

In one embodiment of any aspect herein, the diameter of the microparticles is 1-100 μm.

In one embodiment of any aspect herein, the diameter of the microparticles is 1-75 μm; or 1-50 μm; or 5-50 μm; or 25-50 μm; or 30-50 μm; or 40-50 μm; or 5-10 μm; 5-8 μm; 8-12 μm; 12-18 μm; 18-25 μm; 25-35 μm; 35-45 μm; 45-50 μm; 1 μm; 2 μm; 3 μm; 4 μm; 5 μm; 6 μm; 7 μm; 8 μm; 9 μm; 10 μm; 15 μm; 20 μm; 25 μm; 30 μm; 35 μm; 40 μm; 45 μm; 50 μm; 75 μm; 100 μm; 150 μm; or 200 μm.

In one embodiment of any aspect herein, the aliphatic polyester is poly-lactide-co-glycolide with a molar ratio of 15:85-25:75, lactide:glycolide; poly-lactide-co-glycolide with a molar ratio of 25:75-35:65, lactide:glycolide; poly-lactide-co-glycolide with a molar ratio of 35:65-45:55, lactide:glycolide; poly-lactide-co-glycolide with a molar ratio of 45:55-55:45, lactide:glycolide; poly-lactide-co-glycolide with a molar ratio of 55:45-65:35, lactide:glycolide; poly-lactide-co-glycolide with a molar ratio of 65:35-75:25, lactide:glycolide; poly-lactide-co-glycolide with a molar ratio of 75:25-85:15, lactide:glycolide; poly-lactide-co-glycolide with a molar ratio of about 50:50, lactide:glycolide; poly-lactide-co-glycolide with a molar ratio of about 45:55, lactide:glycolide; poly-lactide-co-glycolide with a molar ratio of about 55:45, lactide:glycolide; poly-lactide-co-glycolide with a molar ratio of about 40:60, lactide:glycolide; or poly-lactide-co-glycolide with a molar ratio of about 60:40, lactide:glycolide.

In one embodiment of any aspect herein, the formulation comprises a vinyl polymer that is about 0.01-0.1% of total mass; 0.1-0.3% of total mass; 0.2-0.9% of total mass; 0.3-0.7% of total mass; 0.4-0.6% of total mass; 0.3-0.6% of total mass; 0.6-1.0% of total mass; 1.0-5.0% of total mass; 5.0-10.0% of total mass; 10.0-30.0% of total mass; 0.1% of total mass; 0.2% of total mass; 0.3% of total mass; 0.4% of total mass; 0.5% of total mass; 0.6% of total mass; 0.7% of total mass; 0.8% of total mass; 0.9% of total mass; 10% of total mass; 15% of total mass; 20% of total mass; 25% of total mass; 30% of total mass; or 33% of total mass.

In one embodiment of any aspect herein, the antifibrotic agent is 0.005-5% of the total formulation mass. In one embodiment of any aspect herein, the antifibrotic agent is 0.01-10%, 0.01-33%, or 0.1-5% of the total formulation mass; or 0.24% of the total formulation mass; or 0.3-3% of the total formulation mass; or 0.5-2% of the total formulation mass; or 0.5-1.5% of the total formulation mass; or 0.5-3% of the total formulation mass; or 1-2% of the total formulation mass; or 1-5% of the total formulation mass; or 3-7% of the total formulation mass; or 5-10% of the total formulation mass.

In one embodiment of any aspect herein, the antifibrotic agent is about 0.005-0.01% of the total formulation mass; 0.01-0.05% of the total formulation mass; 0.05-0.1% of the total formulation mass; 0.1-0.5% of the total formulation mass; 0.5-1.0% of the total formulation mass; 1.0-2.5% of the total formulation mass; 2.5-5.0% of the total formulation mass; 0.25% of the total formulation mass; 0.5% of the total formulation mass; 0.75% of the total formulation mass; 1% of the total formulation mass; 1.25% of the total formulation mass; 1.5% of the total formulation mass; 1.75% of the total formulation mass; 2% of the total formulation mass; 2.5% of the total formulation mass; 3% of the total formulation mass; or 5% of the total formulation mass.

In one embodiment of any aspect herein, the formulation comprises PLGA microparticles with a PLGA molar ratio that is about 50:50 lactide:glycolide, a relaxin loaded at about 1% by weight of the microparticles, and PVA in a concentration of about 0.5% by weight.

In one embodiment of any aspect herein, the formulation comprises PLGA microparticles with a PLGA molar ratio that is about 50:50 lactide:glycolide, a relaxin loaded at about 1% by weight of the microparticles and PVA in a concentration of about 0.0% by weight In one embodiment of any aspect herein, the formulation comprises PLGA microparticles with a PLGA molar ratio that is about 60:40 lactide:glycolide, a relaxin loaded at about 1% by weight of the microparticles, and PVA in a concentration of about 0.5% by weight.

In one embodiment of any aspect herein, the formulation comprises PLGA microparticles with a PLGA molar ratio that is 40:60 lactide:glycolide, a relaxin loaded at about 1% by weight of the microparticles, and PVA in a concentration of about 0.5% by weight.

In one embodiment of any aspect herein, the formulation comprises microparticles suspended in a liquid solution.

In one embodiment of any aspect herein; the formulation comprises microparticles suspended in a sodium chloride liquid solution.

In one embodiment of any aspect herein, the formulation comprises microparticles suspended in a sodium chloride liquid solution; the sodium chloride is 0.5-1.5 w/w %; or between 0.75-1.25 w/w %; or about 0.5 w/w %; or about 0.6 w/w %; or about 0.7 w/w %; or about 0.8 w/w %; or about 0.9 w/w %; or about 1.0 w/w %; or about 1.1 w/w %; or about 1.2 w/w %; or about 1.3 w/w %; or about 1.4 w/w %; or about 1.5 w/w % of the liquid solution.

In one embodiment of any aspect herein; the formulation comprises microparticles suspended in a sodium carboxymethylcellulose solution.

In one embodiment of any aspect herein, the formulation comprises microparticles suspended in a sodium carboxymethylcellulose solution; the sodium carboxymethylcellulose solution is 0.1-1.0 w/w %; or between 0.25-0.75 w/w %; or about 0.1 w/w %; or about 0.2 w/w %; or about 0.3 w/w %; or about 0.4 w/w %; or about 0.5 w/w %; or about 0.6 w/w %; or about 0.7 w/w %; or about 0.8 w/w %; or about 0.9 w/w %; or about 1.0 w/w % of the liquid solution.

In one embodiment of any aspect herein, the formulation is a sustained release formulation.

In one embodiment of any aspect herein, the formulation is a sustained release formulation the antifibrotic agent is released over an extended period of time.

For relaxin to have a sustained clinical antifibrotic effect, it is physiologically desirable for the temporal concentration of relaxin to be above the minimum effective concentration for a sustained duration. A bolus dose of relaxin is reported to not be effective in animals. A sustained dose of relaxin is reported to be effective in animals.

A constant sustained dose of relaxin may be achieved by the relase of relaxin from a microparticle with a linear rate of release (i.e. one having no bolus effect or burst-release effect).

In one embodiment of any aspect herein, the formulation is a sustained release formulation the antifibrotic agent is released over an extended period of least 1 day; or at least 2 days; or at least 3 days; or at least 4 days; or at least 5 days; or at least 6 days; or at least 1 week; or at least 2 weeks; or at least 3 weeks; or at least 4 weeks; or at least 5 weeks, or at least 6 weeks; or at least 8 weeks; or at least 9 weeks; at least 10 weeks; or at least 12 weeks; or at least 15 weeks; or between 1-5 days; or between 2-5 days; or between 1-2 days; or between 2-3 days; or between 3-4 days; or between 4-5 days; or between 3-10 days; or between 1-15 weeks; or between 2-10 weeks; or between 4-8 weeks; or between 8-15 weeks; or about 1 day; or about 2 days; or about 3 days; or about 4 days; or about 5 days; or about 6 days; or about 1 week; or about 2 weeks; or about 3 weeks; or about 4 weeks; or about 5 weeks; or about 6 weeks; or about 7 weeks; or about 8 weeks; or about 9 weeks; or about 10 weeks, or more.

Treatment of Diseases or Disorders Associated with Fibrosis

In some embodiments, a formulation as described herein is administered to a subject. In some embodiments, a formulation as described herein is used to treat an organ or location on the body of a subject, a disease or indication in a subject and or using an administration route as described in Table 1 and/or Table 2.

TABLE 1

| Administration routes and targets | Sites (non-joints) | Lung, kidney, liver, heart, skin, eye; tendons, osteotendinous junctions, tendon-bone interfaces, entheses, or muscle-tendon insertions, mentioning a slew of tendons throughout the body |
|---|---|---|
| | Sites (joints) | Jaw, spine, shoulder, elbow, wrist, hand, finger, hip, knee, ankle, foot, toe; or any other synovial or non-synovial joint |
| | Routes of administration | JOINT INJECTIONS (JI): Intraarticular, periarticular, intracapsular, pericapsular NON-JOINT DENSE CONNECTIVE TISSUE INJECTIONS (NJDCTI): intraligamentous, periligamentous, intratendinous, peritendinous, intraosteotendinous, or periosteotendinous; intramusculotendinous, perimusculotendinous, perimuscularly, OTHER, NON-ORTHOPEDIC: intravenously, intramuscularly, subcutaneously, intradermally, intranasally, orally, transcutaneously (ionto/electrophoresis), mucosally, gel, cream, ointment, lotion, drop, suppository, spray, liquid, powder, pulmonary inhalation, ocular. |
| Indications | When to administer treatment | During or just after a medical procedure; for patients with stiffened joint or at risk for stiffened joint (treatment or prophylactic) |

TABLE 2

| General causes of fibrosis | Idiopathic, injury (trauma, medical procedure e.g. surgery), immobility for whatever reason, inflammation, or disease/medical condition |
|---|---|
| Diseases/conditions: joints (admin via joint injection) | adhesive capsulitis (injury, idiopathic, post-surgical, post-implant) |
| Diseases/conditions: lung (admin via inhalation) | idiopathic pulmonary fibrosis, cystic fibrosis, hypertension |
| Diseases/conditions: liver | hepatitis B or C, long-term alcohol abuse, non-alcoholic steatohepatitis, non-alcoholic fatty liver disease, Cholestasis, autoimmune hepatitis cirrhosis |
| Diseases/conditions: kidney | chronic kidney disease, end-stage renal disease, renal interstitial fibrosis |
| Diseases/conditions: heart | heart failure, myocardial infarction, aortic stenosis, hypertrophic cardiomyopathy |
| Diseases/conditions: intestine | Crohn's disease, inflammatory bowel disease, enteropathies |
| Diseases/conditions: skin (admin via intradermal injection, or transdermal) | scleroderma, keloids, hypertrophic scars, cellulite |
| Diseases/conditions: urogenital/gynecological | Peyronie's disease, uterine fibroids, urethral strictures |
| Diseases/conditions: ocular | Congenital Fibrosis of the Extraocular Muscles, subretinal fibrosis, epiretinal fibrosis, corneal fibrosis |
| Diseases/conditions: connective tissue, fascia | Dupuytren's disease, capsular contracture of breast, Plantar fibromatosis, |
| Diseases/conditions: neuromuscular (admin via joint or peri-joint injection) | Duchenne, Becker, congenital, and other muscular dystrophies, SMA, Charcot-Marie-Tooth, arthrogryposis, ALS, club foot, post-polio, CP. |

In some embodiments, a method is provided in which the method involves identifying a subject diagnosed with one or more diseases selected from the group of diseases listed in Table 1 or Table 2 and administering a formulation of the invention to the subject. In some embodiments, a method is provided in which the method involves identifying a subject diagnosed with one or more diseases selected from the group of diseases consisting of Duchenne Muscular Dystrophy, Becker Muscular Dystrophy, Spinal Muscular Atrophy-Type I, Spinal Muscular Atrophy-Type II, Spinal Muscular Atrophy-Type III, Spinal Muscular Atrophy-Type IV, Cerebral Palsy, Stroke, Traumatic Brain Injury, peripheral nerve injury, and Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature and cellulite and administering to said patient a composition or formulation of the invention.

Stiffened Joint

Various compositions and methods disclosed herein may be useful for treating various aspects, precursors and related disorders of joint stiffness. Joint stiffness is a significant public health issue with current treatment options providing varied and limited outcomes. Joint stiffness can affect any joint in the body, such as a shoulder joint, an elbow joint, a wrist joint, a finger joint, a hip joint, a knee joint, an ankle joint, a toe joint, the spine and the jaw A shoulder joint is often affected by joint stiffness, which is also termed a shoulder contracture, and is also known as "frozen shoulder".

Shoulder contracture affects approximately 2% of the U.S. population, or approximately six million individuals. While women are more often affected than men, there is no known genetic or racial predilection (Robinson C. M. et al., J. Bone Joint Surg. Br. 2012, 94(1):1-9; Ewald A., Am. Fam. Physician 2011, 83(4):417-22). Shoulder contracture recovery is arduous and protracted with a significant number of patients never regaining full joint function. The condition affects both quality of life and productivity. Its predominant feature is painful, gradual loss of both active and passive glenohumeral motion resulting from progressive fibrosis of the glenohumeral joint capsule. The contracted capsule causes pain, especially when it is stretched suddenly, and produces a mechanical restraint to motion. The disease course of primary (idiopathic) shoulder contracture begins with the slow onset (over 2 to 9 months) of pain and stiffness that progressively restricts both passive and active range of motion (ROM) in the glenohumeral joint (Sharma S., Annals of the Royal College of Surgeons of England 2011 93(5): 343-4; discussion 5-6). The pain may sharpen at night, leaving patients unable to sleep on the affected side. Subsequently, the pain generally abates over a period of 4 to 12 months, but stiffness severely restricts ROM, particularly in the external rotational plane. There is a slow improvement in ROM over a period of 2 to 4 years. Secondary shoulder contracture has a similar presentation and progression but results from a known intrinsic or extrinsic cause (Sheridan M. A. and Hannafin J. A., Orthop. Clin. North Am. 2006, 37(4):531-9). Secondary shoulder contracture following trauma or surgery has a 100% incidence to varying degrees after these events and requires prolonged physical therapy, with original motion not always restored.

Shoulder contracture pathology is a thickened glenohumeral joint capsule with adhesions obliterating the axillary fold. The fibrotic capsule adheres to itself and the anatomic neck of the humerus, intraarticular volume is diminished, and synovial fluid in the joint is significantly decreased (Hand G. C. et al., J. Bone Joint Surg. Br. 2007, 89(7):928-32). Biopsy of the capsule shows a chronic inflammatory infiltrate, an absence of synovial lining, and subsynovial fibrosis (Ozaki J. et al., J. Bone Joint Surg. Am. 1989, 71(10):1511-5; Wiley A. M., Arthroscopy 1991, 7(2): 138-43; Rodeo S. A. et al., J. Orthop. Res. 1997, 15(3):427-36). Patient biopsy samples confirm the presence of T-cells, B-cells, synovial cells, fibroblasts and transforming myofibroblasts, along with type-I and type-III collagen (Rodeo S. A. et al., J. Orthop. Res. 1997, 15(3):427-36; Bunker T. D. et al., J. Bone Joint Surg. Br. 2000, 82(5):768-73). Gene and protein expression assays have found products related to fibrosis, inflammation, and chondrogenesis (Hagiwara Y. et al., Osteoarthritis Cartilage 2012, 20(3):241-9), including increased COLIA1 and COLIA3, interleukin-6, platelet-derived growth factor (PDGF), fibroblast growth factors (FGF) and inhibitors of the matrix metalloproteinases (TIMPs), as well as decreased activity of matrix metalloproteinases (MMPs). These data indicate that inflammatory changes initiate the recruitment of fibroblasts and immune cells, precipitating the fibrotic process and inappropriate deposition of collagen. Alternatively, fibrotic changes may occur first, followed by inflammation. In this case, fibrosis may result from an underlying disease process, in which cell signaling pathways governing collagen remodeling may be defective (Bunker T. D. et al., J. Bone Joint Surg. Br. 2000, 82(5):768-73). For example, patients treated with marimastat, a synthetic TIMP, developed shoulder contractures, and when the marimastat was stopped, the disease regressed (Hutchinson J. W. et al., J. Bone Joint Surg. Br. 1998, 80(5):907-8).

Shoulder contracture is considered a self-limiting disease, but recovery is protracted and arduous, with a significant number of patients never regaining full ROM. The reported outcomes of conservative therapy (i.e., physical therapy) vary considerably and are highly dependent on how they are measured (Neviaser A. S. and Neviaser R. J., J. Am. Acad. Orthop. Surg. 2011, 19(9):536-42). Results tend to be more favorable with subjective outcome measures than with objective outcome measures. In one study, 90% of patients treated with minimal therapy reported satisfaction with their shoulder function (Griggs S. M. et al., J. Bone Joint Surg. Am. 2000, 82-A(10):1398-407). However, another that used objective outcomes reported residual pain in 50% of patients and motion deficit in 60% (Shaffer B. et al., J. Bone Joint Surg. Am. 1992; 74(5):738-46). Mild to moderate symptoms can persist after 4.4 years following symptom onset of shoulder contracture. For those experiencing severe disease, such functional impairment interferes with daily activities and work-related responsibilities (Hand C. et al., Journal of Shoulder and Elbow Surgery 2008, 17(2):231-6). When patients do not respond to conservative management, other treatment options are available. Operative intervention in the form of manipulation under anesthesia may restore motion and decrease pain, but it has been associated with complications such as fracture, tendon rupture, and neurologic injury (Castellarin G. et al., Archives of Physical Medicine and Rehabilitation 2004, 85(8):1236-40; Hsu S. Y. and Chan K. M., International Orthopaedics, 1991, 15(2):79-83; Parker R. D. et al., Orthopedics, 1989, 12(7):989-90). There are reports that manipulation or capsular release do not offer reliable and consistent results (Shaffer B. et al., J. Bone Joint Surg. Am. 1992, 74(5):738-46; Ryans I. et al., Rheumatology 2005, 44(4):529-35). Accordingly, a more effective and consistent therapy for joint stiffness is needed.

Encapsulation of biologically active agents into biocompatible and biodegradable polymeric matrices prior to administration prolongs effective therapeutic levels in a patient. Hydrogels and microparticles are implantable structures. They are desirable for therapeutic delivery due to designs that are biocompatible, made of non-toxic constituents, not immunogenic or cause irritation and do not hinder the target tissue structurally or mechanically. Significantly, they can be administered locally to the area of interest. One material that is extensively used for microencapsulation and prolonged release of small molecule drugs, DNA and proteins is poly(lactic-co-glycolic) acid (PLGA). PLGA is biocompatible and releases its payload both through diffusion of out of the polymer matrix and via breakdown of the polymer matrix. The breakdown occurs through hydrolysis of PLGA, catalyzed by the body's aqueous environment, into lactic acid and glycolic acid, which are byproducts of cellular metabolism. It is considered safe for administration to humans by the United States Food and Drug Administration (Han, F. C. et al., Front. Pharmacol. 2016, 7(185)). PLGA microparticles can be optimized for sustained drug release by adjusting the ratio of lactic acid to glycolic acid and the emulsification protocol. However, it has been reported to cause a foreign body response.

Techniques for encapsulation of a biologically active agent inside lactide, glycolide co-polymer microparticles are known. The production techniques generally include either the use of two solvent phases, stabilizer, and the biologically active agent dissolved or solvated into one of the phases or the use of water/oil/water (w/o/w) or water/oil (w/o) emulsions. In the first mentioned production technique, the two phases, biologically active agent and stabilizer are emulsifier and then one of the phases is removed, leaving behind a microparticle with stabilized, loaded agent. In the w/o/w fabrication technique, the initial water phase contains or does not contain the biologically active compound, is emulsified within the organic phase containing the dissolved polymeric matrix and then emulsified within the second aqueous phase. The removal of the organic phase leaves behind a microparticle containing or not containing the biologically active compound. That said the specific methods and PLGA compositions used highly depend on the encapsulant and a general procedure/composition does not exist for all encapsulants.

Another promising material for use specifically in the field of regenerative medicine and tissue maintenance as a drug delivery system are hydrogels. These hydrogels are polymeric networks capable of encapsulating biologically active agents. Hydrogels possess relevant biological properties such as biocompatibility, sheering thinning characteristics, biodegradation, and do not impact the stability or activity of the loaded biologically active agent.

One such formulation of hydrogels involves a network of low molecular weight gelators (LMWG) that act as injectable scaffolds for biomedical applications. They have tunable physiochemical and biological properties due to their supramolecular structure stemming from the self-assembly of small molecules. Specifically, LMWGs with bolaamphiphiles consisting of a N-thymine glycosylated head groups linked to a lipidic moiety via either urea or amide functions have shown to be fast-gelling with high in vivo stability and do not activate macrophages (FIG. 1) (Ramen, F. A. et al., Biomaterials. 2017, 145: 72-80). Another LMWG formulation utilizes a combination of glycosyl-nucleosides and fluorocarbon chains as amphiphiles that self-assemble into highly organized structures that increases stability of hydrogel formulations (FIG. 1) (Godeau, G., et al., Tetrahedron Letters 2010, 51: 1012-1015). They demonstrated numerous advantageous properties, including biocompatibility, control over structure and purity, easy handling procedure to allow for incorporation of proteins, mechanical stability and are non-toxic to cells (Godeau, G., et al., Tetrahedron Letters 2010, 51: 1012-1015; Ramen, F. A. et al., Biomaterials. 2017, 145: 72-80).

Another formulation of hydrogels is the use of a PEG-based hydrogel. In this formulation the PEG-based hydrogel would include polymeric PEG matrix with a biologically active agent either linked or encapsulated to the matrix. Encapsulation would occur through localization of the biological agent into the hydrogel during polymerization. Release of the agent would occur through diffusion out of the hydrogel into the tissue. In the case of a chemical bond between the agent and the hydrogel, it would be either a cleavable or non-cleavable connection. If cleavable, the linkage would be either rely upon an enzymatic or non-enyzmatic based mechanism.

Rigid contracture or fibrosis (arthrofibrosis) of the major articular joints is a severely limiting comorbidity and sequela of many neuromotor degenerative disorders. It presents as an accumulation of fibrotic collagenous tissue within the joint and manifests as a painful and longstanding restriction of joint range of motion (ROM), contributing to poor mobility and requiring home care assistance or institutionalization.

Stiffened joint may be most limiting in the shoulders, elbows, knees, hips, wrists, and ankles of patients with progressive neuromotor disorders. Degenerative disorders that may be treated by formulations and methods provided herein and that lead to arthrofibrosis and have different etiologies and include, but are not limited to, Duchenne (DMD) and Becker (BMD) muscular dystrophies, Congenital Muscular Dystrophies (CMD), Spinal Muscular Atrophy (SMA), Charcot-Marie-Tooth disease (CMT), arthrogryposis, Emery Dreifus Muscular Dystrophy (EMD), the family of slow progressive muscular dystrophies (Limb-girdle (LGMD), Fascioscapulohumeral (FSH), Congenital Myotonic (CMMD)), Amyotrophic Lateral Sclerosis (ALS), idiopathic congenital club foot, post-polio syndrome, all forms of cerebral palsy (1,2), (CP), stroke, traumatic brain injury, and peripheral nerve injury. Incidence of these conditions is on the order of 1-10/100,000 population for the dystrophies and 2-3/1000 births for cerebral palsy (2). The national cost burden of management of these conditions is significant, with population-wide national costs just for managing three of these diseases estimated to be $1,023 million (ALS), $787 million (DMD), and $448 million (CMMD)(3). The CDC estimates the overall cost of care for the population of patients with cerebral palsy born in the year 2000, will exceed 11.5 billion (4). These expenses represent medical as well as non-medical costs, and account primarily for musculoskeletal care.

The lack of joint mobility caused by arthrofibrosis in patients with a neuromotor degenerative condition or neuromotor trauma, such as stroke, traumatic brain injury, and peripheral nerve injury, contributes to further muscle tone loss, muscle fibrosis and scarring, osteoporosis, secondary deformities such as spinal scoliosis and lower extremity equinus posture, and loss of skin integrity. Ultimately, arthrofibrosis results in inability to ambulate and limits activities of daily living. In the stages of disease when patients may no longer be ambulatory, joint contracture further burdens nursing care, rest positioning, sitting, and hygiene (1).

At present, prolonged physical therapy, forceful passive stretching, serial casting, and bracing are the only non-operative treatment modalities available, with or without botulism toxin supplementation to diminish muscle associated contracture (1). Surgical Interventions to improve mobility of a fibrosed joint include manipulation under anesthesia, tendon and muscle releases, and articular capsular release or resection surgeries of the involved joints (5). Manipulation of a joint under anesthesia can result in periarticular and shaft fractures, when forceful mobilization of the fibrosed joint introduces more stress to the adjacent osteoporotic bone than it can tolerate. Many patients are also poor candidates given the intubation and ventilation required for the application of a paralyzing anesthetic agent to counter muscle resistance during a manipulation or surgical release. After prolonged periods of contracture, acute surgical joint release and manipulation may also result in severe nerve and vascular stretch injuries, with inconsistent results and variable recurrence rates.

The overall health and quality of life for these patients would be greatly enhanced by an alternative non-operative treatment modality aimed at resolving joint contracture. This invention, in some embodiments, provides a solution and is a non-surgical office-based intra-articular injection therapy to be used in conjunction with physical therapy to release contracted joints over a two to eight-week period.

In various aspects and embodiments, the compositions and methods provided herein can be of value to a wide range of subjects. Patients with neuromotor degenerative disease are a highly managed population, requiring a lifetime of intensive and costly medical and non-medical support. The current standard of care is either conservative treatment or surgical intervention. In contrast, the compositions and methods provided herein may in some embodiments provide a therapeutic benefit with an in-office injection, eliminating surgery, and offering mobility to an immobile patient, improving their overall health and quality of life and reducing the intensity of supportive care. Caretakers, physicians, and specialists will be able to restore joint motion without performing surgery on this at-risk patient population. Patients will benefit from improved motion and require less physical therapy to maintain joint mobility. They would retain an independent ability to mobilize and perform activities of daily living for longer periods of time as their condition progresses. They would enjoy overall improved musculoskeletal health and psychosocial benefit. For the payor, the overall health care cost for the management of these conditions would decrease as surgical cost per patient would decrease in addition to the higher likelihood that a patient would be able to remain at home longer and not require institutional care for sequela of poor mobility or inability to perform adequate care and hygiene at home.

The present invention provides methods for treating or preventing a stiffened joint in a subject in need thereof. The methods comprise of administering to the subject an effective amount of an agent or ligand of the relaxin family receptors, a relaxin-2 variant, relaxin-2 chemically conjugated to a targeting agent, including a single-domain camelid antibody fragment, a peptide sequence, polynucleotide, or a small molecule, such that the stiffened joint or surrounding tissue area in the subject is treated.

The current methods for treating a stiffened joint include physical therapy or surgical procedures, such as manipulations and releases, which do not offer reliable or consistent results (Diercks R. L. et al., J. Shoulder Elbow Surg. 2004, 13(5):499-502). Physical therapy involves prolonged manipulation by a physical therapist and surgical procedures involves invasive surgical release by a surgeon, followed again by prolonged therapy. Another current method, the Ponseti method, involves serial re-casting after stretching, sometimes with surgical release of contracted tendons.

The methods of the invention are, in some embodiments, advantageous as compared to many currently available methods because they can be used to reliably and effectively treat a stiffened joint or tissue area, while also using a minimally invasive procedure, e.g., an intraarticular injection, which may be performed in an outpatient setting or an office. Thus, some methods of the invention constitute a paradigm shift in the management of a stiffened joint, e.g., a shoulder joint, that may result from fibrosis. Some methods of the invention involve minimally invasive procedures, e.g., an intraarticular or periarticular injection of relaxin-2, e.g., relaxin-2 encapsulated in a sustained release formulation. The intraarticular injection may be repeated as needed until the stiffened joint is successfully treated, e.g., until motion in the joint is restored and pain during motion is eliminated. Successful treatment of a stiffened joint when using some methods of the invention may be accomplished significantly faster and more effectively than when using the currently available methods.

Pathology of a stiffened joint, e.g., a shoulder joint, includes a thickened glenohumeral joint capsule with adhesions obliterating the axillary fold. The fibrotic capsule adheres to itself and the anatomic neck of the humerus, intraarticular volume is diminished, and synovial fluid in the joint is significantly decreased. Biopsy of the capsule shows a chronic inflammatory infiltrate, with the presence of fibroblasts and transforming myofibroblasts, along with type-I and type-III collagen. Gene and protein expression assays have found components related to fibrosis, inflammation, and chondrogenesis, including increased COL1A1 and COL1A3, interleukin-6 (IL-6), platelet-derived growth factor (PDGF), fibroblast growth factors (FGF) and TMPs, as well as decreased MMP activity. This evidence points to inflammatory changes initiating the recruitment of fibroblasts and immune cells, precipitating the fibrotic process and inappropriate deposition of excess collagen. Alternatively, it is also possible that fibrosis occurs first, followed by inflammation; fibrosis being secondary to defective cell-signaling pathways governing collagen remodeling.

Without wishing to be bound by a specific theory, it is believed that the agent e.g., relaxin, when delivered to or near a joint, e.g., via a hydrogel or particle, intraarticular injection, sustained release formulation, promotes collagen degradation, thereby altering the homeostasis of the extracellular matrix (ECM) in the synovium. This administration results in decreased joint stiffness and increased range of motion of the joint.

In one embodiment, the antifibrotic agent of the invention is administered as a monotherapy. In one embodiment, the antifibrotic agent of the invention is administered with at least one additional therapeutic. Exemplary additional therapeutics include, but are not limited to, an addition antifibrotic therapeutic or physical therapy.

In some embodiments, relaxin or an analog, a fragment or a variant thereof is co-administered with other native antifibrotic agents such as IFN-α, IFN-β, srli B, M3, MMP1, MMP8. Additionally, the use of other anti-fibrotic agents that target receptors other than the relaxin receptor: TGF-beta inhibitors (Esbriet, pirfenidone), tyrosine kinase inhibitors (Ofev, nintedanib). PPAR (peroxisome proliferatoractivated receptors) agonists (Ianifibranor, IVA337), IL-1 inhibitors (Arcalyst, rilonacept), IL-6 inhibitors (Actmera, tocilizumab), B-cell inhibitors (rituximab), T-cell inhibitors (Orencia, abatacept), lysophosphatidic acid inhibitors (SAR100842, Sanofi), Halofunginone, d-penicillamine, colchicine, cyclosporine, TGF beta blockers, p38 MAPK blockers Methods for Treating a Stiffened Joint Some aspects of the present invention provide methods for treating or preventing a stiffened joint. As used herein, the terms "treating", "treat" or "treatment" refer to a beneficial or desired result including, but not limited to, alleviation or amelioration of one or more symptoms associated with a stiffened joint (e.g., pain on movement of the joint, loss of motion of the joint or loss of the range of motion of the joint); diminishing the restriction of movement resulting from a stiffened joint; stabilization (i.e., not worsening) of the joint stiffness; amelioration or palliation of the restriction of movement resulting from a stiffened joint (e.g., pain on movement of the joint, loss of motion of the joint or loss of the range of motion of the joint) whether detectable or undetectable.

In some embodiments, methods of the present invention result in a treatment of the stiffened joint, such that pain on movement of the joint is reduced, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, and is preferably down to a level accepted within the range of normal for an individual who is not affected by a stiffened joint.

In some embodiments, methods of the present invention result in restoration of the movement, or a range of the movement, of a joint affected by joint stiffness. For example, treatment of the stiffened joint according to the methods of the invention may result in restoration of the movement, or a range of movement, of a joint affected by joint stiffness, to levels that are at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the levels accepted within the range of normal for an individual not affected by a stiffened joint.

In some embodiments, prevention or treatment of a stiffened joint in a subject provided by the methods of the present invention is accomplished without significant adverse events, without significant damage to collagenous structures or tissues in the subject, e.g., collagenous structures or tissues of the joint, such as articular cartilage of the joint. For example, methods of the present invention provide prevention and treatment of stiffened joint that do not disrupt architecture of the joint. Damage to collagenous structures in the body, e.g., collagenous structures of a joint, may be assessed by methods known in the art, e.g., by measuring levels of various markers in the synovial fluid, such as Cartilage Oligomeric Matrix Protein (COMP), aggrecans, collagen II, proteoglycans, MMPs and inflammatory mediators and cytokines. Imaging techniques such as MRI can also be used to visualize the joint and the cartilage architecture.

In some embodiments, when the agent (e.g., relaxin) loaded depot is administered intraarticularly, prevention or treatments of stiffened joint by the methods of the present invention is accomplished without significant adverse events associated with systemic administration of relaxin. In a phase III clinical trial for use of relaxin to treat systemic sclerosis, some of the patients that received a 24-week subcutaneous infusion of relaxin had declines in creatine clearance and renal adverse events; however renal physiology abnormalities are associated with systemic sclerosis and may have predisposed the affected patients to such renal events when combined with relaxin treatment (Khanna, D., et al., Arthritis and Rheumatism 2009, 60(4): 1102-1111). When relaxin is administered intraarticularly by methods of the present invention, serum creatine levels, protein levels in the urine, blood cell count, hemoglobin concentration in the blood and systolic and diastolic blood pressure will be monitored during and after administration for prevention or treatment of a stiffened joint for indication of renal crisis and hypertension.

One aspect provided herein is a method, said method comprising identifying a subject diagnosed with one or more diseases selected from the group of diseases listed in Table 1 or Table 2 and administering a formulation of any one of the preceding embodiments to the subject.

Another aspect provided herein is a method, said method comprising identifying a subject diagnosed with Duchenne Muscular Dystrophy and administering to said patient a composition or formulation of any of the preceding embodiments.

Another aspect provided herein is a method, said method comprising identifying a subject diagnosed with Becker Muscular Dystrophy and administering to said patient a composition or formulation of any of the preceding embodiments.

Another aspect provided herein is a method, said method comprising identifying a subject diagnosed with Spinal Muscular Atrophy, Type I, and administering to said patient a composition or formulation of any of the preceding embodiments.

Another aspect provided herein is a method, said method comprising identifying a subject diagnosed with Spinal Muscular Atrophy, Type II, and administering to said patient a composition or formulation of any of the preceding embodiments.

Another aspect provided herein is a method, said method comprising identifying a subject diagnosed with Spinal Muscular Atrophy, Type III, and administering to said patient a composition or formulation of any of the preceding embodiments.

Another aspect provided herein is a method, said method comprising identifying a subject diagnosed with Spinal Muscular Atrophy, Type IV, and administering to said patient a composition or formulation of any of the preceding embodiments.

Another aspect provided herein is a method, said method comprising identifying a subject diagnosed with Cerebral Palsy and administering to said patient a composition or formulation of any of the preceding embodiments.

Another aspect provided herein is a method, said method comprising identifying a subject diagnosed with Arthrogryposis Multiplex Congenita and administering to said patient a composition or formulation of any of the preceding embodiments.

Another aspect provided herein is a method, said method comprising identifying a subject with fibrosis of the humero-radial joint and administering to said patient a composition or formulation of any of the preceding embodiments.

Another aspect provided herein is a method, said method comprising identifying a subject with fibrosis of the humeroulnar joint and administering to said patient a composition or formulation of any of the preceding embodiments.

Another aspect provided herein is a method, said method comprising identifying a subject with fibrosis of the glenohumeral joint and administering to said patient a composition or formulation of any of the preceding embodiments.

Another aspect provided herein is a method, said method comprising identifying a subject with fibrosis of the tibiofemoral joint and administering to said patient a composition or formulation of any of the preceding embodiments.

Another aspect provided herein is a method, said method comprising identifying a subject with fibrosis of the acetabulofemoral joint and administering to said patient a composition or formulation of any of the preceding embodiments.

Another aspect provided herein is a method, said method comprising identifying a subject with fibrosis of the talocrural joint and administering to said patient a composition or formulation of any of the preceding embodiments.

Another aspect provided herein is a method, said method comprising identifying a subject with fibrosis of the temporomandibular joint and administering to said patient a composition or formulation of any of the preceding embodiments.

Another aspect provided herein is a method, said method comprising identifying a subject with fibrosis of the metacarpophalangeal joint and administering to said patient a composition or formulation of any of the preceding embodiments.

Another aspect provided herein is a method, said method comprising identifying a subject with fibrosis of the metatarsophalangeal joint and administering to said patient a composition or formulation of any of the preceding embodiments.

Another aspect provided herein is a method, said method comprising identifying a subject with fibrosis of the periarticular musculature and administering to said patient a composition or formulation of any of the preceding embodiments.

Another aspect provided herein is a method, said method comprising identifying a subject with cellulite and administering to said patient a composition or formulation of any of the preceding embodiments.

Another aspect provided herein is a method, said method comprising identifying a subject with interstitial lung disease and administering to said patient a composition or formulation of any of the preceding embodiments.

Another aspect provided herein is a method, said method comprising administering, to any of the preceding subjects, a composition or formulation of any of the preceding embodiments, via inhalation as an aerosol.

Another aspect provided herein is a method, said method comprising administering, to any of the preceding subjects, a composition or formulation of any of the preceding embodiments, via intra-articular injection.

Another aspect provided herein is a method, said method comprising administering, to any of the preceding subjects, a composition or formulation of any of the preceding embodiments, via intramuscular injection.

Another aspect provided herein is a method, said method comprising administering, to any of the preceding subjects, a composition or formulation of any of the preceding embodiments, via intradermal injection.

Another aspect provided herein is a method, said method comprising administering, to any of the preceding subjects, a composition or formulation of any of the preceding embodiments, via subcutaneous injection.

Another aspect provided herein is a method, said method comprising administering, to any of the preceding subjects, a composition or formulation of any of the preceding embodiments, via intracapsular injection.

Another aspect provided herein is a method, said method comprising administering, to any of the preceding subjects, a composition or formulation of any of the preceding embodiments, via pericapsular injection.

Another aspect provided herein is a method, said method comprising administering, to any of the preceding subjects, a composition or formulation of any of the preceding embodiments, via intraligamentous injection.

Another aspect provided herein is a method, said method comprising administering, to any of the preceding subjects, a composition or formulation of any of the preceding embodiments, via periligamentous injection.

Another aspect provided herein is a method, said method comprising administering, to any of the preceding subjects, a composition or formulation of any of the preceding embodiments, via intratendinous injection.

Another aspect provided herein is a method, said method comprising administering, to any of the preceding subjects, a composition or formulation of any of the preceding embodiments, via peritendinous injection.

Another aspect provided herein is a method, said method comprising administering, to any of the preceding subjects, a composition or formulation of any of the preceding embodiments, via intramusculotendinous injection.

Another aspect provided herein is a method, said method comprising administering, to any of the preceding subjects, a composition or formulation of any of the preceding embodiments, via perimusculotendinous injection.

Another aspect provided herein is a method, said method comprising administering, to any of the preceding subjects, a composition or formulation of any of the preceding embodiments, via intraosteotendinous injection.

Another aspect provided herein is a method, said method comprising administering, to any of the preceding subjects, a composition or formulation of any of the preceding embodiments, via periosteotendinous injection.

Another aspect provided herein is a method, said method comprising administering, to a subject diagnosed with Duchene's muscular dystrophy, a composition or formulation of any of the preceding embodiments, via intramuscular injection.

Another aspect provided herein is a method, said method comprising administering, to a subject diagnosed with Duchene's muscular dystrophy, a composition or formulation of any of the preceding embodiments, via intraarticular injection.

Another aspect provided herein is a method, said method comprising administering, to a subject diagnosed with Becker's muscular dystrophy, a composition or formulation of any of the preceding embodiments, via intramuscular injection.

Another aspect provided herein is a method, said method comprising administering, to a subject diagnosed with Becker's muscular dystrophy, a composition or formulation of any of the preceding embodiments, via intraarticular injection Another aspect provided herein is a method, said method comprising administering, to a subject diagnosed with Spinal Muscular Dystrophy, a composition or formulation of any of the preceding embodiments, via intramuscular injection.

Another aspect provided herein is a method, said method comprising administering, to a subject diagnosed with Spinal Muscular Dystrophy, a composition or formulation of any of the preceding embodiments, via intraarticular injection.

Another aspect provided herein is a method, said method comprising administering, to a subject diagnosed with Arthrogryposis Multiplex Congenita, a composition or formulation of any of the preceding embodiments, via intramuscular injection.

Another aspect provided herein is a method, said method comprising administering, to a subject diagnosed with Arthrogryposis Multiplex Congenita, a composition or formulation of any of the preceding embodiments, via intraarticular injection.

Another aspect provided herein is a method, said method comprising administering, to a subject diagnosed with Cerebral Palsy, a composition or formulation of any of the preceding embodiments, via intramuscular injection.

Another aspect provided herein is a method, said method comprising administering, to a subject diagnosed with Stroke, a composition or formulation of any of the preceding embodiments, via intramuscular injection.

Another aspect provided herein is a method, said method comprising administering, to a subject diagnosed with Stroke, a composition or formulation of any of the preceding embodiments, via intraarticular injection.

Another aspect provided herein is a method, said method comprising administering, to a subject diagnosed with Traumatic Brain Injury, a composition or formulation of any of the preceding embodiments, via intramuscular injection.

Another aspect provided herein is a method, said method comprising administering, to a subject diagnosed with Traumatic Brain Injury, a composition or formulation of any of the preceding embodiments, via intraarticular injection.

Another aspect provided herein is a method, said method comprising administering, to a subject diagnosed with Peripheral Nerve Injury, a composition or formulation of any of the preceding embodiments, via intramuscular injection.

Another aspect provided herein is a method, said method comprising administering, to a subject diagnosed with Peripheral Nerve Injury, a composition or formulation of any of the preceding embodiments, via intraarticular injection.

Another aspect provided herein is a method, said method comprising administering, to a subject diagnosed with Cerebral Palsy, a composition or formulation of any of the preceding embodiments, via intraarticular injection.

Another aspect provided herein is a method, said method comprising administering any of the preceding embodiments with sizes between 1 um-10 μm via inhalation as an aerosol.

Another aspect provided herein is a method, said method comprising administering any of the preceding embodiments with sizes between 20 um-100 μm via intramuscular injection.

Another aspect provided herein is a method, said method comprising administering any of the preceding embodiments with sizes between 5 um-50 μum via intraarticular injection.

Another aspect provided herein is a method, said method comprising administering, to a subject diagnosed with interstitial lung disease any of the preceding embodiments via inhalation as an aerosol.

Another aspect provided herein is a method, said method comprising administering, to a subject diagnosed with interstitial lung disease any of the preceding embodiments via inhalation as an aerosol.

Another aspect provided herein is a method, said method comprising administering, to a subject diagnosed with interstitial lung disease any of the preceding embodiments, wherein the diameter of the microparticle is 1-10 μm, via inhalation as an aerosol.

Another aspect provided herein is a method, said method comprising administering, to a subject diagnosed with Duchene's Muscular Dystrophy any of the preceding embodiments, wherein the diameter of the microparticle is 10-30 μm, via intraarticular injection.

Another aspect provided herein is a method, said method comprising administering, to a subject diagnosed with Duchene's Muscular Dystrophy any of the preceding embodiments, wherein the diameter of the microparticle is 25-50 μm, via intraarticular injection.

Another aspect provided herein is a method, said method comprising administering, to a subject diagnosed with Duchene's Muscular Dystrophy any of the preceding embodiments, wherein the diameter of the microparticle is 10-30 μm, via intramuscular injection.

Another aspect provided herein is a method, said method comprising administering, to a subject diagnosed with Duchene's Muscular Dystrophy any of the preceding embodiments, wherein the diameter of the microparticle is 25-50 μm, via intramuscular injection.

Another aspect provided herein is a method, said method comprising administering, to a subject diagnosed with Spinal Muscular Atrophy any of the preceding embodiments, wherein the diameter of the microparticle is 10-30 μm, via intraarticular injection.

Another aspect provided herein is a method, said method comprising administering, to a subject diagnosed with Spinal Muscular Atrophy any of the preceding embodiments, wherein the diameter of the microparticle is 25-50 μm, via intraarticular injection.

Another aspect provided herein is a method, said method comprising administering, to a subject diagnosed with Spinal Muscular Atrophy any of the preceding embodiments, wherein the diameter of the microparticle is 10-30 μm, via intramuscular injection.

Another aspect provided herein is a method, said method comprising administering, to a subject diagnosed with Spinal Muscular Atrophy any of the preceding embodiments, wherein the diameter of the microparticle is 25-50 μm, via intramuscular injection.

Another aspect provided herein is a method, said method comprising administering, to a subject diagnosed with joint arthrofibrosis any of the preceding embodiments, wherein the diameter of the microparticle is 10-30 μm, via intraarticular injection.

Another aspect provided herein is a method, said method comprising administering, to a subject diagnosed with joint arthrofibrosis any of the preceding embodiments, wherein the diameter of the microparticle is 25-50 μm, via intraarticular injection.

Another aspect provided herein is a method or formulation of any of the preceding embodiments, wherein the formulation is delivered via inhalation as an aerosol.

Another aspect provided herein is a method or formulation of any of the preceding embodiments, wherein the formulation is delivered via intra-articular injection.

Another aspect provided herein is a method or formulation of any of the preceding embodiments, wherein the formulation is delivered via intramuscular injection.

In one embodiment, method or formulation of any one of the preceding embodiments wherein, the formulation is administered to the subject such that the antifibrotic agent (e.g., a relaxin) is administered to a subject at a dose between 1-2000 μg/kg body weight; or between 10-100 μg/kg body weight; or between 100-200 µg/kg body weight; or between 200-500 µg/kg body weight; or between 500-1000 µg/kg body weight; or 25-75 µg/kg body weight; or 30-70 µg/kg body weight; or 40-60 µg/kg body weight; or between 1-10 µg/kg body weight; or between 1-5 µg/kg body weight; or between 4-8 µg/kg body weight; or about 2 µg/kg body weight; or about 5 µg/kg body weight; or about 10 µg/kg body weight; or about 20 µg/kg body weight; or about 25 µg/kg body weight; or about 30 µg/kg body weight; or about 35 µg/kg body weight; or about 40 µg/kg body weight; or about 45 µg/kg body weight; or about 50 µg/kg body weight; or about 55 µg/kg body weight; or about 60 µg/kg body weight; or about 65 µg/kg body weight; or about 70 µg/kg body weight; or about 75 µg/kg body weight; or about 100 µg/kg body weight; or about 200 µg/kg body weight; or about 500 µg/kg body weight.

Administration

In some embodiments, methods of the invention comprise administering an agent e.g., relaxin or an analog, a fragment or a variant thereof to a subject using a depot. The terms "administer", "administering" or "administration" include any method of delivery of agent into the subject's system or to a particular region in or on the subject. For example, relaxin or agent loaded depot may be administered intravenously, intramuscularly, subcutaneously, intradermally, intranasally, orally, transcutaneously, mucosally, intraarticularly, periarticularly, intracapsularly, pericapsularly, intratendinously, peritendinously, intraligamentously, periligamentously, by pulmonary inhalation or by ocular specific routes of administration. Administering the agent loaded depot can be performed by a number of people working in concert and can include, for example, prescribing relaxin or an analog, a fragment or a variant thereof to be administered to a subject via a depot and/or providing instructions, directly or through another, to take the relaxin or an analog, a fragment or a variant thereof, either by self-delivery via a depot, e.g., as by oral delivery, subcutaneous delivery, intravenous delivery through a central line, etc., or for delivery by a trained professional, e.g., intra-articular delivery, intravenous delivery, intramuscular delivery, intratumoral delivery, etc.

In a preferred embodiment, the agent e.g., relaxin or an analog, a fragment or a variant thereof is administered locally, e.g., directly to or into a joint of a subject using a depot. Local administration of the agent (e.g., relaxin) loaded depot by an intraarticular injection or by topical application to the joint, or in the tissue surrounding the joint is advantageous because it allows delivery of a smaller dose of the agent to the subject and avoids the side-effects associated with systemic delivery, such as back pain and joint pain.

For example, in a prior clinical investigation of relaxin for treating heart failure, relaxin was dosed at 30 micrograms/kg/day for 2 days systemically (intravenous infusion), and did not meet the trial's primary endpoint of effectiveness. In another prior clinical investigation of relaxin for treating scleroderma, relaxin was dosed at 25 micrograms/kg/day for 24 weeks systemically (subcutaneous delivery), and did not meet the trial's primary endpoint of effectiveness. In contrast, formulations of the present disclosure may delivery relaxin locally (opposed to systemically) at an effective dose of about 0.1 microgram/kg/day for about 4 or for about 6 weeks, and may demonstrate clinical effectiveness.

In one embodiment, the agent e.g., relaxin loaded depot is administered to the subject by an intraarticular injection. In one embodiment, the agent e.g., relaxin loaded depot is administered to the subject by an intraarticular, periarticular, intracapsular, pericapsular, intraligamentous, periligamentous, intratendinous, peritendinous, intraosteotendinous, or periosteotendinous injection (collectively "joint injections"), or combination thereof. In one embodiment, the agent e.g., relaxin loaded depot is administered to the subject via a single joint injection. In one embodiment, the agent e.g., relaxin loaded depot is administered to the subject via multiple joint injections. The multiple joint injections of the agent e.g., relaxin loaded depot may be administered to a subject at regularly spaced time intervals, e.g., every day, every 2 days, every 3 days, every 4 days, every 5 days, every 6 days, every 7 days, every 8 days, every 9 days, every 10 days, every 11 days, every 12 days every 13 days or every 14 days. A course of treatment consisting of multiple joint injections of agent e.g., relaxin loaded depot may be repeated.

In one embodiment, the agent is administered to or near tendons, osteotendinous junctions, tendon-bone interfaces, entheses, or muscle-tendon insertions. Such tissues may be selected from the following tendinous tissues, among others:

Shoulder
    Teres Minor Tendons (Rotator Cuff) Infraspinatus Tendons Supraspinatus Tendons Subscapularis Tendons Elbow/Forearm
    Deltoid Tendons Biceps Tendons Triceps Tendons Brachioradialis Tendons Extensor Carpi Radialis Brevis Tendons Extensor Carpi Radialis Longus Tendons Supinator Tendons Wrist
    Flexor Carpi Radialis Tendons Flexor Carpi Ulnaris Tendons Extensor Capri Radialis Tendons Extensor Carpi Radialis Brevis Tendons Hip/Groin
    Iliopsoas Tendons Obturator Internus Tendons Adductor Longus, Brevis, and Magnus Tendons Gluteus Maximus and Gluteus Medius Tendons Iliotibial Band Knee
    Quadriceps Tendons Patellar Tendons Hamstring Tendons Sartorius Tendons Ankle
    Gastrocnemius Tendons Achilles Tendons Soleus Tendons Tibialis Anterior Tendons Peroneus Longus Tendons Hand (Fingers)
    Flexor Digitorum Longus Tendons Interosseus Tendons Flexor Digitorum Profundus Tendons Abductor Digiti Minimi Tendons Hand (Thumb)
    Opponens Pollicis Tendons Flexor Pollicis Tendons Extensor and Abductor Pollicis Tendons Foot (Toes)
    Flexor Hallucis Longus Tendons Flexor Digitorum Brevis Tendons Lumbrical Tendons Abductor Hallucis Tendons Flexor Digitorum Longus Tendons Abductor Digiti Minimi Tendons Plantar Fasciitis Back
    Multifidus Tendons Quadratus Lumborum Tendons Longissmus Thoracis Tendons Iliocostalis Tendons Spinalis Thoracis Tendons Psoas Major Tendons The joint injection of the agent e.g., relaxin loaded depot may be accomplished by using a syringe with a needle suited for a joint injection. A needle suitable for an joint injection may be selected from the group consisting of a 30 G needle, a 29 G needle, a 28 G needle, a 27 G needle, a 26 sG needle, a 26 G needle, a 25.5 G needle, a 25 sG needle, a 25 G needle, a 24.5 G needle, a 24 G needle, a 23.5 G needle, a 23 sG needle, a 23 G needle, a 22.5 G needle, a 22 sG needle, a 22 G needle, a 21.5 G needle, a 21 G needle, a 20.5 G needle, a 20 G needle, a 19.5 G needle, a 19 G needle, a 18.5 G needle and an 18 G needle. In a specific embodiment, the agent e.g., relaxin loaded depot is administered via a 21 G needle.

In another preferred embodiment, the agent e.g., relaxin loaded depot may be administered to a subject topically, e.g., transcutaneously. For example, the agent e.g., relaxin loaded depot may be administered as a gel, a cream, an ointment, a lotion, a drop, a suppository, a spray, a liquid or a powder composition that is applied topically to a joint, e.g., a finger joint.

In some embodiments, the agent e.g., relaxin loaded depot may be administered to a subject during a medical procedure, e.g., a surgery, to treat or prevent a stiffened joint. Because stiffened joint may result from a surgery, administering relaxin during surgery may prevent formation of a stiffened joint in a subject. In one embodiment, the agent e.g., relaxin loaded depot may be administered through a cannula or an incision.

In another embodiment, the agent e.g., relaxin loaded depot may be administered during an outpatient arthroscopic, fluoroscopic or ultrasound guided procedure.

In a preferred embodiment, the agent e.g., relaxin loaded depot is administered to the subject locally in as a sustained release formulation. Administering relaxin as a sustained release formulation is advantageous because it avoids repeated injections and can deliver a therapeutic dose of the relaxin in a consistent and reliable manner, and over a desired period of time. Exemplary sustained release formulations that may be used to delivery polypeptides, are described in Vaishya et al., *Expert. Opin. Drug Deliv.* 2015, 12(3):415-40, the entire contents of which are incorporated herein by reference.

Certain embodiments of the invention provide a solution to secondary arthrofibrosis developed in neuromotor degenerative diseases by the local intra-articular delivery of relaxin-2, for example in a sustained release formulation. In some embodiments, Relaxin-2 may reduce fibrosis in an in-vivo neuromotor degenerative arthrofibrosis large animal model by inhibiting TGF-β1 signaling via the NO-sGC-cGMP pathway, thereby decreasing joint stiffness and increasing range of motion.

In some embodiments, the formulation is provided as a lyophilized powder for resuspension or reconstitution with diluent at or near the point of care.

Clinically, the treating physician may inject a formulation as disclosed herein, such as relaxin-2 microparticle formulation, in the afflicted contracted joints and periarticular tissues of patients with progressive neuromotor degenerative conditions. These injections will take place in an office setting using anatomical landmarks or under ultrasound guidance. The injections may be followed by a standard course of physical therapy. For more difficult joint injections (i.e., hip, spine), fluoroscopic guided injections can also be performed by an orthopedic surgeon or an interventional radiologist. In some embodiments, advantages may be: Elimination of surgery in a high-risk; Reduction of lifetime health care costs; Local injection of relaxin-2 in the synovial joint space via standard office injection techniques; Minimization of dose as a result of local and not systemic delivery; reduction of off-target side effects and increased safety due to local delivery.

In addition to the tissues around joint, the formulation can treat fibrosis in additional target organs that express the relaxin receptor through different routes of administration.

For lung fibrosis such as insterstitial lung disease, idiopathic pulmonary fibrosis, cystic fibrosis, hypertension, the formulation can be administered by pulmonary inhalation or intranasally as a sustained release formulation and may be provided a single injections or doses or a series of injections or doses.

For liver fibrosis such as hepatitis B or C, long-term alcohol abuse, non-alcoholic steatohepatitis, non-alcoholic fatty liver disease, Cholestasis, autoimmune hepatitis cirrhosis; kidney fibrosis such as chronic kidney disease, end-stage renal disease, renal interstitial fibrosis; and heart disease such as heart failure, myocardial infarction, aortic stenosis, hypertrophic cardiomyopathy, the formulation can be administered intravenously, intramuscularly or intravenously (such as by catheter) as a sustained release formulation and may be provided a single injections or doses or a series of injections or doses.

For intestinal diseases such as Crohn's disease, inflammatory bowel disease, enteropathies, and other intestinal fibrosis, the formulations can be administered intranasally, orally, mucosally, as a sustained release formulation and may be provided a single injections or doses or a series of injections or doses.

For skin conditions such as scleroderma, keloids, hypertrophic scars, cellulite, the formulations can be administered intramuscularly, subcutaneously, intradermally, or transcutaneously as a sustained release formulation and may be provided a single injections or doses or a series of injections or doses.

For urogenital and gynecological conditions such as Peyronie's disease and uterine fibroids, the formulations can be administered transcutaneously or transmucosally as a sustained release formulation and may be provided a single injections or doses or a series of injections or doses.

For ocular diseases such as Congenital Fibrosis of the Extraocular Muscles, subretinal fibrosis, epiretinal fibrosis, corneal fibrosis, the formulation can be administered topically, by local ocular administration (ie, subconjunctival, subretinal, intravitreal, retrobulbar, intracameral), or systemically (ie orally, intravenously, nasally) as a sustained release formulation and may be provided a single injections or doses or a series of injections or doses. Additional diseases and conditions suitable for treatment include Dupuytren's Disease (the formation of a collagen cord in the palm that contracts and limits range of motion of fingers) Peyronie's Disease (excess of inelastic collagen causes penis curvature; distorts erection), Canine and Human Lipomas encapsulated deposits of benign fatty tumors), Uterine Fibroids (benign tumors with significant co-morbidities), Plantar Fibromatosis (pain and disability caused by the thickening of the feet's deep connective tissue), Capsular Contracture, Breast (post-surgical complication that can deform the breast and cause pain), Hypertrophic Scars & Keloids (scars that form on the skin at site of injury), Dercum's Disease (obesity and overly sensitive painful adipose tissue) Knee Arthrofibrosis (adhesions that form post-implant that may affect range of motion), Urethral Strictures Narrowing (Narrowing of the urethra that affects urine flow).

The microparticles and agents described herein can be administered to a subject having or diagnosed as having a disease or disorder associated with fibrosis. In some embodiments, the methods described herein comprise administering an effective amount of a microparticle or agent to a subject in order to alleviate at least one symptom of the disease or disorder. As used herein, "alleviating at least one symptom of the disease or disorder associated with fibrosis" is ameliorating any condition or symptom associated with the fibrotic disease or disorder. As compared with an equivalent untreated control, such reduction is by at least 5%, 10%, 20%, 40%, 50%, 60%, 80%, 90%, 95%, 99% or more as measured by any standard technique. A variety of means for administering the agents described herein to subjects are known to those of skill in the art. In one embodiment of any of the aspects, the agent is administered systemically or locally (e.g., to the brain, or other affected organ, e.g., the colon).

In one embodiment of any of the aspects, the agent is administered intravenously. In one embodiment of any of the aspects, the agent is administered continuously, in intervals, or sporadically. The route of administration of the agent will be optimized for the type of agent being delivered (e.g., an antibody, a small molecule, an RNAi), and can be determined by a skilled practitioner.

The term "effective amount" as used herein refers to the amount of a microparticle or anti-fibrotic agent as described herein can be administered to a subject having or diagnosed as having a disease or disorder associated with fibrosis needed to alleviate at least one or more symptom of the disease or disorder. The term "therapeutically effective amount" therefore refers to an amount of an agent that is sufficient to provide a particular anti-disease or disorder effect when administered to a typical subject. An effective amount as used herein, in various contexts, would also include an amount of a microparticle or agent sufficient to delay the development of a symptom of the disease or disorder, alter the course of a symptom of the disease or disorder (e.g., inflammation, stiffening of a joint, pain, loss of mobility, difficulty breathing), or reverse a symptom of the disease or disorder (e.g., inflammation, stiffening of a joint, pain, loss of mobility, difficulty breathing). Thus, it is not generally practicable to specify an exact "effective amount". However, for any given case, an appropriate "effective amount" can be determined by one of ordinary skill in the art using only routine experimentation.

In one embodiment of any of the aspects, the agent is administered continuously (e.g., at constant levels over a period of time). Continuous administration of an agent can be achieved, e.g., by epidermal patches, continuous release formulations, or on-body injectors.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., measuring neurological function, or blood work, among others. The dosage can be determined by a physician and adjusted, as necessary, to suit observed effects of the treatment.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another, embodiment more than one unit dosage form can be administered simultaneously.

The dosage of the agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

The effective dose can be estimated initially from cell culture assays. A dose can be formulated in animals. Generally, the compositions are administered so that a compound of the invention herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this invention, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

Combinational Therapy

In one embodiment of any of the aspects, the microparticle or agent described herein is used as a monotherapy. In another embodiment of any of the aspects, the microparticle or agent described herein can be used in combination with other known agents and therapies (i.e. cotherapies) for a disease, condition, or disorder, such as a disease, condition, or disorder associated with fibrosis. Administered "in combination," as used herein, means that two (or more) different treatments are delivered to the subject during the course of the subject's affliction with the disorder, e.g., the two or more treatments are delivered after the subject has been diagnosed with the disorder (a fibrotic disease or disorder) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The microparticle or agent of this disclosure can be administered before another treatment, concurrently with the treatment, post-treatment, or during remission of the disorder.

When administered in combination, the agent and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of a fibrotic disease or disorder) is lower (e.g., at least 20%, at least 30%, at least 40%, or at least 50% lower) than the amount or dosage of each agent individually required to achieve the same therapeutic effect.

In some embodiments, the cotherapy is a drug, such as aspirin, acetaminophen, non-steroidal anti-inflammatory drugs, steroids, nerve blockers, and analgesic drugs common in the art.

In some embodiments, the cotherapy is a drug for muscular dystrophies, including but not limited to deflazacourt, eteplirsen, casimersen, golodirsen, ataluren, givinostat, viltolarsen, pamrevlumab, SRP-9001, SRP-5051, DS-5141B, SCAAV9.U7.ACCA, PF-06939926, SGT-001, or AT702.

In some embodiments, the cotherapy is a drug for spinal muscular atrophy, including but not limited to Spinraza, Zolgensma, Evrysdi, SRK-015, CK-2127107, LMI070, AVXS-101, BIIB 110, or p38aMAPK inhibitors.

In some embodiments, the cotherapy is a drug for cerebral palsy, stroke, traumatic brain injury, or peripheral nerve injury, including but not limited to anticholinergics such as Benztropine mesylate, Carbidopa-levodopa (Sinemet), Glycopyrrolate (Robinul), Procyclidine hydrochloride (Kemadrin) and Trihexyphenidyl hydrochloride; anticonvulsants such as Gabapentin (Neurontin), Lamotrigine (Lamictal), Oxcarbazepine (Trileptal), Topiramate (Topamax), and Zonisamide (Zonegran); or antispastics i.e. muscle relaxants such as Baclofen, Botulinum toxin, Diazepam (Valium(R)), Dantrolene, Flexeril (Cyclobenzadrine), Dantrium (Dantrolene), or Tizanidine.

In some embodiments, the cotherapy is physical therapy.

In some embodiments, the cotherapy is a surgical intervention, including but not limited to surgical release, capsular release, or surgical repair.

In some embodiments, the cotherapy is an energy-based technique, including but not limited to radiofrequency energy application e.g. radiofrequency ablation, thermal energy application or removal e.g. cryoablation, sonic energy application e.g. ultrasound-based therapeutic techniques, electrical energy application e.g. transcutaneous electrical nerve stimulation (TENs), or other electromagnetic energy application or removal methods such as light exposure.

In some embodiments, the cotherapy is an exoskeleton designed to assist ambulation or other motion in patients with ambulatory or other motion-based dysfunction.

Parenteral Dosage Forms

Parenteral dosage forms of an agents described herein can be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

The phrases "parenteral administration" and "administered parenterally" as used herein means modes of administration other than enteral and topical administration, usually by injection, and includes, without limitation, intravenous, intramuscular, perimuscular, intraarterial, intrathecal, intraventricular, intracapsular, pericapsular, intraorbital, intracardiac, intradermal, peridermal, intraperitoneal, transtracheal, subcutaneous, subcuticular, intraarticular, periarticular, sub capsular, subarachnoid, intraspinal, intracerebro spinal, and intrasternal injection, infusion and other injection or infusion techniques, without limitation. Without limitations, oral administration can be in the form of solutions, suspensions, tablets, pills, capsules, sustained-release formulations, oral rinses, powders and the like. Suitable vehicle solutions that can be used to provide parenteral dosage forms of the invention are well known to those skilled in the art. As used herein, the phrase "vehicle solutions" include, without limitation: sterile water; water for injection USP; saline solution; sodium carboxymethylcellulose; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Efficacy

The efficacy of an agents described herein, e.g., for the treatment of a disease or disorder associated with fibrosis, can be determined by the skilled practitioner. However, a treatment is considered "effective treatment," as the term is used herein, if one or more of the signs or symptoms of the fibrotic disease are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease or disorder, as measured by symptoms of the disease or disorder). Methods of measuring these indicators are known to those of skill in the art and/or are described herein.

Efficacy can be assessed in animal models of a condition described herein, for example, a mouse model or an appropriate animal model of a fibrotic disease or disorder, as the case may be. When using an experimental animal model, efficacy of treatment is evidenced when a statistically significant change in a marker is observed.

In some embodiments, efficacy of treatment includes the minimization of foreign-body-response or immune reaction after administration. For example, the administration of a vehicle control formulation (e.g. a PLGA microparticle containing no therapeutic agent) may elicit macrophage and immune activation as well as inflammation, whereas the administration of a formulation described by the present disclosure may elicit a lower immune response or entirely abrogate the elicited immune response at any point throughout the treatment and assessment after administration.

In some embodiments, foreign body response resulting from administration of a formulation described by the present disclosure may be reduced or abrogated compared to foreign body response resulting from administration of a PLGA microparticle containing a steroid as the therapeutic agent.

The inventions illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present inventions have been specifically disclosed by preferred embodiments and optional features, modification and variation of the concepts herein disclosed may be resorted to by those skilled in the art, and that such modifications and variations are considered to be within the scope of the inventions as defined by the appended embodiments and elsewhere in the invention.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The term "about" as used herein means in quantitative terms plus or minus 10%. For example, "About 3%" would encompass 2.7-3.3% and "About 10%" would encompass 9-11%. Moreover, where "about" is used herein in conjunction with a quantitative term it is understood that in addition to the value plus or minus 10%, the exact value of the quantitative term is also contemplated and described—for example, the term "about 3%" expressly contemplates, describes and includes exactly 3%.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the inventions claimed. Thus, it should be understood that although the present inventions have been specifically disclosed by preferred embodiments and optional features, modification and variation of the inventions embodied therein herein disclosed may be resorted to by those skilled in the art, and that such modifications and variations are considered to be within the scope of various aspects and embodiments of inventions contemplated herein.

Certain aspects and embodiments of the invention and inventions have been described broadly and generically herein. Each of the narrower species and subgeneric groupings falling within the generic invention also form part of some aspects and embodiments of inventions contemplated herein. This includes the generic description of inventions with a proviso or negative limitation removing any subject matter from the genus, regardless of whether or not the excised material is specifically recited herein.

In addition, where features or aspects of the invention are described in terms of Markush groups, those skilled in the art will recognize that some aspects and embodiments of inventions contemplated herein are also thereby described in terms of any individual member or subgroup of members of the Markush group.

While preferred embodiments of the present invention have been shown and described herein, it will be obvious to those skilled in the art that such embodiments are provided by way of example only. Numerous variations, changes, and substitutions will now occur to those skilled in the art without departing from the inventions. It should be understood that various alternatives to the embodiments of the inventions described herein may be employed in practicing the inventions. It is intended that the following embodiments define the scope of the inventions and that methods and structures within the scope of these embodiments and their equivalents be covered thereby.

Unless defined otherwise, all technical and scientific terms used herein have the same meaning as commonly understood by one of ordinary skill in the art to which these inventions belong. Although any methods and materials similar or equivalent to those described herein can be used in the practice or testing of the inventions, it will be understood that modifications and variations are encompassed within the spirit and scope of the instant invention. The preferred methods and materials are now described.

All publications, patents, and patent applications mentioned in this specification are herein incorporated by reference to the same extent as if each individual publication, patent, or patent application was specifically and individually indicated to be incorporated by reference. In the case of conflict, the specification, including definitions, will control.

Some embodiments of the technology described herein can be defined according to any of the following numbered paragraphs:

1. A formulation comprising microparticles comprising an aliphatic polyester and an antifibrotic agent, wherein said microparticles have a diameter of 1-100 μm.
2. A formulation comprising microparticles comprising an aliphatic polyester and an antifibrotic agent, wherein the antifibrotic agent is relaxin and is present in an amount that is 0.01-33% of total mass.
3. A formulation comprising microparticles comprising an aliphatic polyester and an antifibrotic agent, wherein said aliphatic polyester is of molecular weight 10,000-200,000 daltons.
4. A formulation comprising microparticles comprising an aliphatic polyester, a vinyl polymer and an antifibrotic agent.
5. A formulation comprising microparticles comprising an aliphatic polyester, a vinyl polymer and an antifibrotic agent, wherein said microparticles have a diameter of 1-100 μm.
6. A formulation comprising microparticles comprising an aliphatic polyester, a vinyl polymer and an antifibrotic agent, wherein the antifibrotic agent is relaxin and is present in an amount that is 0.01-33% of total mass.
7. A formulation comprising microparticles comprising an aliphatic polyester, a vinyl polymer and an antifibrotic agent, wherein said aliphatic polyester is of molecular weight 10,000-200,000 daltons.
8. A formulation comprising PLGA microparticles comprising an aliphatic polyester and an antifibrotic agent, wherein said microparticles have a diameter of 1-100 μm.
9. A formulation comprising PLGA microparticles comprising an aliphatic polyester and an antifibrotic agent, wherein the antifibrotic agent is relaxin and is present in an amount that is 0.01-33% of total mass.
10. A formulation comprising PLGA microparticles comprising an aliphatic polyester and an antifibrotic agent, wherein said aliphatic polyester is of molecular weight 10,000-200,000 daltons.
11. A formulation comprising PLGA microparticles comprising an aliphatic polyester, a vinyl polymer and an antifibrotic agent, wherein said microparticles have a diameter of 1-50 μm.
12. A formulation comprising PLGA microparticles comprising an aliphatic polyester, a vinyl polymer and an antifibrotic agent, wherein the antifibrotic agent is relaxin and is present in an amount that is 0.1-10% of total mass.
13. A formulation comprising PLGA microparticles comprising an aliphatic polyester, a vinyl polymer and an antifibrotic agent, wherein said aliphatic polyester is of molecular weight 10,000-200,000 daltons.
14. The formulation of any one of the preceding paragraphs, wherein said antifibrotic agent is an agonist of the receptor RXFP1.
15. The formulation of any one of the preceding paragraphs, wherein said antifibrotic agent is human relaxin-2 or an analog or variant.
16. The formulation of any one of the preceding paragraphs, wherein the aliphatic polyester is poly-lactide-co-glycolide.
17. The formulation of any one of the preceding paragraphs, wherein the aliphatic polyester is polycaprolactone.
18. The formulation of any of the preceding paragraphs, wherein said aliphatic polyester is of molecular weight 10,000-200,000 daltons.
19. The formulation of any of the preceding paragraphs, wherein said aliphatic polyester is of molecular weight 10,000-150,000 daltons; or 25,000-125,000 daltons; or 40,00-100,000 daltons.
20. The formulation of any of the preceding paragraphs, wherein said aliphatic polyester is of molecular weight 10,000-30,000 daltons.
21. The formulation of any of the preceding paragraphs, wherein said aliphatic polyester is of molecular weight 30,000-50,000 daltons.
22. The formulation of any of the preceding paragraphs, wherein said aliphatic polyester is of molecular weight 50,000-70,000 daltons.
23. The formulation of any of the preceding paragraphs, wherein said aliphatic polyester is of molecular weight 70,000-90,000 daltons.
24. The formulation of any of the preceding paragraphs, wherein said aliphatic polyester is of molecular weight 90,000-120,000 daltons.
25. The formulation of any of the preceding paragraphs, wherein said aliphatic polyester is of molecular weight 120,000-150,000 daltons.
26. The formulation of any of the preceding paragraphs, wherein said aliphatic polyester is terminated by an ester functional group.
27. The formulation of any of the preceding paragraphs, wherein said aliphatic polyester is terminated by an alkyl-ester functional group.
28. The formulation of any of the preceding paragraphs, wherein said aliphatic polyester is terminated by a carboxylic acid functional group.
29. The formulation of any of the preceding paragraphs, wherein said formulation comprises a vinyl polymer that is poly(vinyl alcohol).
30. The formulation of any of the preceding paragraphs, wherein said formulation comprises a vinyl polymer that is poly(pyrrolidone).
31. The formulation of any of the preceding paragraphs, wherein said formulation comprises a vinyl polymer that is of molecular weight 10,000-200,000 daltons.
32. The formulation of any of the preceding paragraphs, wherein said formulation comprises a vinyl polymer that is of molecular weight molecular weight 10,000-150,000 daltons; or 25,000-125,000 daltons; or 40,00-100,000 daltons.
33. The formulation of any of the preceding paragraphs, wherein said formulation comprises a vinyl polymer that is of molecular weight molecular weight 30,000-50,000 daltons.
34. The formulation of any of the preceding paragraphs, wherein said formulation comprises a vinyl polymer that is of molecular weight molecular weight 50,000-70,000 daltons.
35. The formulation of any of the preceding paragraphs, wherein said formulation comprises a vinyl polymer that is of molecular weight molecular weight 70,000-90,000 daltons.
36. The formulation of any of the preceding paragraphs, wherein said formulation comprises a vinyl polymer that is of molecular weight molecular weight 90,000-120,000 daltons.
37. The formulation of any of the preceding paragraphs, wherein the diameter of said microparticles is 1-100 μm.

38. The formulation of any of the preceding paragraphs, wherein the diameter of said microparticles is 1-75 µm; or 1-50 µm; or 5-50 µm; or 25-50 µm; or 30-50 µm; or 40-50 µm.
39. The formulation of any of the preceding paragraphs, wherein the diameter of said microparticles is 5-10 µm.
40. The formulation of any of the preceding paragraphs, wherein the diameter of said microparticles is 5-8 µm.
41. The formulation of any of the preceding paragraphs, wherein the diameter of said microparticles is 8-12 µm.
42. The formulation of any of the preceding paragraphs, wherein the diameter of said microparticles is 12-18 µm.
43. The formulation of any of the preceding paragraphs, wherein the diameter of said microparticles is 18-25 µm.
44. The formulation of any of the preceding paragraphs, wherein the diameter of said microparticles is 25-35 µm.
45. The formulation of any of the preceding paragraphs, wherein the diameter of said microparticles is 35-45 µm.
46. The formulation of any of the preceding paragraphs, wherein the diameter of said microparticles is 45-50 µm.
47. The formulation of any of the preceding paragraphs, wherein the diameter of said microparticles is about 1 µm.
48. The formulation of any of the preceding paragraphs, wherein the diameter of said microparticles is about 2 µm.
49. The formulation of any of the preceding paragraphs, wherein the diameter of said microparticles is about 3 µm.
50. The formulation of any of the preceding paragraphs, wherein the diameter of said microparticles is about 4 µm.
51. The formulation of any of the preceding paragraphs, wherein the diameter of said microparticles is about 5 µm.
52. The formulation of any of the preceding paragraphs, wherein the diameter of said microparticles is about 6 µm.
53. The formulation of any of the preceding paragraphs, wherein the diameter of said microparticles is about 7 µm.
54. The formulation of any of the preceding paragraphs, wherein the diameter of said microparticles is about 8 µm.
55. The formulation of any of the preceding paragraphs, wherein the diameter of said microparticles is about 9 µm.
56. The formulation of any of the preceding paragraphs, wherein the diameter of said microparticles is about 10 µm.
57. The formulation of any of the preceding paragraphs, wherein the diameter of said microparticles is about 15 µm.
58. The formulation of any of the preceding paragraphs, wherein the diameter of said microparticles is about 20 µm.
59. The formulation of any of the preceding paragraphs, wherein the diameter of said microparticles is about 25 µm.
60. The formulation of any of the preceding paragraphs, wherein the diameter of said microparticles is about 30 µm.
61. The formulation of any of the preceding paragraphs, wherein the diameter of said microparticles is about 35 µm.
62. The formulation of any of the preceding paragraphs, wherein the diameter of said microparticles is about 40 µm.
63. The formulation of any of the preceding paragraphs, wherein the diameter of said microparticles is about 45 µm.
64. The formulation of any of the preceding paragraphs, wherein the diameter of said microparticles is about 50 µm.
65. The formulation of any of the preceding paragraphs, wherein the diameter of said microparticles is about 75 µm.
66. The formulation of any of the preceding paragraphs, wherein the diameter of said microparticles is about 100 µm.
67. The formulation of any of the preceding paragraphs, wherein the diameter of said microparticles is about 150 µm.
68. The formulation of any of the preceding paragraphs, wherein the diameter of said microparticles is about 200 µm.
69. The formulation of any of the preceding paragraphs, wherein said aliphatic polyester is poly-lactide-co-glycolide with a molar ratio of 15:85-25:75, lactide:glycolide.
70. The formulation of any of the preceding paragraphs, wherein said aliphatic polyester is poly-lactide-co-glycolide with a molar ratio of 25:75-35:65, lactide:glycolide.
71. The formulation of any of the preceding paragraphs, wherein said aliphatic polyester is poly-lactide-co-glycolide with a molar ratio of 35:65-45:55, lactide:glycolide.
72. The formulation of any of the preceding paragraphs, wherein said aliphatic polyester is poly-lactide-co-glycolide with a molar ratio of 45:55-55:45, lactide:glycolide.
73. The formulation of any of the preceding paragraphs, wherein said aliphatic polyester is poly-lactide-co-glycolide with a molar ratio of 55:45-65:35, lactide:glycolide.
74. The formulation of any of the preceding paragraphs, wherein said aliphatic polyester is poly-lactide-co-glycolide with a molar ratio of 65:35-75:25, lactide:glycolide.
75. The formulation of any of the preceding paragraphs, wherein said aliphatic polyester is poly-lactide-co-glycolide with a molar ratio of 75:25-85:15, lactide:glycolide.
76. The formulation of any of the preceding paragraphs, wherein said aliphatic polyester is poly-lactide-co-glycolide with a molar ratio of about 50:50, lactide:glycolide.
77. The formulation of any of the preceding paragraphs, wherein said aliphatic polyester is poly-lactide-co-glycolide with a molar ratio of about 45:55, lactide:glycolide.
78. The formulation of any of the preceding paragraphs, wherein said aliphatic polyester is poly-lactide-co-glycolide with a molar ratio of about 55:45, lactide:glycolide.

79. The formulation of any of the preceding paragraphs, wherein said aliphatic polyester is poly-lactide-co-glycolide with a molar ratio of about 40:60, lactide:glycolide.
80. The formulation of any of the preceding paragraphs, wherein said aliphatic polyester is poly-lactide-co-glycolide with a molar ratio of about 60:40, lactide:glycolide. The formulation of any of the preceding paragraphs, wherein the formulation comprises a vinyl polymer that is 0.01-0.1% of total mass.
81. The formulation of any of the preceding paragraphs, wherein the formulation comprises a vinyl polymer that is 0.1-0.3% of total mass.
82. The formulation of any of the preceding paragraphs, wherein the formulation comprises a vinyl polymer that is 0.2-0.9% of total mass.
83. The formulation of any of the preceding paragraphs, wherein the formulation comprises a vinyl polymer that is 0.3-0.7% of total mass.
84. The formulation of any of the preceding paragraphs, wherein the formulation comprises a vinyl polymer that is 0.4-0.6% of total mass.
85. The formulation of any of the preceding paragraphs, wherein the formulation comprises a vinyl polymer that is 0.3-0.6% of total mass.
86. The formulation of any of the preceding paragraphs, wherein the formulation comprises a vinyl polymer that is 0.6-1.0% of total mass.
87. The formulation of any of the preceding paragraphs, wherein the formulation comprises a vinyl polymer that is 1.0-5.0% of total mass.
88. The formulation of any of the preceding paragraphs, wherein the formulation comprises a vinyl polymer that is 5.0-10.0% of total mass.
89. The formulation of any of the preceding paragraphs, wherein the formulation comprises a vinyl polymer that is 10.0-30.0% of total mass.
90. The formulation of any of the preceding paragraphs, wherein the formulation comprises a vinyl polymer that is about 0.1% of total mass.
91. The formulation of any of the preceding paragraphs, wherein the formulation comprises a vinyl polymer that is about 0.2% of total mass.
92. The formulation of any of the preceding paragraphs, wherein the formulation comprises a vinyl polymer that is about 0.3% of total mass.
93. The formulation of any of the preceding paragraphs, wherein the formulation comprises a vinyl polymer that is about 0.4% of total mass.
94. The formulation of any of the preceding paragraphs, wherein the formulation comprises a vinyl polymer that is about 0.5% of total mass.
95. The formulation of any of the preceding paragraphs, wherein the formulation comprises a vinyl polymer that is about 0.6% of total mass.
96. The formulation of any of the preceding paragraphs, wherein the formulation comprises a vinyl polymer that is about 0.7% of total mass.
97. The formulation of any of the preceding paragraphs, wherein the formulation comprises a vinyl polymer that is about 0.8% of total mass.
98. The formulation of any of the preceding paragraphs, wherein the formulation comprises a vinyl polymer that is about 0.9% of total mass.
99. The formulation of any of the preceding paragraphs, wherein the formulation comprises a vinyl polymer that is about 10% of total mass.
100. The formulation of any of the preceding paragraphs, wherein the formulation comprises a vinyl polymer that is about 15% of total mass.
101. The formulation of any of the preceding paragraphs, wherein the formulation comprises a vinyl polymer that is about 20% of total mass.
102. The formulation of any of the preceding paragraphs, wherein the formulation comprises a vinyl polymer that is about 25% of total mass.
103. The formulation of any of the preceding paragraphs, wherein the formulation comprises a vinyl polymer that is about 30% of total mass.
104. The formulation of any of the preceding paragraphs, wherein said antifibrotic agent is 0.005-5% of the total formulation mass.
105. The formulation of any of the preceding paragraphs, wherein said antifibrotic agent is 0.01-10%; 0.01-33%; or 0.1-5% of the total formulation mass; or 0.2-4% of the total formulation mass; or 0.3-3% of the total formulation mass; or 0.5-2% of the total formulation mass; or 0.5-1.5% of the total formulation mass; or 0.5-3% of the total formulation mass; or 1-2% of the total formulation mass; or 1-5% of the total formulation mass; or 3-7% of the total formulation mass; or 5-10% of the total formulation mass.
106. The formulation of any of the preceding paragraphs, wherein said antifibrotic agent is 0.005-0.01% of the total formulation mass.
107. The formulation of any of the preceding paragraphs, wherein said antifibrotic agent is 0.01-0.05% of the total formulation mass.
108. The formulation of any of the preceding paragraphs, wherein said antifibrotic agent is 0.05-0.1% of the total formulation mass.
109. The formulation of any of the preceding paragraphs, wherein said antifibrotic agent is 0.1-0.5% of the total formulation mass.
110. The formulation of any of the preceding paragraphs, wherein said antifibrotic agent is 0.5-1.0% of the total formulation mass.
111. The formulation of any of the preceding paragraphs, wherein said antifibrotic agent is 1.0-2.5% of the total formulation mass.
112. The formulation of any of the preceding paragraphs, wherein said antifibrotic agent is 2.5-5.0% of the total formulation mass.
113. The formulation of any of the preceding paragraphs, wherein said antifibrotic agent is about 0.25% of the total formulation mass.
114. The formulation of any of the preceding paragraphs, wherein said antifibrotic agent is about 0.5% of the total formulation mass.
115. The formulation of any of the preceding paragraphs, wherein said antifibrotic agent is about 0.75% of the total formulation mass.
116. The formulation of any of the preceding paragraphs, wherein said antifibrotic agent is about 1% of the total formulation mass.
117. The formulation of any of the preceding paragraphs, wherein said antifibrotic agent is about 1.25% of the total formulation mass.
118. The formulation of any of the preceding paragraphs, wherein said antifibrotic agent is about 1.5% of the total formulation mass.
119. The formulation of any of the preceding paragraphs, wherein said antifibrotic agent is about 1.75% of the total formulation mass.

120. The formulation of any of the preceding paragraphs, wherein said antifibrotic agent is about 2% of the total formulation mass.
121. The formulation of any of the preceding paragraphs, wherein said antifibrotic agent is about 2.5% of the total formulation mass.
122. The formulation of any of the preceding paragraphs, wherein said antifibrotic agent is about 3% of the total formulation mass.
123. The formulation of any of the preceding paragraphs, wherein said antifibrotic agent is about 5% of the total formulation mass.
124. The formulation of any of the preceding paragraphs, wherein said antifibrotic agent is a relaxin.
125. The formulation of any of the preceding paragraphs, wherein said formulation comprises PLGA microparticles with a PLGA molar ratio that is about 50:50 lactide:glycolide, a relaxin loaded at about 1% by weight of the microparticles, and PVA in a concentration of about 0.5% by weight.
126. The formulation of any of the preceding paragraphs, wherein said formulation comprises PLGA microparticles with a PLGA molar ratio that is about 50:50 lactide:glycolide, a relaxin loaded at about 1% by weight of the microparticles and PVA in a concentration of about 0.0% by weight
127. The formulation of any of the preceding paragraphs, wherein said formulation comprises PLGA microparticles with a PLGA molar ratio that is about 60:40 lactide:glycolide, a relaxin loaded at about 1% by weight of the microparticles, and PVA in a concentration of about 0.5% by weight.
128. The formulation of any of the preceding paragraphs, wherein said formulation comprises PLGA microparticles with a PLGA molar ratio that is 40:60 lactide:glycolide, a relaxin loaded at about 1% by weight of the microparticles, and PVA in a concentration of about 0.5% by weight.
129. The formulation of any of the preceding paragraphs; wherein said formulation comprises microparticles suspended in a vehicle solution.
130. The formulation of any of the preceding paragraphs; wherein said formulation comprises microparticles suspended in a sodium chloride liquid solution.
131. The formulation of any of the preceding paragraphs; wherein said formulation comprises microparticles suspended in a sodium chloride liquid solution; wherein said sodium chloride is 0.5-1.5 w/w %; or between 0.75-1.25 w/w %; or about 0.5 w/w %; or about 0.6 w/w %; or about 0.7 w/w %; or about 0.8 w/w %; or about 0.9 w/w %; or about 1.0 w/w %; or about 1.1 w/w %; or about 1.2 w/w %; or about 1.3 w/w %; or about 1.4 w/w %; or about 1.5 w/w % of the liquid solution.
132. The formulation of any of the preceding paragraphs; wherein said formulation comprises microparticles suspended in a sodium carboxymethylcellulose solution.
133. The formulation of any of the preceding paragraphs; wherein said formulation comprises microparticles suspended in a sodium carboxymethylcellulose solution; wherein said sodium carboxymethylcellulose solution is 0.1-1.0 w/w %; or between 0.25-0.75 w/w %; or about 0.1 w/w %; or about 0.2 w/w %; or about 0.3 w/w %; or about 0.4 w/w %; or about 0.5 w/w %; or about 0.6 w/w %; or about 0.7 w/w %; or about 0.8 w/w %; or about 0.9 w/w %; or about 1.0 w/w % of the liquid solution.
134. The formulation of any of the preceding paragraphs, wherein said formulation is a sustained release formulation.
135. The formulation of any of the preceding paragraphs, wherein said formulation is a sustained release formulation wherein the antifibrotic agent is released over an extended period of time.
136. The formulation of any of the preceding paragraphs, wherein said formulation is a sustained release formulation wherein the antifibrotic agent is released over an extended period of least 1 day; or at least 2 days; or at least 3 days; or at least 4 days; or at least 5 days; or at least 6 days; or at least 1 week; or at least 2 weeks; or at least 3 weeks; or at least 4 weeks; or at least 5 weeks, or at least 6 weeks; or at least 8 weeks; or at least 9 weeks; at least 10 weeks; or at least 12 weeks; or at least 15 weeks; or between 1-5 days; or between 2-5 days; or between 1-2 days; or between 2-3 days; or between 3-4 days; or between 4-5 days; or between 3-10 days; or between 1-15 weeks; or between 2-10 weeks; or between 4-8 weeks; or between 8-15 weeks; or about 1 day; or about 2 days; or about 3 days; or about 4 days; or about 5 days; or about 6 days; or about 1 week; or about 2 weeks; or about 3 weeks; or about 4 weeks; or about 5 weeks; or about 6 weeks; or about 7 weeks; or about 8 weeks; or about 9 weeks; or about 10 weeks, or more.
137. A method, said method comprising identifying a subject diagnosed with one or more diseases selected from the group of diseases listed in Table 1 or Table 2 and administering a formulation of any one of the preceding paragraphs to the subject.
138. A method, said method comprising identifying a subject diagnosed with Duchenne Muscular Dystrophy and administering to said patient a composition or formulation of any of the preceding paragraphs.
139. A method, said method comprising identifying a subject diagnosed with Becker Muscular Dystrophy and administering to said patient a composition or formulation of any of the preceding paragraphs.
140. A method, said method comprising identifying a subject diagnosed with Spinal Muscular Atrophy, Type I, and administering to said patient a composition or formulation of any of the preceding paragraphs.
141. A method, said method comprising identifying a subject diagnosed with Spinal Muscular Atrophy, Type II, and administering to said patient a composition or formulation of any of the preceding paragraphs.
142. A method, said method comprising identifying a subject diagnosed with Spinal Muscular Atrophy, Type III, and administering to said patient a composition or formulation of any of the preceding paragraphs.
143. A method, said method comprising identifying a subject diagnosed with Spinal Muscular Atrophy, Type IV, and administering to said patient a composition or formulation of any of the preceding paragraphs.
144. A method, said method comprising identifying a subject diagnosed with Cerebral Palsy, Stroke, Traumatic Brain Injury, and/or peripheral nerve damage, and administering to said patient a composition or formulation of any of the preceding paragraphs.
145. A method, said method comprising identifying a subject diagnosed with Arthrogryposis Multiplex Congenita and administering to said patient a composition or formulation of any of the preceding paragraphs.
146. A method, said method comprising identifying a subject with fibrosis of the humeroradial joint and administering to said patient a composition or formulation of any of the preceding paragraphs.
147. A method, said method comprising identifying a subject with fibrosis of the humeroulnar joint and administering to said patient a composition or formulation of any of the preceding paragraphs.
148. A method, said method comprising identifying a subject with fibrosis of the glenohumeral joint and administering to said patient a composition or formulation of any of the preceding paragraphs.
149. A method, said method comprising identifying a subject with fibrosis of the tibiofemoral joint and administering to said patient a composition or formulation of any of the preceding paragraphs.
150. A method, said method comprising identifying a subject with fibrosis of the acetabulofemoral joint and administering to said patient a composition or formulation of any of the preceding paragraphs.
151. A method, said method comprising identifying a subject with fibrosis of the talocrural joint and administering to said patient a composition or formulation of any of the preceding paragraphs.
152. A method, said method comprising identifying a subject with fibrosis of the temporomandibular joint and administering to said patient a composition or formulation of any of the preceding paragraphs.
153. A method, said method comprising identifying a subject with fibrosis of the metacarpophalangeal joint and administering to said patient a composition or formulation of any of the preceding paragraphs.
154. A method, said method comprising identifying a subject with fibrosis of the metatarsophalangeal joint and administering to said patient a composition or formulation of any of the preceding paragraphs.
155. A method, said method comprising identifying a subject with fibrosis of the peri-articular musculature and administering to said patient a composition or formulation of any of the preceding paragraphs.
156. A method, said method comprising identifying a subject with cellulite and administering to said patient a composition or formulation of any of the preceding paragraphs.
157. A method, said method comprising identifying a subject with interstitial lung disease and administering to said patient a composition or formulation of any of the preceding paragraphs.
158. A method, said method comprising administering, to any of the preceding subjects, a composition or formulation of any of the preceding paragraphs, via inhalation as an aerosol.
159. A method, said method comprising administering, to any of the preceding subjects, a composition or formulation of any of the preceding paragraphs, via intraarticular injection.
160. A method, said method comprising administering, to any of the preceding subjects, a composition or formulation of any of the preceding paragraphs, via intramuscular injection.
161. A method, said method comprising administering, to any of the preceding subjects, a composition or formulation of any of the preceding paragraphs, via intradermal injection.
162. A method, said method comprising administering, to any of the preceding subjects, a composition or formulation of any of the preceding paragraphs, via subcutaneous injection.
163. A method, said method comprising administering, to any of the preceding subjects, a composition or formulation of any of the preceding paragraphs, via intracapsular injection.
164. A method, said method comprising administering, to any of the preceding subjects, a composition or formulation of any of the preceding paragraphs, via pericapsular injection.
165. A method, said method comprising administering, to any of the preceding subjects, a composition or formulation of any of the preceding paragraphs, via intraligamentous injection.
166. A method, said method comprising administering, to any of the preceding subjects, a composition or formulation of any of the preceding paragraphs, via periligamentous injection.
167. A method, said method comprising administering, to any of the preceding subjects, a composition or formulation of any of the preceding paragraphs, via intratendinous injection.
168. A method, said method comprising administering, to any of the preceding subjects, a composition or formulation of any of the preceding paragraphs, via peritendinous injection.
169. A method, said method comprising administering, to any of the preceding subjects, a composition or formulation of any of the preceding paragraphs, via intraosteotendinous injection.
170. A method, said method comprising administering, to any of the preceding subjects, a composition or formulation of any of the preceding paragraphs, via periosteotendinous injection.
171. A method, said method comprising administering, to a subject diagnosed with Duchene's muscular dystrophy, a composition or formulation of any of the preceding paragraphs, via intramuscular injection.
172. A method, said method comprising administering, to a subject diagnosed with Duchene's muscular dystrophy, a composition or formulation of any of the preceding paragraphs, via intraarticular injection.
173. A method, said method comprising administering, to a subject diagnosed with Becker's muscular dystrophy, a composition or formulation of any of the preceding paragraphs, via intramuscular injection.
174. A method, said method comprising administering, to a subject diagnosed with Becker's muscular dystrophy, a composition or formulation of any of the preceding paragraphs, via intraarticular injection
175. A method, said method comprising administering, to a subject diagnosed with Spinal Muscular Dystrophy, a composition or formulation of any of the preceding paragraphs, via intramuscular injection.
176. A method, said method comprising administering, to a subject diagnosed with Spinal Muscular Dystrophy, a composition or formulation of any of the preceding paragraphs, via intraarticular injection.
177. A method, said method comprising administering, to a subject diagnosed with Arthrogryposis Multiplex Congenita, a composition or formulation of any of the preceding paragraphs, via intramuscular injection.
178. A method, said method comprising administering, to a subject diagnosed with Arthrogryposis Multiplex Congenita, a composition or formulation of any of the preceding paragraphs, via intraarticular injection.

179. A method, said method comprising administering, to a subject diagnosed with Cerebral Palsy, a composition or formulation of any of the preceding paragraphs, via intramuscular injection.

180. A method, said method comprising administering, to a subject diagnosed with Cerebral Palsy, a composition or formulation of any of the preceding paragraphs, via intraarticular injection.

181. A method, said method comprising administering, to a subject diagnosed with stroke, a composition or formulation of any of the preceding paragraphs, via intramuscular injection.

182. A method, said method comprising administering, to a subject diagnosed with stroke, a composition or formulation of any of the preceding paragraphs, via intraarticular injection.

183. A method, said method comprising administering, to a subject diagnosed with traumatic brain injury, a composition or formulation of any of the preceding paragraphs, via intramuscular injection.

184. A method, said method comprising administering, to a subject diagnosed with traumatic brain injury, a composition or formulation of any of the preceding paragraphs, via intraarticular injection.

185. A method, said method comprising administering, to a subject diagnosed with peripheral nerve damage, a composition or formulation of any of the preceding paragraphs, via intramuscular injection.

186. A method, said method comprising administering, to a subject diagnosed with peripheral nerve damage, a composition or formulation of any of the preceding paragraphs, via intraarticular injection.

187. A method, said method comprising administering any of the preceding paragraphs with sizes between 1 um-10 μm via inhalation as an aerosol.

188. A method, said method comprising administering any of the preceding paragraphs with sizes between 20 um-100 μm via intramuscular injection.

189. A method, said method comprising administering any of the preceding paragraphs with sizes between 5 um-50 μum via intraarticular injection.

190. A method, said method comprising administering, to a subject diagnosed with interstitial lung disease any of the preceding paragraphs via inhalation as an aerosol.

191. A method, said method comprising administering, to a subject diagnosed with interstitial lung disease any of the preceding paragraphs via inhalation as an aerosol.

192. A method, said method comprising administering, to a subject diagnosed with interstitial lung disease any of the preceding paragraphs, wherein the diameter of the microparticle is 1-10 μm, via inhalation as an aerosol.

193. A method, said method comprising administering, to a subject diagnosed with Duchene's Muscular Dystrophy any of the preceding paragraphs, wherein the diameter of the microparticle is 10-30 μm, via intraarticular injection.

194. A method, said method comprising administering, to a subject diagnosed with Duchene's Muscular Dystrophy any of the preceding paragraphs, wherein the diameter of the microparticle is 25-50 μm, via intraarticular injection.

195. A method, said method comprising administering, to a subject diagnosed with Duchene's Muscular Dystrophy any of the preceding paragraphs, wherein the diameter of the microparticle is 10-30 μm, via intramuscular injection.

196. A method, said method comprising administering, to a subject diagnosed with Duchene's Muscular Dystrophy any of the preceding paragraphs, wherein the diameter of the microparticle is 25-50 μm, via intramuscular injection.

197. A method, said method comprising administering, to a subject diagnosed with Spinal Muscular Atrophy any of the preceding paragraphs, wherein the diameter of the microparticle is 10-30 μm, via intraarticular injection.

198. A method, said method comprising administering, to a subject diagnosed with Spinal Muscular Atrophy any of the preceding paragraphs, wherein the diameter of the microparticle is 25-50 μm, via intraarticular injection.

199. A method, said method comprising administering, to a subject diagnosed with Spinal Muscular Atrophy any of the preceding paragraphs, wherein the diameter of the microparticle is 10-30 μm, via intramuscular injection.

200. A method, said method comprising administering, to a subject diagnosed with Spinal Muscular Atrophy any of the preceding paragraphs, wherein the diameter of the microparticle is 25-50 μm, via intramuscular injection.

201. A method, said method comprising administering, to a subject diagnosed with joint arthrofibrosis any of the preceding paragraphs, wherein the diameter of the microparticle is 10-30 μm, via intraarticular injection.

202. A method, said method comprising administering, to a subject diagnosed with joint arthrofibrosis any of the preceding paragraphs, wherein the diameter of the microparticle is 25-50 μm, via intraarticular injection.

203. A method or formulation of any of the preceding paragraphs, wherein the formulation is delivered via inhalation as an aerosol.

204. A method or formulation of any of the preceding paragraphs, wherein the formulation is delivered via intra-articular injection.
205. A method or formulation of any of the preceding paragraphs, wherein the formulation is delivered via intramuscular injection.
206. The method or formulation of any one of the preceding paragraphs wherein, the formulation is administered to the subject such that the antifibrotic agent (e.g., a relaxin) is administered to a subject at a dose between 1-2000 μg/kg body weight; or between 10-100 μg/kg body weight; or between 100-200 μg/kg body weight; or between 200-500 μg/kg body weight; or between 500-1000 μg/kg body weight; or 25-75 μg/kg body weight; or 30-70 μg/kg body weight; or 40-60 μg/kg body weight; or between 1-10 μg/kg body weight; or between 1-5 μg/kg body weight; or between 4-8 μg/kg body weight; or about 2 μg/kg body weight; or about 5 μg/kg body weight; or about 10 μg/kg body weight; or about 20 μg/kg body weight; or about 25 μg/kg body weight; or about 30 μg/kg body weight; or about 35 μg/kg body weight; or about 40 μg/kg body weight; or about 45 μg/kg body weight; or about 50 μg/kg body weight; or about 55 μg/kg body weight; or about 60 μg/kg body weight; or about 65 μg/kg body weight; or about 70 μg/kg body weight; or about 75 μg/kg body weight; or about 100 μg/kg body weight; or about 200 μg/kg body weight; or about 500 μg/kg body weight.

207. The method or formulation of any one of the preceding paragraphs, wherein the formulation is administered one time.
208. The method or formulation of any one of the preceding paragraphs, wherein the formulation is administered more than one time.
209. The method or formulation of any one of the preceding paragraphs, wherein the formulation is administered once per week.
210. The method or formulation of any one of the preceding paragraphs, wherein the formulation is administered once every 2 weeks.
211. The method or formulation of any one of the preceding paragraphs, wherein the formulation is administered once every 3 weeks.
212. The method or formulation of any one of the preceding paragraphs, wherein the formulation is administered once every 4 weeks.
213. The method or formulation of any one of the preceding paragraphs, wherein the formulation is administered once every 6 weeks.
214. The method or formulation of any one of the preceding paragraphs, wherein the formulation is administered once every 8 weeks.
215. The method or formulation of any one of the preceding paragraphs, wherein the formulation is administered once every 10 weeks.
216. The method or formulation of any one of the preceding paragraphs, wherein the formulation is administered once every 12 weeks.
217. The method or formulation of any one of the preceding paragraphs, wherein the formulation is administered once every 16 weeks.
218. The method or formulation of any one of the preceding paragraphs, wherein the formulation is administered once every 20 weeks.
219. The method or formulation of any one of the preceding paragraphs, wherein the formulation is administered once every 24-26 weeks.
220. The method or formulation of any one of the preceding paragraphs, wherein the formulation is administered once every 8 months.
221. The method or formulation of any one of the preceding paragraphs, wherein the formulation is administered once every 9 months.
222. The method or formulation of any one of the preceding paragraphs, wherein the formulation is administered once every 12 months.
223. The method or formulation of any one of the preceding paragraphs, wherein the antifibrotic agent is released from the microparticle with a linear release profile.
224. The method or formulation of any one of the preceding paragraphs, wherein the antifibrotic agent is released from the microparticle with a non-linear release profile.
225. The method or formulation of any one of the preceding paragraphs, wherein the antifibrotic agent is released from the microparticle with an initial bolus in its release profile.
226. The method or formulation of any one of the preceding paragraphs, wherein the antifibrotic agent is released from the microparticle without an initial bolus in its release profile.
227. The method or formulation of any one of the preceding paragraphs, wherein the antifibrotic agent is released from the microparticle with a burst-release in its release profile after the first several days.
228. The method or formulation of any one of the preceding paragraphs, wherein the antifibrotic agent is released from the microparticle with no burst-release in its release profile.

Some embodiments of the technology described herein can be defined according to any of the following additional numbered paragraphs:

1. A method of treating a fibrotic disease, the method comprising administering to a subject in need thereof an agent that binds a relaxin family peptide receptor.
2. The method of any preceding paragraphs, wherein the relaxin family peptide receptor is RXFP1, RXFP2, RXFP3, or RXFP4.
3. The method of any preceding paragraphs, wherein the agent is a native ligand of the receptor.
4. The method of any preceding paragraphs, wherein the native ligand is Relaxin-2 or a Relaxin-2 variant.
5. The method of any preceding paragraphs, wherein the Relaxin-2 variant is at least 85%, at least 90%, at least 95% or at least 99% similar to native Relaxin-2.
6. The method of any preceding paragraphs, wherein the agent is recombinantly produced in a bacterial, mammalian or yeast host cell.
7. The method of any preceding paragraphs, wherein the agent is fully or partially chemically synthesized.
8. The method of any preceding paragraphs, wherein the agent is conjugated to a targeting moiety.
9. The method of any preceding paragraphs, wherein the targeting moiety is selected from the group consisting of a single-domain camelid antibody fragment, a peptide sequence, polynucleotide, or a small molecule, or a small molecule allosteric modulator.
10. The method of any preceding paragraphs, wherein the agent is comprised in a depot.
11. The method of any preceding paragraphs, wherein the depot has at least one of
    a. a volume of 0.1 um$^3$;
    b. is comprised of one or more polymer; or
    c. is comprised of one or more self-assembled small molecule.
12. The method of any preceding paragraphs, wherein the depot has a diameter of 1-100 μm.
13. The method of any preceding paragraphs, wherein the depot is comprised of a hydrogel comprised of low molecular weight gelators.
14. The method of any preceding paragraphs, wherein depot is comprised of poly(lactic-co-glycolic acid).
15. The method any preceding paragraphs, wherein the depot is comprised of a crosslinked hydrogel comprised of polyethyelene glycol.
16. The method of any preceding paragraphs, wherein the depot is comprised of a self-assembled amphiphilic hydrogel comprised of amphiphilic small molecules.
17. The method of any preceding paragraphs, wherein the fibrotic disease is selected from the group consisting of stiffened fibrotic joint capsules, lung fibrosis (i.e. idiopathic pulmonary fibrosis, cystic fibrosis, hypertension), liver fibrosis (i.e. hepatitis B or C, long-term alcohol abuse, non-alcoholic steatohepatitis, non-alcoholic fatty liver disease, Cholestasis, autoimmune hepatitis cirrhosis), kidney fibrosis (i.e. chronic kidney disease, end-stage renal disease, renal interstitial fibrosis), heart disease (i.e. heart failure, myocardial infarction, aortic stenosis, hypertrophic cardiomyopathy), intestinal disease (i.e. Crohn's disease, inflammatory bowel disease, enteropathies, and other intestinal fibrosis), skin conditions (i.e. scleroderma, keloids, hypertrophic scars, cellulite), urogenital and gynecological conditions (Peyronie's disease, uterine fibroids) and ocular diseases (i.e. Congenital Fibrosis of the Extraocular Muscles, subretinal fibrosis, epiretinal fibrosis, corneal fibrosis).

18. The method of any preceding paragraphs, wherein the agent is administered locally to a target organ.
19. The method of any preceding paragraphs, wherein the agent is administered systemically.
20. The method of any preceding paragraphs, wherein the agent is administered via intraarticular, periarticular, intracapsular, pericapsular, intraligamentous, periligamentous, intratendinous, peritendinous, intraosteotendinous, or periosteotendinous injection, intramuscularly, subcutaneously, intradermally, intranasally, orally, transcutaneously, mucosally, transcutaneously, or by pulmonary inhalation.
21. The method of any preceding paragraphs, wherein administration is under fluoroscopic or ultrasound guidance.
22. The method of any preceding paragraphs, wherein the target organ is a lung, kidney, liver, heart, skin or eye.
23. The method of any preceding paragraphs, wherein the subject is further administered at least a second therapeutic.
24. The method of any preceding paragraphs, wherein the at least a second therapeutic is physical therapy.
25. The method of any preceding paragraphs, wherein the at least a second therapeutic is a surgery.
26. The method of any preceding paragraphs, comprising a step, prior to administering, of diagnosing a subject as having a fibrotic disease.
27. The method of any preceding paragraphs, comprising a step, prior to administering, of receiving a results of an assay that diagnoses a subject as having a fibrotic disease.
28. A method of treating a fibrotic disease, the method comprising administering to a subject in need thereof an agent that binds a relaxin family peptide receptor, wherein the agent is comprised in a depot for sustained release.
29. A composition comprising an agent that binds a relaxin family peptide receptor.
30. The composition of any preceding paragraphs, wherein the relaxin family peptide receptor is RXFP1, RXFP2, RXFP3, or RXFP4.
31. The composition of any preceding paragraphs, wherein the agent is a native ligand of the receptor.
32. The composition of any preceding paragraphs, wherein the native ligand is Relaxin-2 or a Relaxin-2 variant.
33. The composition of any preceding paragraphs, wherein the Relaxin-2 variant is at least 85%, at least 90%, at least 95% or at least 99% similar to native Relaxin-2.
34. The composition of any preceding paragraphs, wherein the agent is recombinantly produced in a bacterial, mammalian or yeast host cell.
35. The composition of any preceding paragraphs, wherein the agent is fully or partially chemically synthesized.
36. The composition of any preceding paragraphs, wherein the agent is conjugated to a targeting moiety.
37. The composition of any preceding paragraphs, wherein the targeting moiety is selected from the group consisting of a single-domain camelid antibody fragment, a peptide sequence, polynucleotide, or a small molecule, or a small molecule allosteric modulator.
38. The composition of any preceding paragraphs, wherein the agent is comprised in a depot.
39. The composition of any preceding paragraphs, wherein the depot has at least one of
   a. a volume of 0.1 um$^3$;
   b. is comprised of one or more polymer; or
   c. is comprised of one or more self-assembled small molecule.
40. The composition of any preceding paragraphs, wherein the depot has a diameter of 1-100 m.
41. The composition of any preceding paragraphs, wherein the depot is comprised of a hydrogel comprised of low molecular weight gelators.
42. The composition of any preceding paragraphs, wherein depot is comprised of poly(lactic-co-glycolic acid).
43. The composition of any preceding paragraphs, wherein the depot is comprised of a crosslinked hydrogel comprised of polyethyelene glycol.
44. The composition of any preceding paragraphs, wherein the depot is comprised of a self-assembled amphiphilic hydrogel comprised of amphiphilic small molecules
45. Use of a composition of any preceding paragraphs, for treatment of a fibrotic disease.

EXAMPLES

The present invention will be further described in the following examples, which do not limit the scope of the present invention.

Figure 2:
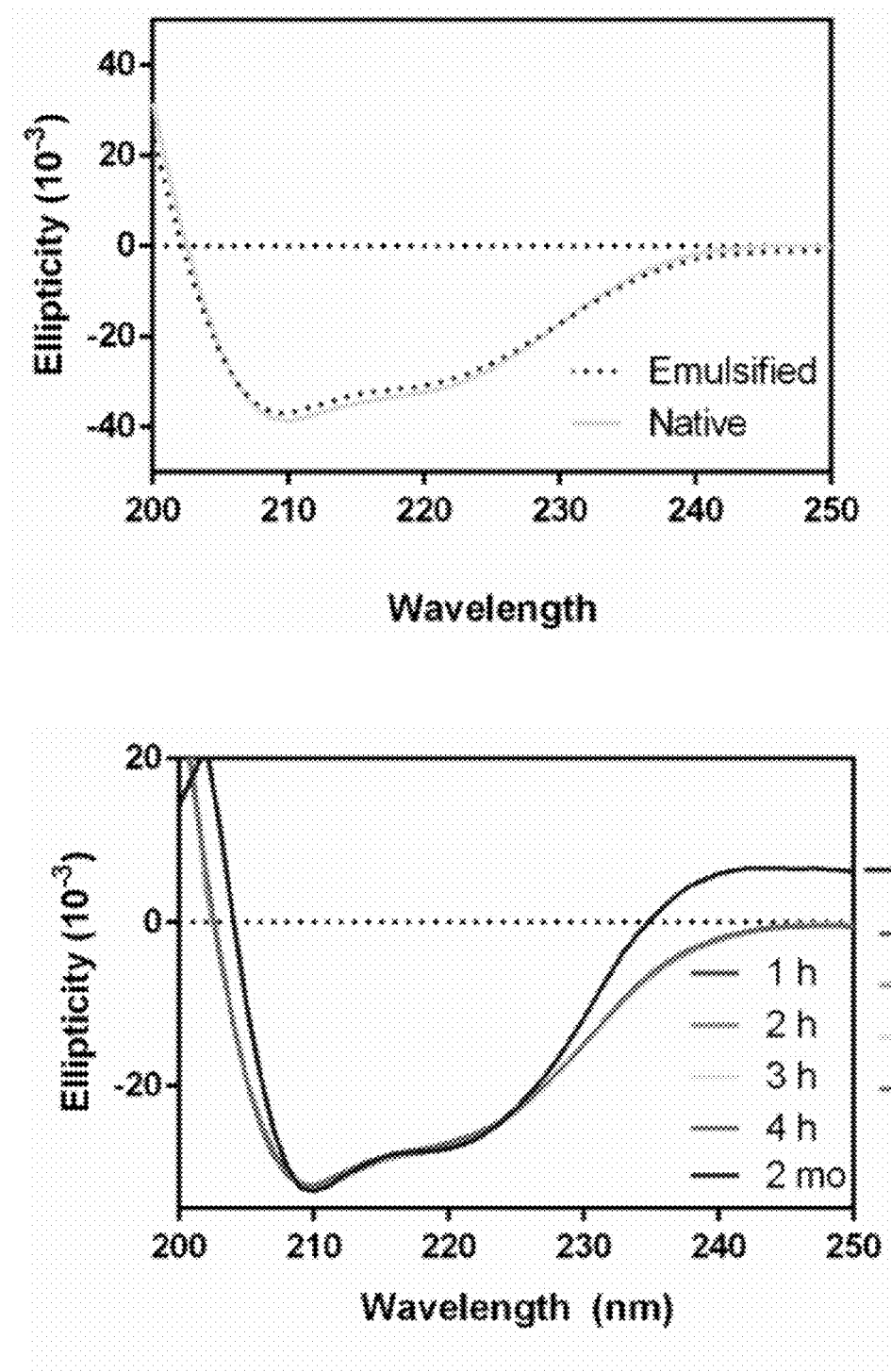
FIG. 2 shows relaxin-2 maintains its fold and stability during encapsulation and release at physiological temperature. (left) Circular dichroism spectroscopy indicates that relaxin-2 is unaffected by the double emulsion process and is able to maintain its secondary alpha helical structure during PLGA microparticle synthesis. (right) Relaxin-2 is stable at 37° C. for up to 2 months without any loss of alpha helical structure. 1-4 h spectra are all overlaid.

Example 1. Synthesis, Characterization, and Evaluation of Relaxin-2-Loaded Microparticles Relaxin-2 loaded PLGA microparticles (RMPs) were prepared based on the water/oil/water (w/o/w) method as described by Igartua, M., et. al., International Journal of Pharmaceutics, 1998, 169(1): 45-54 at 1.27×10-3 wt % loaded relaxin as determined by ELISA analysis. Significant optimization and tailoring of the method was required to obtain the particle. Amounts, time, temperature, mixing speed, polymer LA:GA content were all varied to identify a unique non-obvious set of conditions to prepare the polymer. An ELISA analysis also revealed an encapsulation efficiency of 90-95%. Dynamic light scattering (DLS) showed the particles to be 7.65 µm in diameter with a small polydispersity and spherical shape by SEM. Relaxin-2 in the relaxin-2 microparticles maintained its native secondary and tertiary structure through the w/o/w double-emulsion process. Circular dichroism spectra showed no change between freshly prepared and emulsified relaxin-2 (FIG. 2, left). Additionally, relaxin-2 was stable at 37° C. over 2 months (FIG. 2, right). The relaxin-2 PLGA microparticles were prepared with batch-to-batch consistency and were resuspended in PEG-600 to reduce aggregation and flocculation, as well as to ease administration through a 23 G needle.

Relaxin-2 microparticles are prepared by spray drying. A rotary wheel atomizer spinning at 15,000RPM with peripheral exit speeds of 250 m/sec and an air flow rate of 40 m/sec produces 35 µm relaxin-2 microparticles. The feed solution comprises an emulsion of relaxin-2 (1 mg/ml in $H_2O$) and PL:GA (molar ratio 45:65 lactide:glycolide, M.W. 50,000-75,000 daltons, carboxylic acid terminated, 50 mg/ml in methylene chloride).

Relaxin-2 microparticles are prepared by solvent extraction. An emulsion of relaxin-2 (0.5 mg/ml) and PL:GA (molar ratio 50:50 lactide:glycolide, M.W. 70,000-90,000 daltons, ester terminated, 50 mg/ml) is formed in ethyl acetate. 1% by volume poly-vinyl alcohol (M.W. 30,000 dalton) is added to the rapidly mixing emulsion and then the remaining solvent is removed by evaporation. Prior to lyophilization, the relaxin-2 microparticles are 48 μm in diameter.

Figure 3:
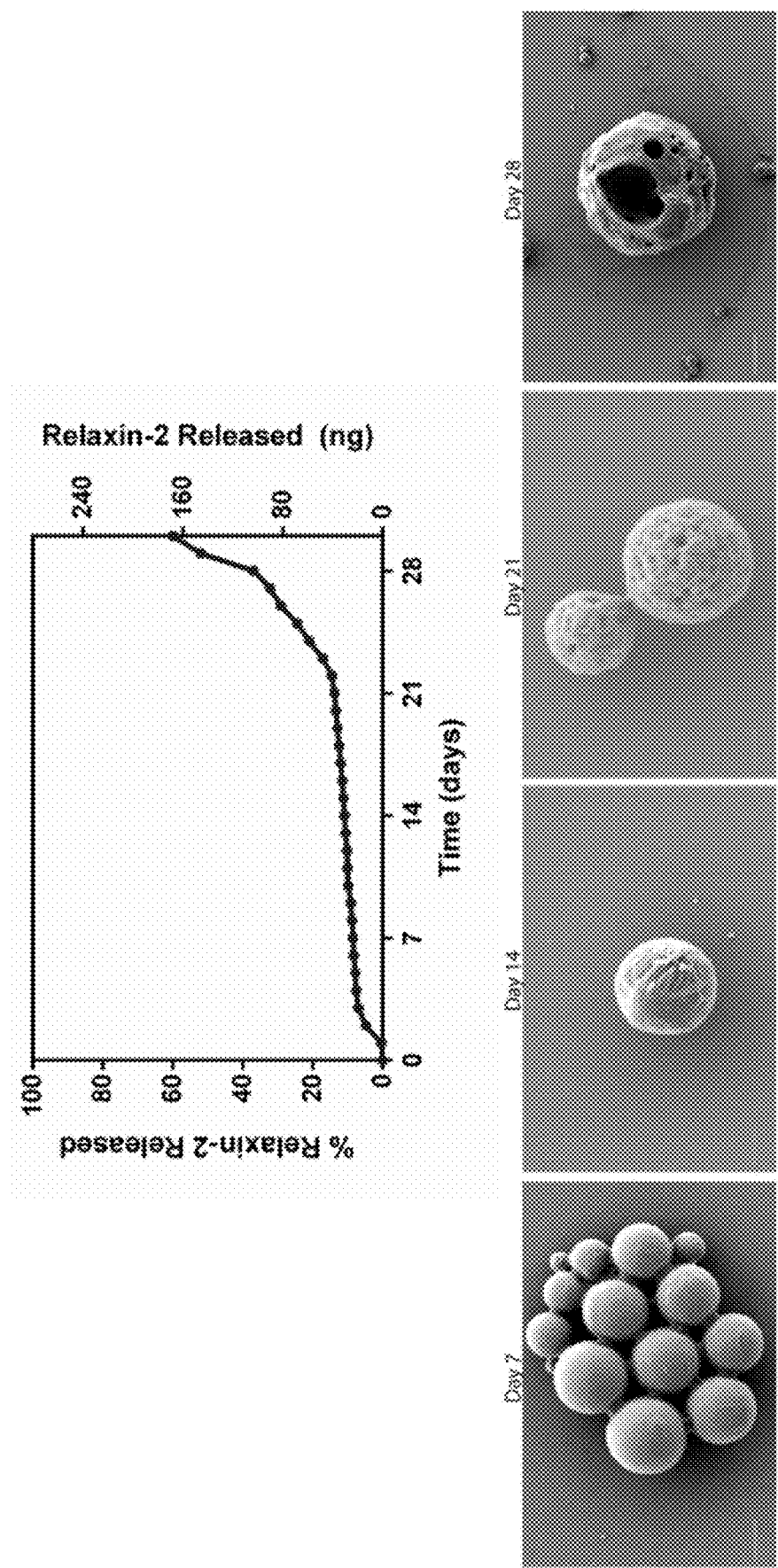
FIG. 3 shows encapsulation within PLGA microparticles allows for the sustained release of relaxin-2. (top) Over the course of 30 days, the relaxin-2-loaded PLGA microparticles release 60% of the initial relaxin-2. The release is slow in the first three weeks and increases rapidly after three weeks. (bottom) The microparticles degrade over time. Beginning after two weeks, the smooth surface of the particles is lost as hydrolysis occurs on the polymeric surface. After 4 weeks, the particles become porous, which account for the increase in release rate of relaxin-2. Scale bar=2 μm.

The release of relaxin-2 from the microparticles was quantified via a relaxin-2 ELISA. The concentration of relaxin-2 in a reservoir of biologically relevant buffer meant to mimic synovial fluid (Dublecco's Modified Eagle Media+20% heat inactivated fetal bovine serum+25 μg/ml porcine esterase+1% penicillin streptomycin) was determined every three days over the course of 60 days. After 28 days, 85% of the initial encapsulated relaxin-2 was released from the particles (FIG. 3, top). Release occurs at a semi-linear rate for the first four weeks (FIG. 3, top). SEM image analysis of relaxin-2 microparticles at various time points showed that into the 3rd week, the relaxin microparticles degrade via bulk erosion. At the 5$^{th}$ and 6$^{th}$ week, the relaxin-2 microparticles displayed near complete degradation with high porosity and me to degrade as the smooth surface is lost and becomes wrinkled. By the fourth week, the RMPs are significantly degraded as indicated by their substantial increase in porosity compared to when initially prepared (FIG. 3, bottom).

Figure 4:
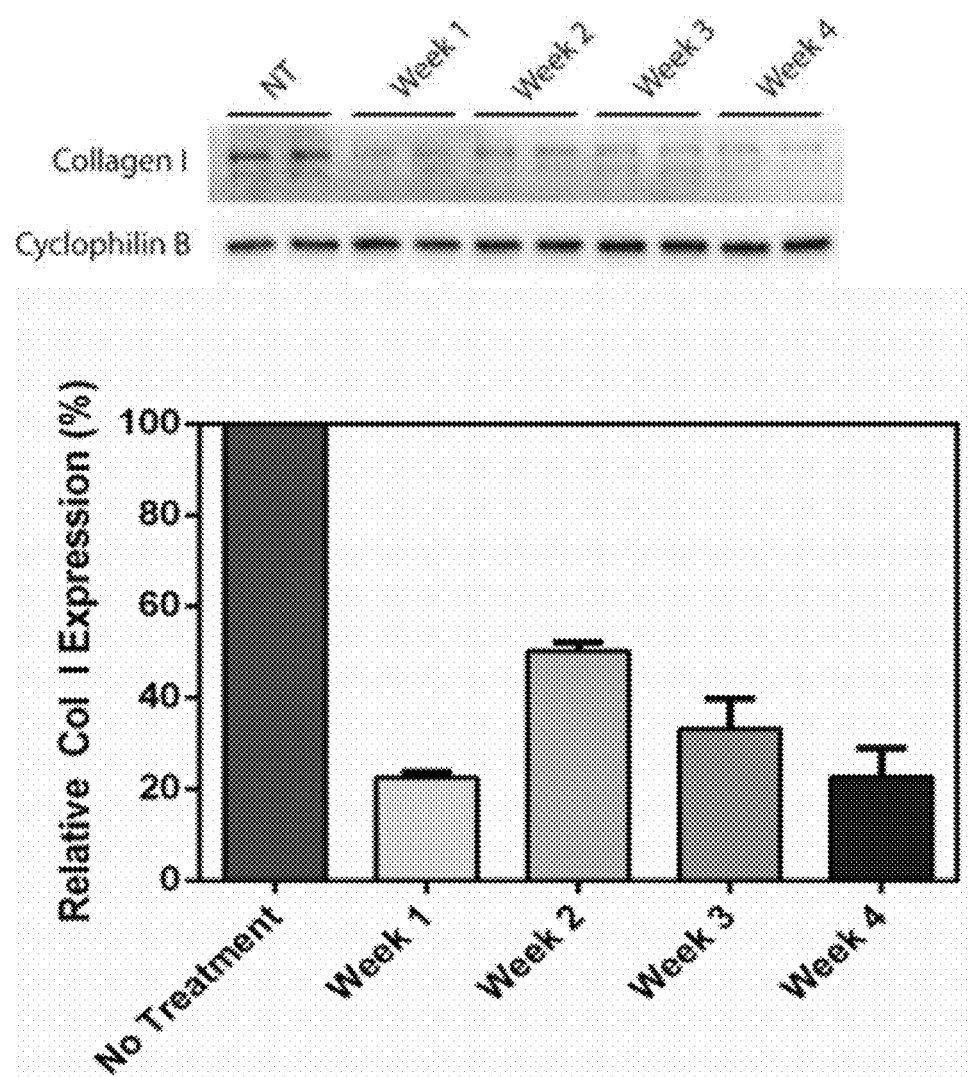
FIG. 4 shows relaxin-2 is released in vitro for up to four weeks and is able to decrease collagen expression. (top) Over the course of four weeks, the relaxin-2 was released at an effective dose as noted by the significant downregulation in collagen I expression compared to the untreated control in synoviocytes. (bottom) Densitometry reveals that collagen I is reduced to approximately 50% after the release of relaxin-2.

Human fibroblast-like synoviocytes (HFLS) treated with relaxin-2 microparticles in transwells allow for evaluation of the release and efficacy of released relaxin-2 at various time points. Relaxin-2 released from relaxin-2 microparticles demonstrated antifibrotic efficacy for up to four weeks as indicated by the downregulation of collagen I expression in the presence of 5 ng/mL TGFβ-1 (FIG. 4, top). In the presence of relaxin-2, collagen I is expressed at 20 to 30% of the basal level at weeks 1, 3, and 4. The 2-week time point displayed 50% downregulation of collagen expression (FIG. 4, bottom).

Figure 5:
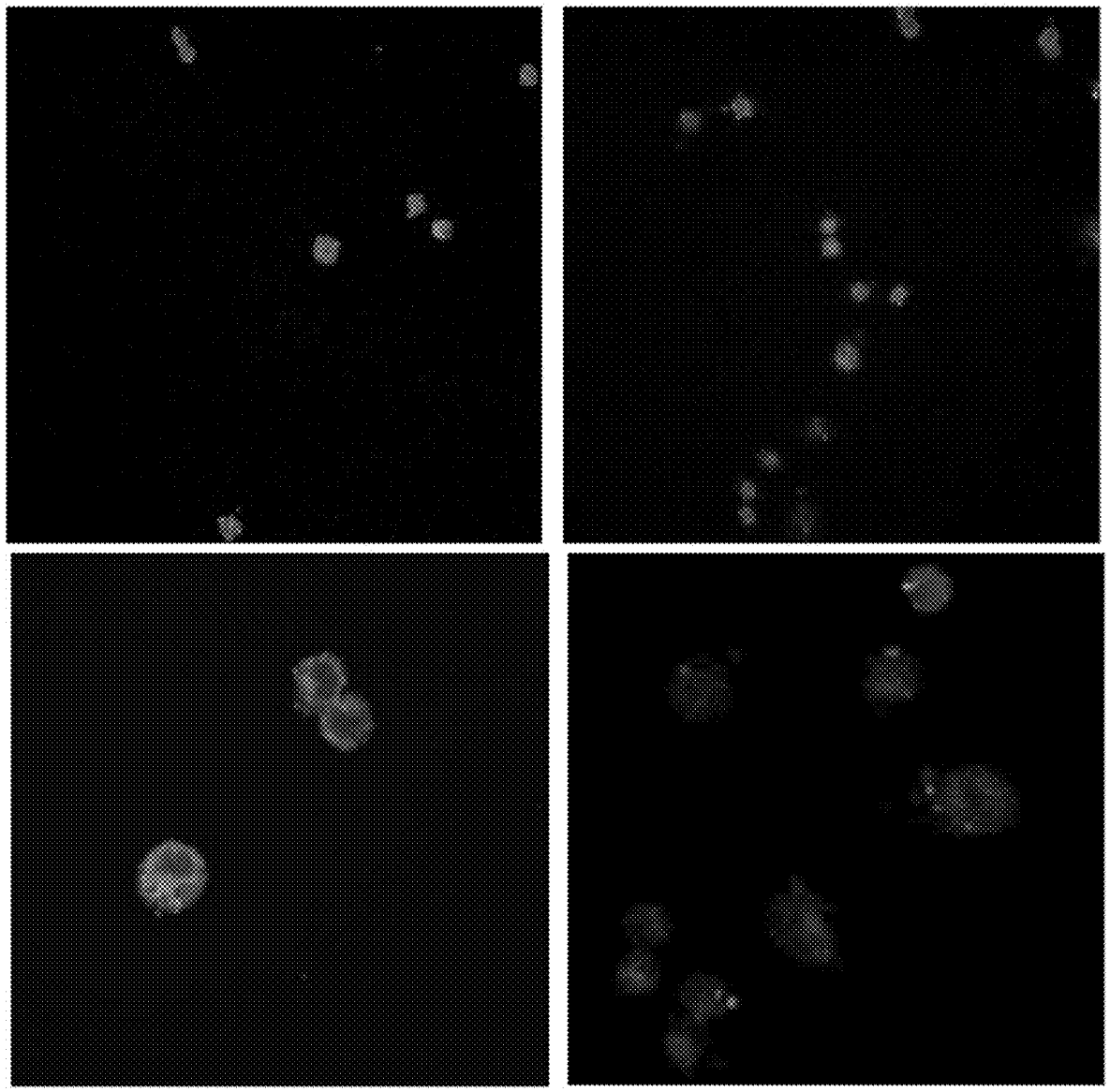
FIG. 5. shows large relaxin-2-loaded microparticles are not endocytosed by murine macrophages in vitro. (left) Fluorescently-labelled control PLGA-microparticles (red) with average diameter of 4.5 μm are endocytosed by RAW 264.7 murine macrophages after 24 h of incubation. (right) Fluorescently-labelled Relaxin-2 loaded microparticles are excluded from RAW 264.7 macrophages and do not fluoresce internally. Images on top are captured at 10× magnification, and images on bottom are captured at 20× magnification.

The synovial joint space consists of two major cell types: synovial fibroblasts and macrophages. The in vitro tolerability of RAW 267.4 murine macrophages to relaxin-2 microparticles was evaluated. After a 24-hour treatment, macrophages internalized fluorescently labelled control microparticles with average diameter of 4.5 μm (FIG. 5, left). After 24-hour treatment, macrophages did not internalize fluorescently labelled control microparticles, with average diameter of 7.6 m (FIG. 5, right).

Example 2. Formation and Characterization of Amphiphilic Hydrogel Depots for the Sustained Release of Relaxin-2

Figure 6:
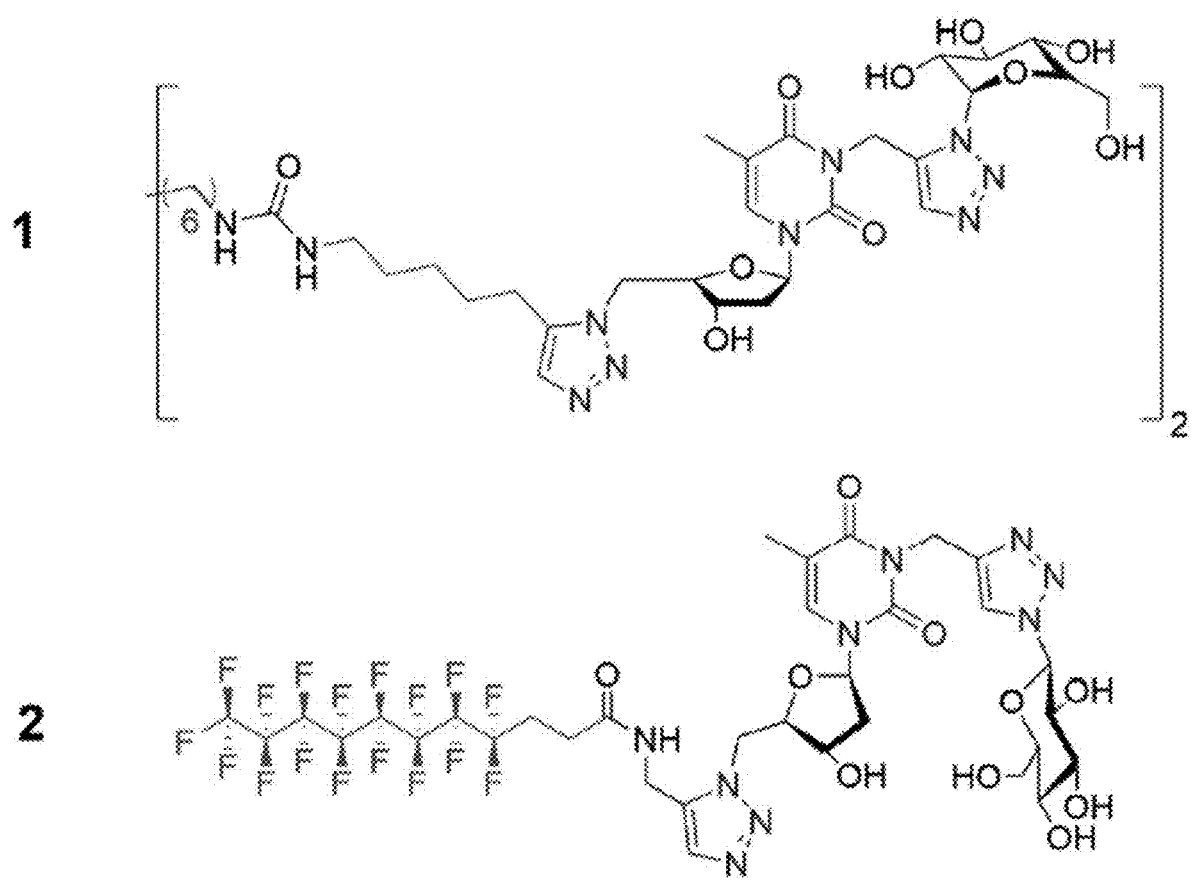
FIG. 6 shows structures of supramolecular gel constituents have low molecular weight and regions with various physical properties. The bola bis urea molecule 1 and glucosyl-nucleoside fluorinate amphiphile both have regions of hydrophobicity (red), aromaticity (blue), and hydrophilicity (black). These regions favor a combination of hydrophobic, pi-pi stacking, and hydrogen bonding with each other respectively.
Figure 7:
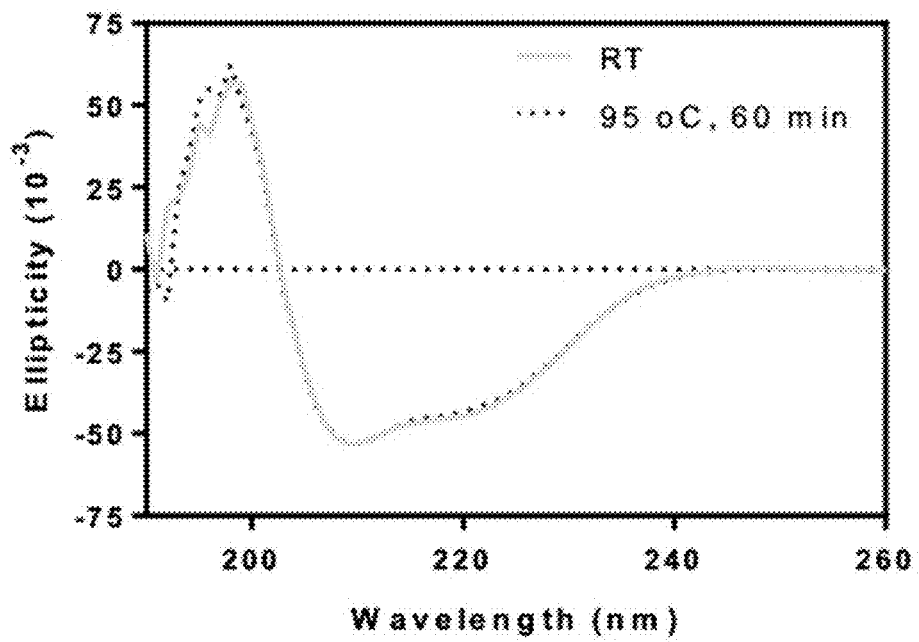
FIG. 7 shows Relaxin-2 can be successfully loaded into an amphiphilic hydrogel without compromising its structure. Relaxin-2 is tolerant to incubation for at least one hour at 95° C. as indicated by circular dichroism, which shows its alpha-helical conformation unperturbed (left). Relaxin-2-loaded amphiphiles will gelate with relaxin-2 incorporated inside of them (right).
Figure 7:
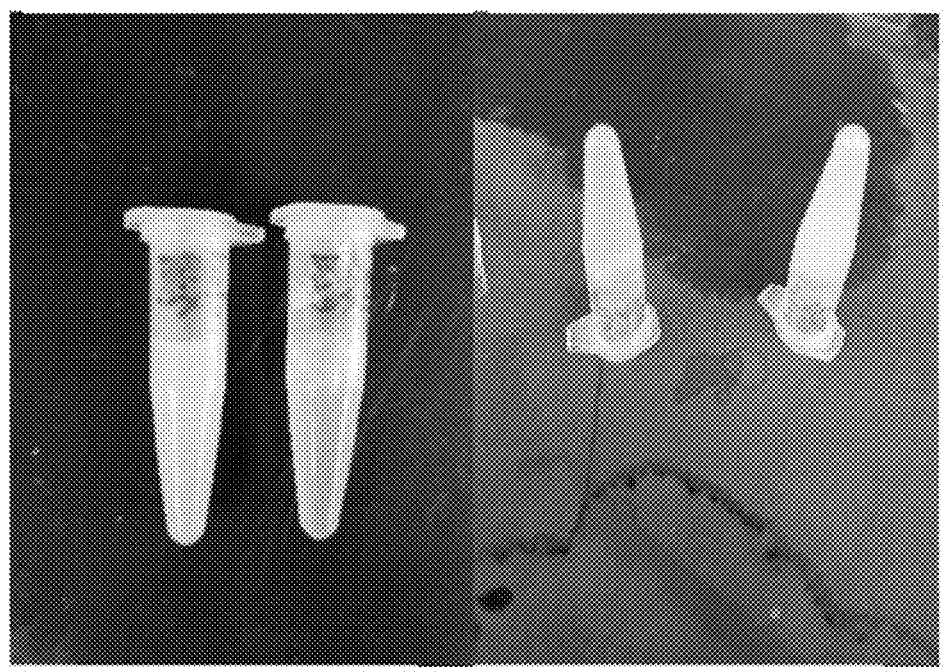

Two amphiphilic hydrogels were synthesized for the physical entrapment of relaxin-2 in order to control its sustained release (FIG. 6). These amphiphilic molecules melted at 95° C. and congealed when slowly cooled back to room temperature strictly from non-covalent interactions. The alkyl chain of 1 and alkyl fluoride chain of 2 allow for hydrophobic interactions between each molecule, while the trizol and thymidine moieties allow for pi-pi stacking. Lastly, the deoxyribose and glucose groups facilitate hydrogen bonding (Godeau, G., et al., Tetrahedron Letters 2010, 51: 1012-1015; Ramen, F. A. et al., Biomaterials. 2017, 145:

72-80). Together, these amphiphilic molecules create unique and stable supramolecular assemblies that are stable at 37° C. for at least two weeks. This stability feature is another novel finding and benefit to the use of the hydrogels. Three gels of each 1 and 2 were created with bovine serum albumin and relaxin-2 at different densities by dissolving each molecule in a solution of phosphate buffered saline with protein and heating to 95° C. for 30 minutes. Relaxin-2 maintains its folded 3D structure by circular dichroism spectroscopy after treatment at this temperature for at least one hour (FIG. 7, left). After cooling down to room temperature, relaxin-2-loaded gels were fully congealed (FIG. 7, right).

Figure 8:
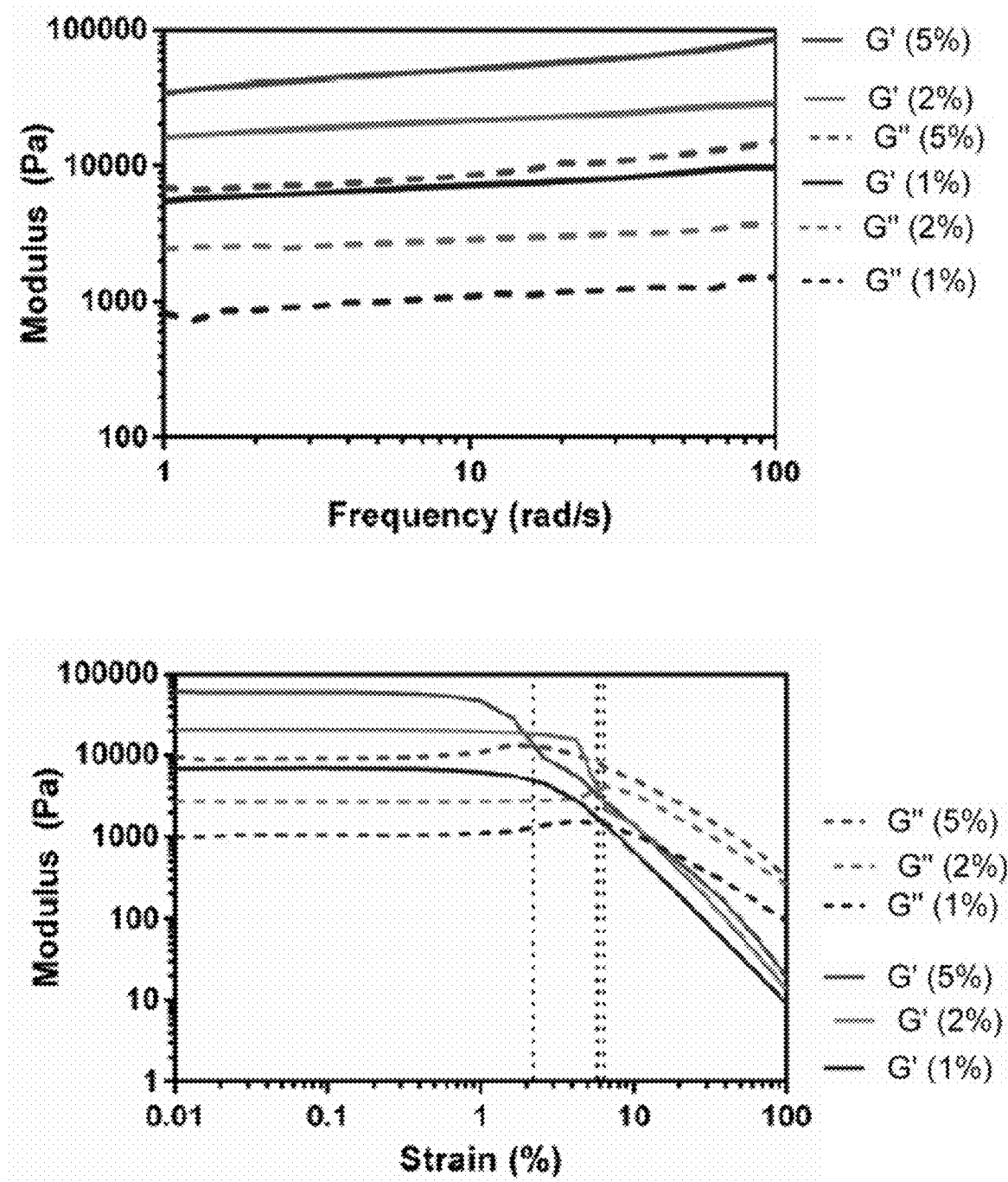
FIG. 8 shows rheological properties of bola bis urea 1. (left) Gel 1 at 1, 2, and 5 wt % densities all exhibit solid-like materials up to a frequency of 100 rad/s as indicated by their storage (G') and loss (G") moduli. In all gels, G'>G", where G'/G" remains approximately constant and independent of wt %. The absolute values of G' and G" are logarithmically proportional to the gel density. (right) The linear viscoelastic regions were determined from a strain sweep ranging from 0.01 to 100% strain. The 5% gel showed exhibited the smallest LVER where G">G' at 2.2% strain. The 2% gel and 1% gels transition from the LVER at 5.8 and 6.4% strain, respectively (vertical, dotted lines).
Figure 9:
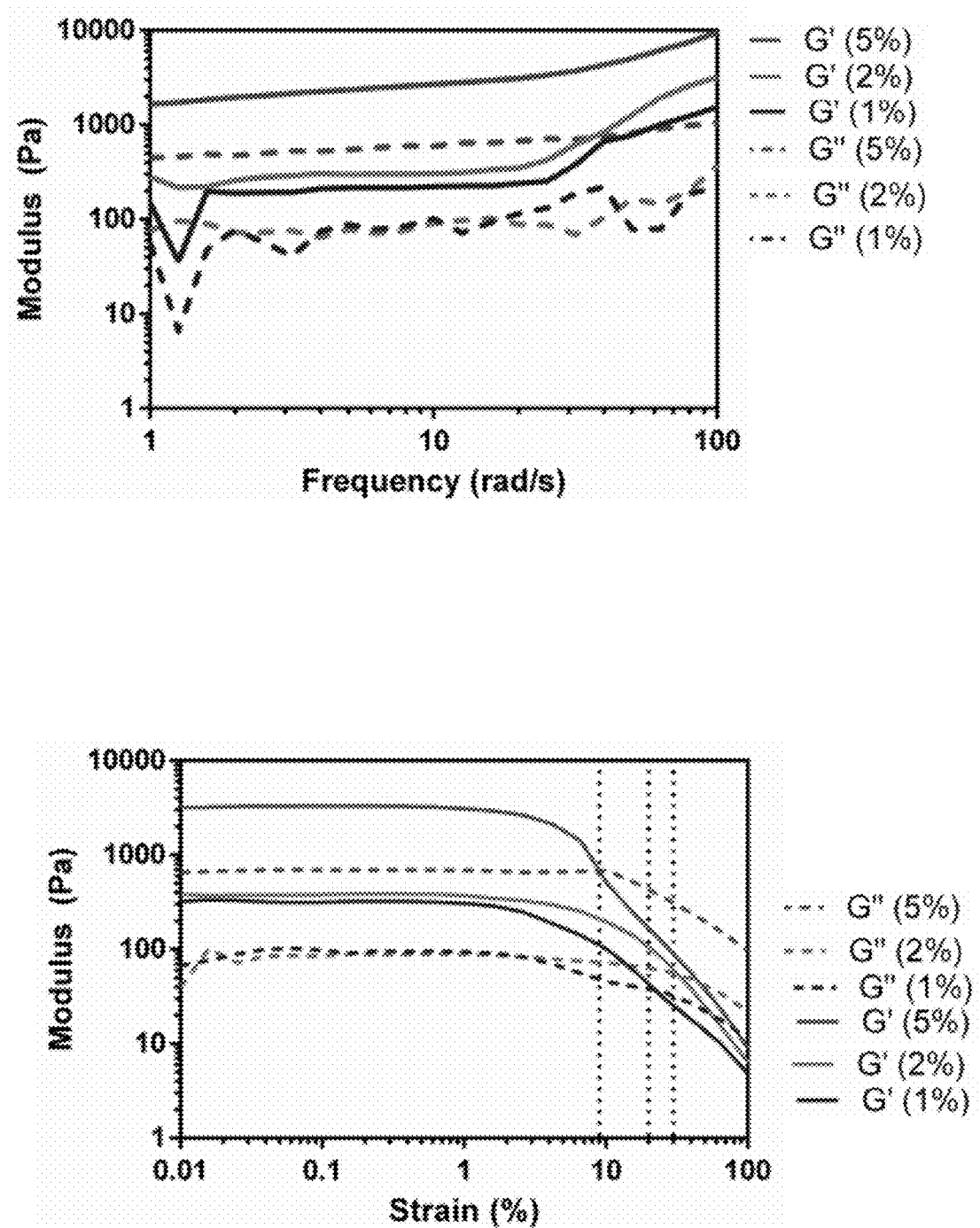
FIG. 9 shows rheological properties of glycosyl-nucleoside florinated amphiphile 2. (left) Gel 2 at 1, 1.5, and 5 wt % densities all exhibit solid-like materials up to a frequency of 100 rad/s as indicated by their storage (G') and loss (G") moduli. The absolute values of G' and G" are logarithmically proportional to the gel density. (right) The linear viscoelastic regions were determined from a strain sweep ranging from 0.01 to 100% strain. The 5% gel showed exhibited the smallest LVER where G">G' at 9% strain. The 2% gel and 1% gels transition from the LVER at 20 and 30% strain, respectively (vertical, dotted lines).

The rheological properties of these supramolecular hydrogels loaded with relaxin-2 were assessed. The storage (G') and loss (G") moduli were determined from a frequency sweep from 1 to 100 rad/s. In this range, all gels maintained a greater storage modulus than loss modulus (G'>G") indicating that all gels behave more as an elastic solid than viscous liquid in this frequency regime (FIG. 8, left, FIG. 9, left). A strain sweep of gel 1 at various wt % reveals the linear viscoelastic regions (LVERs) between 2.2% strain to 6.4% strain from high to low wt % gels, respectively (FIG. 8, right). The LVERs are inversely related to the gel wt %. Alternatively, in gel 2 at various wt %, this relationship is lost (FIG. 9, right). The 5 wt % gel shows the narrowest LVER, ending at 9% strain. The 1.5 wt % gel shows the largest LVER ending at 30%, and the 1 wt % gel is intermediate between the two with a LVER ending at 20% strain (FIG. 9, right).

Figure 10:
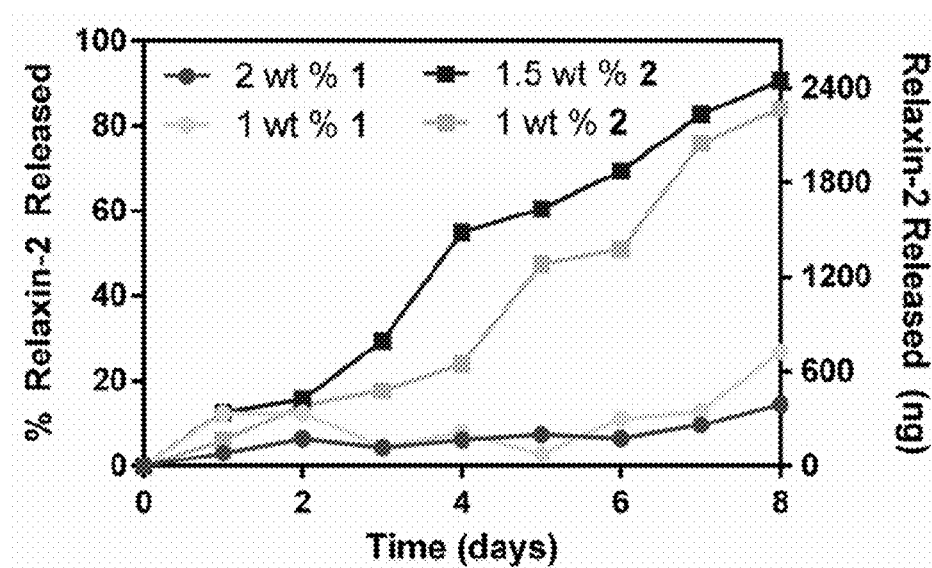
FIG. 10 shows Relaxin-2 is release from both amphiphilic gel formulations with different kinetics over 8 days. Gels made from amphiphile 1 (green) release relaxin-2 in a significantly slower manner than they do for gels made from amphiphile 2 (blue). Almost all relaxin-2 is released from the gels made from compound 2 over this timeframe whereas gels made from 1 release approximately 5-fold slower. There is a proportionality observed with the release rate and the wt % for the gels made from 1 whereas this proportionality is absent in gels made from 2.

The release profile of 1 and 2 wt % in 1 and 1 and 1.5 wt % in 2 were assessed over the course of 8 days at 37° C. in a reservoir of phosphate buffered saline. In this time frame, both gels created from molecule 2 released 90 and 84% of the total loaded relaxin-2 (FIG. 10). The gels prepared from compound 1 exhibited a significantly slower release pattern than those of compound 2. These gels release only 15 and 27% of the total loaded relaxin-2 (FIG. 10). The gels made from compound 1 show a proportionality between release time and wt %, whereas this trend is absent in gels made from compound 2. Over the course of 8 weeks, all gels remained intact with some swelling observed. There were no apparent signs of the material degrading. The understanding for why these two gels release relaxin at different rates is unknown and as such points to this remarkable finding.

Example 3: Development of a Shoulder Contracture Model in Rats

The purpose of this experiment, which is described in the publication by Villa-Camacho et al., Journal of Shoulder and Elbow Surgery, 2015, 24(11): 1809-16, was to investigate the effects of extraarticular, internal fixation of the glenohumeral joint on shoulder kinetics and kinematics in an in vivo animal model of shoulder contracture. It was expected that extraarticular, internal fixation of the shoulder in rats would result in a subsequent decrease in rotational ROM and an increase in joint stiffness, which would persist for at least 8 weeks.

The study was approved by the Institutional Animal Care and Use Committee, and 10 Sprague-Dawley rats (250-300 g, Charles River Laboratories, Wilmington, Mass., USA) were used in the study. For each animal, torque was measured per degree, on the intact left shoulder as a function of rotation angle between 80° of internal rotation (negative values by convention) and 60° of external rotation (positive values by convention) prior to any surgical intervention (baseline). Rotation was confined within boundaries that were observed to elicit minimal scapular recruitment, as confirmed by fluoroscopy. Therefore, torque values at 60° external rotation (τOUT) and 800 of internal rotation (τINT) were recorded for each animal.

The left forelimb of each animal was immobilized using extraarticular internal fixation. Under isoflurane anesthesia, a longitudinal skin incision was made perpendicular to the scapular spine. Two No. 2-0 braided polyester sutures (Ethibond Excel, Ethicon—San Lorenzo, PR, USA) were passed between the medial border of the scapula and the humeral shaft and tightened to immobilize the shoulder joint (FIG. 1, panel A). Muscular structures were not manipulated during surgery, and the animals were allowed normal activity in their cages immediately after the procedure.

After 8 weeks of immobilization, the restraining sutures were removed, and the 10 animals were divided into two groups to evaluate changes in ROM (ROM group, n=5) and joint stiffness (stiffness group, n=5). In the ROM group, changes in kinematics were longitudinally quantified in the follow-up period by measuring the ROM achieved with the TOUT and TINT measured at baseline. This was conducted to evaluate whether immobilization mediated a significant reduction in ROM. In the stiffness group, joint kinetics were examined by measuring the differences in TOUT and TINT needed to achieve the original 800 of internal rotation and 60° of external rotation, respectively. Measurements for both groups were taken immediately after suture removal (day 0 of follow-up) and at regular intervals thereafter (twice a week until less than 10% change was observed in three consecutive time points, at which point, measurement frequency was reduced to once a week). The baseline measurements for each group were used as internal controls to reduce the total number of animals necessary for the study. The use of internal controls also increased internal validity and statistical power as there was a high inter-specimen variation, of both ROM and measured torques, even when using the contralateral shoulder of the same animal. Finally, a pilot study demonstrated that intra-specimen measurements were highly reproducible and remained stable during an 8-week period.

ROM and torque measurements were performed under general anesthesia using a device that consisted of a sensor assembly, a rotating axle, and an arm clamp. The sensor assembly contained an orientation sensor (3DM-GX3-15, MicroStrain—Williston, Vt.), as well as a reaction torque sensor (TFF400, Futek—Irvine, Calif.) secured to the axle such that the sensing axis was collinear with the center of rotation. The forelimb was secured at 3 points (wrist, elbow, and arm), ensuring that the sensing axis was aligned with the long axis of the humerus. Rotation of the sensor assembly resulted in direct internal humeral rotation and external humeral rotation within the glenohumeral joint.

To reproducibly capture ROM and torque, passive limb rotation was performed by a stepper motor controlled with a microcontroller (UNO R3, Arduino—Torino, Italy). The system utilized inputs from the reaction torque sensor or the orientation sensor to start and end the dynamic measurement of ROM and torque. In the ROM group, pre-set programmable torque values, specific for each animal and measured at baseline (TOUT and TINT), were used as input variables in order to detect changes in rotation ROM with 0.2° resolution. In the stiffness group, pre-set programmable rotation angles (600 external rotation, 800 internal rotation) were used as input to measure changes in torque at a resolution of 0.01 N/mm. The microcontroller was directed by a computer using MATLAB 7.13.0.564 (MathWorks Inc—Natick, Mass., USA).

In the ROM group, mean ROM values were compared at three different time points (baseline, immediately after suture removal, and at 8 weeks of follow-up) by repeated-measures analysis of variance. In the stiffness group, two different metrics were used for comparison: 1) the difference in torque required to achieve full ROM, and 2) stiffness, estimated from the area under the rotation angle-torque curve. A value of $P<0.05$ was considered statistically significant for both groups. The ROM temporal behavior in the follow-up period was determined. Immediately after suture removal, there was a 63% decrease in total ROM compared with baseline (51° 10° vs. 136° f 0°; $P<0.001$). Similarly, total torque increased 13.4 N·mm compared with baseline (22.6±5.9 N·mm vs. 9.2±2.6 N·mm; $P=0.002$). Residual total ROM restrictions and an increased torque in internal rotation were still evident at 8 weeks of follow-up (113°±8° vs. 137°±0°, $P<0.001$ and 3.5±0.4 N·mm vs. 2.7±0.7 N·mm, $P=0.036$).

The kinetic and kinematic changes were not transitory. At 8 weeks follow-up, both the reduction in ROM and the increase in joint stiffness were significant. While no studies have evaluated the natural progression and temporal behavior of this shoulder contracture model, it is expected that joint residual changes present after 8 weeks into the post-immobilization period are likely permanent (Trudel G. et al., Journal of Applied Physiology (Bethesda, Md.: 1985), 2014, 117(7):730-7). The results presented in Example 4 indicate that a shoulder contracture model in rats may be used to evaluate therapeutic interventions to treat shoulder contracture.

The above described findings were subsequently validated by Kim et al., who independently reported a similar model of shoulder contracture (Kim et al., J. Orthop. Surg. Res. 2016; 11(1):160). A series of microscopic images of the axillary recess of the glenohumeral joint was similar to that as seen in Kim et al., taken over 6 weeks. The Masson's trichrome stain was utilized to identify fibrosis (red). Histologic evidence of contracture development at 3 days and 6 weeks is observed. Fibrosis and inflammation occurred early and persisted during immobilization, and notably, the infiltration of inflammatory cells, capsular thickening, and angiogenesis within capsular tissue was apparent as early as 3 days. While the acute inflammatory response lessened by week 6, capsular thickening and fibrotic structures still remained, closely mimicking findings from other studies (Trudel et al., J. Appl. Physiol. (1985), 2014, 117(7):730-7). This model of lasting reduced ROM and increased stiffness allows for the comprehensive evaluation of current and potential therapeutic interventions for shoulder contracture.

Figure 11:
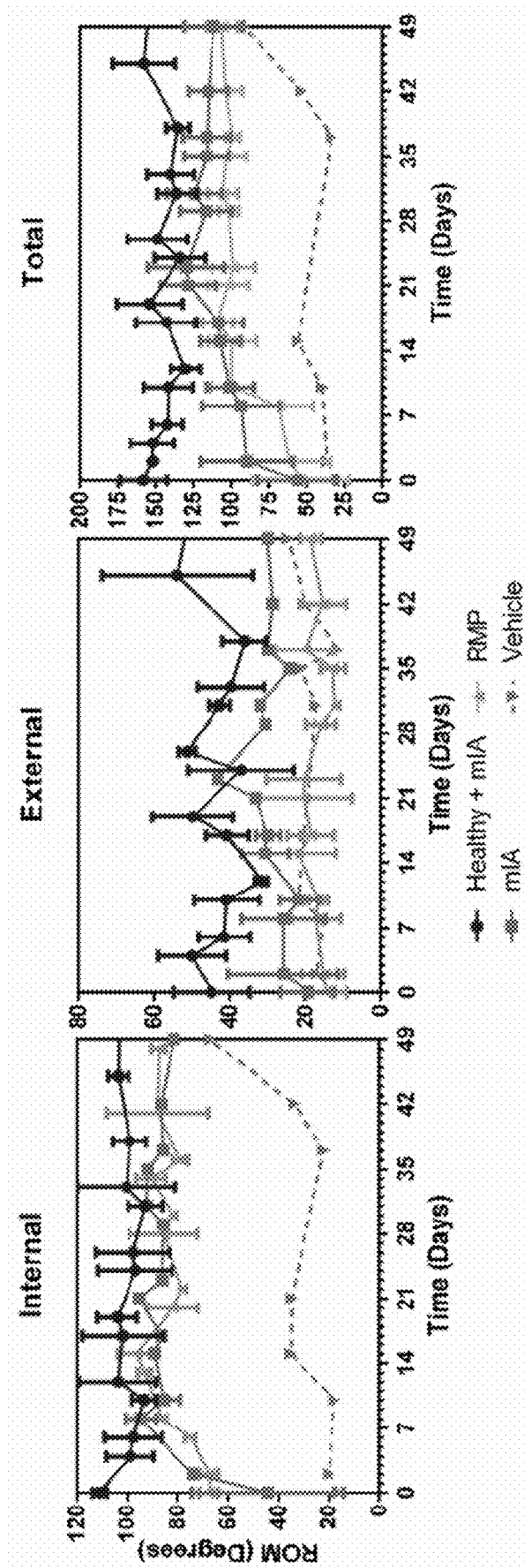
FIG. 11 shows Relaxin-2 therapies improve internal ROM back to baseline levels, but do not affect external ROM in 7 weeks. (left) The internal ROM after suture removal shows constancy in the healthy, non-surgical group (blue). All surgical groups show a decreased post-surgical baseline in ROM, however, the mIA and RMP groups show a significant increase back to healthy baseline by week 2. The vehicle control shows significantly less ROM than the treatment groups until week 7. (middle) The external ROM of the surgical groups are significantly less and do not improve back to healthy baseline over the course of this study. (right) Total ROM shows a slight improvement of the treatment groups compared to the vehicle control, however, baseline ROM is not achieved in the course of the study.
Figure 12:
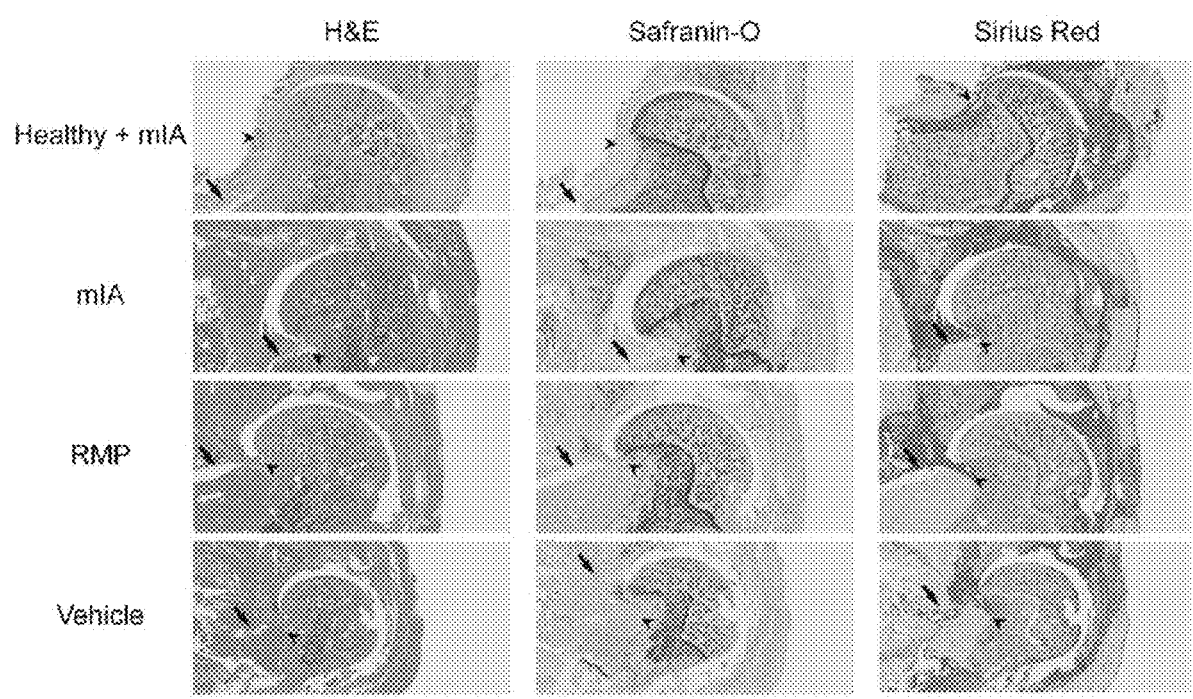
FIG. 12 shows histological hallmarks of arthrofibrosis are observed in the vehicle control, but are absent in treatment and healthy groups. (left) H&E staining of the humeral head and glenohumeral joint show an increased deposition of fibroblasts near the joint capsule (arrowhead) in the vehicle control. This deposition is significantly less in the healthy control. There is also fibroblast-infiltration in surrounding the top of the humerus (arrow) that is absent in the healthy control and treatment groups. (middle) Safranin-O staining shows that the architecture of glycosamino glycans is largely unchanged between all groups. (right) Sirius red staining of the shoulder joint shows significant deposition of fibroblasts with directional orientation, indicative of fibrosis. Delineation between the fibrotic capsule and joint capsule are present except in the vehicle control (arrows).

Example 4. Use of a Relaxin-2 Microparticle to Treat a Stiffened Joint in a Murine Model This study investigated the effects of recombinant human relaxin-2 on the kinetics and kinematics of the glenohumeral joint in an animal model of shoulder contracture, as described in Villa-Camacho et al., Journal of Shoulder and Elbow Surgery, 2015, 24(11): 1809-16. It was expected that rats treated with multiple intraarticular (mIA) injections of relaxin-2 would exhibit a more rapid recovery of range of motion (ROM) throughout an 8 week monitoring period than untreated controls. For each animal, torque was measured per degree, on the intact left shoulder as a function of rotation angle between 1000 of internal rotation and 600 of external rotation prior to any surgical intervention. After 8 weeks of immobilization, ROM was measured and rats were injected with relaxin-2 at 2 ug/kg in phosphate buffered saline (i.e., vehicle group) directly into the synovial joint space of the stiff shoulder under fluoroscopic guidance (Day 0). Rats received a total of 5 injections of relaxin-2 at 2 ug/kg administered every other day for 10 days for a total of 10 ug/kg administered per rat (i.e., MIA group). Rats were injected on Day 0 with a single dose of PLGA microparticles encapsulating approximately 10 ug/kg relaxin-2 (i.e., RMP group). As an additional control a separate set of animals receive no shoulder contracture and receive a total of 5 injections of relaxin-2 at 2 ug/kg every other day for 10 days for a total of 10 ug/kg administered per rat (i.e., Healthy+ MIA group). Changes in kinematics were longitudinally quantified starting at Day 0 and in the follow-up period by measuring the ROM achieved with the τOUT and τINT measured at baseline. ROM measurements were taken immediately after suture removal (day 0 of follow-up) and at regular intervals thereafter (twice a week until less than 10% change was observed in three consecutive time points, at which point, measurement frequency was reduced to once a week) for an 8-week follow-up period. The baseline measurements for each group functioned as internal controls in addition to the same ROM measurements on the contralateral uninjured shoulder. Rats receiving mIA of relaxin-2 or relaxin loaded in the microparticle (RMP) demonstrated restoration of internal ROM to baseline measurements after the 8-week follow-up period (FIG. 11). Using this model, a singular articular injection or relaxin or an intravenous injection of relaxin-2 at a much greater dose shows a similarly constricted internal ROM compared with the untreated control group. Histological analysis of the shoulder joint demonstrated that immobilized shoulders of untreated rats has reduced delineated separation between the capsule and the articular surface on the humeral head, fibroblast infiltration and capsular adhesions, while immobilized shoulders of rats that received mIA of relaxin-2 (Blessing, W. A., et al., *Proc. Natl. Acad. Sci.* 2019, 116: 12183-12192) or relaxin loaded microparticles lacked any apparent adhesions and the synovial membrane and the articular cartilage surfaces remained separated from one another with proper cellular organization, and displayed reduced foreign body response compared to vehicle microparticle control (FIG. 12).

Figure 13:
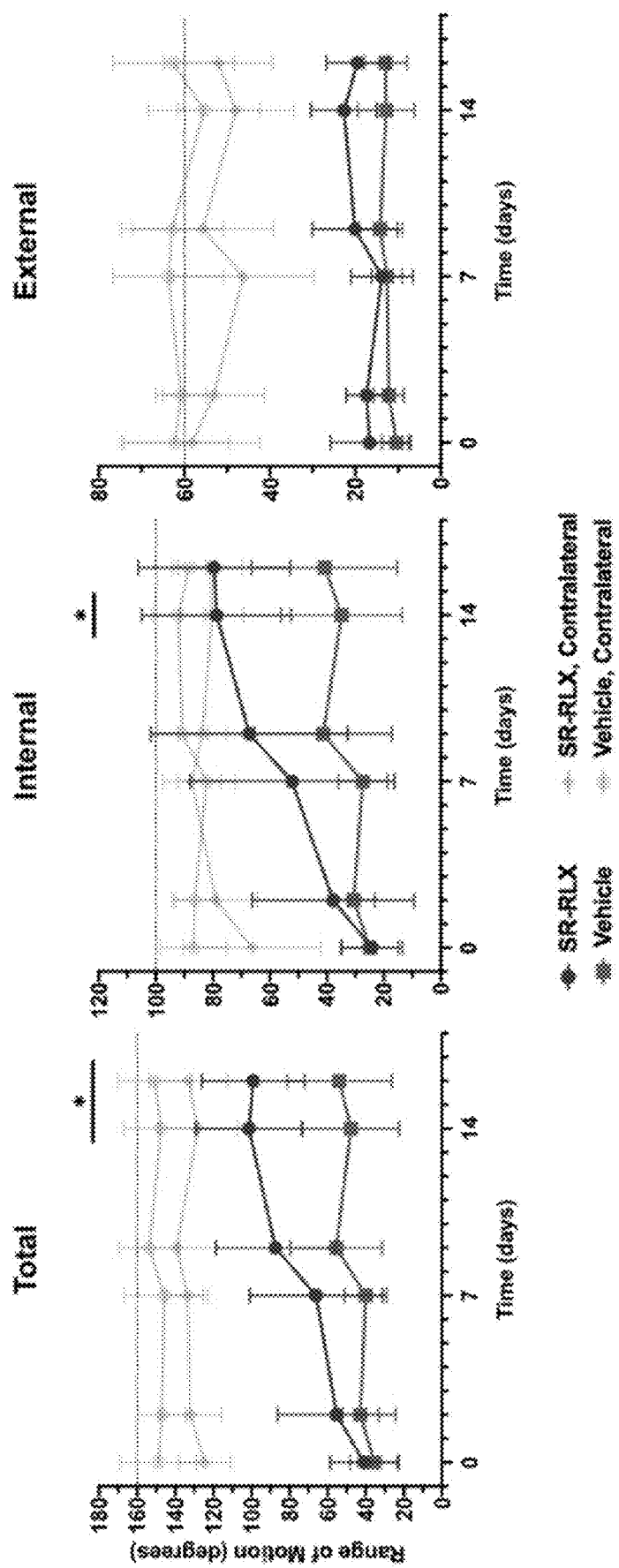
FIG. 13 shows sustained release of Relaxin-2 improves total ROM. Induction of contracture is consistent between the vehicle (n=9) and loaded depot (n=7) groups (time=0). Both the internal (middle) and total (right) range of motion show recovery at the later time points indicating efficacy of relaxin release into the joint space.

Using the contracture model above, animals at day 0 receive vehicle (empty microparticle) or relaxin loaded microparticles (i.e., SR-RLX) and were followed for 8 weeks. FIG. 13 shows range of motion recovery of the shoulder of rats receiving a single intra-articular injection or relaxin-2 loaded microparticles was similar to that of rats receiving 5 intra-articular injections of relaxin-2. Control unloaded vehicle microparticles and control saline injections demonstrated similar ROM recovery. This recovery was less than that of the relaxin-2 treatment groups data for total, internal and external angles. There is a statistically significant difference between the total range of motion in rats treated with relaxin loaded depots (n=7) and unloaded vehicle controls (n=9) at the 14 and 16 day time point (p<0.01). This data are in agreement with the results from FIG. 11.

Example 5. Use of Relaxin-2 Loaded Microparticles to Treat a Stiffened Joint in a Human Subject Relaxin-2 microparticles, 35 μm in diameter, comprised of PLGA (molar ratio 45:65 lactide:glycolide, M.W. 50,000-75,000 daltons, carboxylic acid terminated, and loaded at 1% relaxin weight/weight, are administered to a patient diagnosed with shoulder adhesive capsulitis. Prior to injection, relaxin-2 microparticles are resuspended in a sterile, isotonic carboxymethylcellulose diluent to a total volume such that the final dose is 50 μg/kg body weight. Administration is in the form of 1 ml intraarticular injection using a 23 G needle. Following injection, the patient is monitored for changes in joint range of motion, (e.g. internal rotation, external rotation, pronation, supination, flexion, extension, abduction, and adduction) patient reported pain, mobility, patient reported autonomy, and patient reported quality of life.

Example 6. Use of Relaxin-2 Loaded Microparticles to Treat Stiffened Joints Secondary to a NMD Relaxin microparticles, 35 μm in diameter, comprised of PLGA (molar ratio 50:50 lactide:glycolide, M.W. 70,000-90,000 daltons, ester terminated) and PVA (M.W. 30,000 daltons), and loaded at 0.5% relaxin weight/weight, are administered to a patient diagnosed with Duchene's Muscular Dystrophy presenting with contracture of the acetabulofemoral joint. Prior to injection, relaxin microparticles are resuspended in sterile saline-buffer-based diluent to a total volume such that the final dose is 20 ug/kg body weight. Administration is in the form of 1 ml intraarticular injection using a 21 G needle. Subsequent injections of 1 ml at 10 ug/kg are performed every 14 days for 70 days following the initial injection. Following in initial injection, during repeated dosages, and after completion of dose regime, the patient is monitored for changes in joint range of motion, (e.g. internal rotation, external rotation, pronation, supination, flexion, extension, abduction, and adduction) patient reported pain, mobility, patient reported autonomy, and patient reported quality of life.

Example 7. Use of Relaxin-2 Loaded Microparticles to Treat Pulmonary Fibrosis

Relaxin microparticles, 3.1 μm in diameter, comprised of PLGA, and loaded at 0.5% relaxin weight/weight, and administered to a patient diagnosed with idiopathic pulmonary fibrosis presenting with reduced forced vital capacity and a dry cough. Prior to administration, relaxin microparticles are gentle agitated to deagglomerate any dry powder clumps that formed during storage. Using a dry powder metered dose inhaler, that patient is given an inhaled dose equivalent to 25 ug/kg. Following administration, the patient is monitored for decreases in pathological hallmarks of fibrosis via CT scan, as well as for increased forced vital capacity, and decrease in respiratory distress symptoms Example 8. Use of Relaxin-2 for the Treatment of Fibrosis The present invention provides compositions of matter and methods for treating fibrotic diseases including stiffened fibrotic joint capsules, lung fibrosis (i.e. idiopathic pulmonary fibrosis, cystic fibrosis, hypertension), liver fibrosis (i.e. hepatitis B or C, long-term alcohol abuse, non-alcoholic steatohepatitis, non-alcoholic fatty liver disease, Cholestasis, autoimmune hepatitis cirrhosis), kidney fibrosis (i.e. chronic kidney disease, end-stage renal disease, renal interstitial fibrosis), heart disease (i.e. heart failure, myocardial infarction, aortic stenosis, hypertrophic cardiomyopathy), intestinal disease (i.e. Crohn's disease, inflammatory bowel disease, enteropathies, and other intestinal fibrosis), skin conditions (i.e. scleroderma, keloids, hypertrophic scars, cellulite), urogenital and gynecological conditions (Peyronie's disease, uterine fibroids) and ocular diseases (i.e. Congenital Fibrosis of the Extraocular Muscles, subretinal fibrosis, epiretinal fibrosis, corneal fibrosis) in a subject by administering a depot containing a binding agent for relaxin family peptide receptors (RXFP1, RXFP2, RXFP3, RXFP4). The agent will be the native ligand of the receptor, relaxin-2, a relaxin-2 variant, relaxin-2 chemically conjugated to a targeting agent, including a single-domain camelid antibody fragment, a peptide sequence, polynucleotide, or a small molecule, or a small molecule allosteric modulator The depot is an object with a volume of at least 0.1 μm3 and is comprised of one or more polymers or self-assembled small molecules that delivers the minimally effective clinical dose over several weeks to several months. The relaxin loaded depot may be administered intravenously, intramuscularly, subcutaneously, intradermally, intranasally, orally, transcutaneously, mucosally, intraarticularly, periarticularly, intracapsularly, pericapsularly, intratendinously, peritendinously, intraligamentously, periligamentously, by pulmonary inhalation or by ocular specific routes of administration as a sustained release formulation and may be provided as a single injection or a series of injection.

LISTING OF SEQUENCES

SEQ ID NO: 1
>gi|6497221|gb|AA126416.1 Relaxin 2 [Homo sapiens]
MPRLFFFHLLGVCLLLNQFSRAVADSWMEE-
VIKLCGRELVRAQIAICGMSTWSKRSLSQEDAPQT-
PRPVAEIV PSFINKDTETINMMSEF-
VANLPQELKLTLSEMQPALPQLQQHVPVLKDSSLL
FEEFKKLIRNRQSEAADSSPS
ELKYLGLDTHSRKKRQLYSALANKC-
CHVGCTKRSLARFC SEQ ID NO: 2
>gi|16496899|gb|AAI26420.1| Relaxin 2 [Homo sapiens]
MPRLFFFHLLGVCLLLNQFSRAVADSWMEE-
VIKLCGRELVRAQIAICGMSTWSKRSLSQEDAPQT-
PRPVAE IVPSFINKDIETINMMSEF-
VANLPQELKLILSEMQPALPQLQQHVPVLKDSSLL
FEEFKKLIRNRQSEAAD SSPSEL-
KYLGLDTHSRKKRQLYSALANKC-
CHVGCTKRSLARFC SEQ ID NO: 3
>gi|313884020|gb|ADR83496.1| relaxin 2, partial [synthetic construct]
MPRLFFFHLLGVCLLLNQFSRAVADSWMEE-
VIKLCGRELVRAQIAICGMSTWSKRSLSQEDAPQT-
PRPVAE IVPSFINKDIETINMMSEF-
VANLPQELKLILSEMQPALPQLQQHVPVLKDSSLL
FEEFKKLIRNRQSEAAD SSPSEL-
KYLGLDTHSRKKRQLYSALANKC-
CHVGCTKRSLARFC SEQ ID NO: 4
>gi|3543609|gb|AAH05956.1| Relaxin 1 [Homo sapiens]
MPRLFLFHLLEFCLLLNQFSRAVAAKWKDD-
VIKLCGRELVRAQIAICGMSTWSKRSLSQEDAPQT-
PRPV AEIVPSFINKDIETIIMLEFIANLPPEL-
KAALSERQPSLPELQQYVPALKDSNLSFEEFKKLIR
NRQSEAA DSNPSELKYLGLDTHSQKKRRPYVAL-
FEKCCLIGCTKRSLAKYC SEQ ID NO: 5
>gi|19579171|gb|EAW58767.1| relaxin 1, isoform CRA_a [Homo sapiens]
MPRLFLFHLLEFCLLLNQFSRAVAAKWKDD-
VIKLCGRELVRAQIAICGMSTWSKRSLSQEDAPQT-
PRPV A EI VPSFINKDIETIIMLEFIANLPPEL-
KAALSERQPSLPELQQYVPALKDSNLSFEEFKKLIR
NRQSEAADS NPSELKYLGLDTHSQKKRRPYVAL-
FEKCCLIGCTKRSLAKYC SEQ ID NO: 6
>gi|9579172|gb|EAW58768.1 relaxin 1, isoform CRA b [Homo sapiens]
MPRLFLFHLLEFCLLLNQFSRAVAAKWKDD-
VIKLCGRELVRAQIAICGMSTWSKRSLSQEDAPQT-
PRPVAGISSSLL RRRLFEDHDGPSFLV SEQ ID NO: 7
>gi|19579173Hg-bEAW58769.1 relaxin 1, isoform CRA c [Homo sapiens]
MLEFIANLPPELKAALSER-
QPSLPELQQYVPALKDSNLSFEEFKK-
LIRNRQSEAADSNPSELKYLGLDTHSQKKRRPY
VALFEKCCLIGCTKRSLAKYC SEQ ID NO: 8
>gi|19604794|gb|EAW84388.1 relaxin 3 [Homo sapiens]
MARYMLLLLLAVWVLTGELWPGAEARAAPY-
GVRLCGREFIRAVIFTCGGSRWRRSDILA-
HEAMGDTFPDADADED SLAGELDEAMGSSEW-
LALTKSPQAFYRGRPSWQGTPGVLRGSRDVLAGL
SSSCCKWGCSKSEISSLC SEQ ID NO: 9
>gi|87954661|gb|AAI40936.1 Relaxin 3 [Homo sapiens]
MARYMLLLLLAVWVLTGELWPGAEARAAPY-
GVRLCGREFIRAVIFTCGGSRWRRSDILA-
HEAMGDTFPDADADE DSLAGELDEAMGSSEW-
LALTKSPQAFYRGRPSWQGTPVVLRGSRDVLAGL
SSSCCKWGCSKSEISSLC SEQ ID NO: 10
>gi|7484096Hg|bAAL40345.1AF447451 1 relaxin 3 [Homo sapiens]
MARYMLLLLLAVWVLTGELWPGAEARAAPY-
GVRLCGREFIRAVIFTCGGSRWRRSDILA-
HEAMGDTFPDADADEDSLAGELDEAMGSSEWLA-
LTKSPQAFYRGRPSWQGTPGVLRGSRDVLAGLSS
SCCKWGCSKSEISSLC SEQ ID NO: 11
>gi|317373369|sp|J051460.2|INSL3 HUMAN RecName: Full=Insulin-like 3;
MDPRLPAWALVLLGPALVFALGPAPTPEM-
REKLCGHHEVRALVRVCGGPRWSTEARRPATGG-
DRELLQWLERRHLLH
GLVADSNLTLGPGLQPLPQTSHHHRHHRAAATN-
PARYCCLSGCTQQDLLTLCPY SEQ ID NO: 12
>gi|19579176|gb|EAW58772.1 insulin-like 4 (placenta) [Homo sapiens]
MASLFRSYLPAIWLLLSQLLRESLAAEL-
RGCGPRFGKHLLSYCPMPEKTFTTTPGGWLLES-
GRPKEMVSTSNNKDG QALGTTSEFIPNL-
SPELKKPLSEGQPSLKKIILSRKKRSGRHRFDPFCC
EVICDDGTSVKLCT

SEQ ID NO: 13

>gi20070773HgbAAH26254.1 Insulin-like 4 (placenta) [Homo sapiens]

MASLFRSYLPAIWLLLSQLLRESLAAEL-RGCGPRFGKHLLSYCPMPEKTFTTTPGGWLLES-GRPKEMVSTSNNKDG QALGTTSEFIPNL-SPELKKPLSEGQPSLKKIILSRKKRSGRHRFDPFCCEVICDDGTSVKLCT

SEQ ID NO: 14

>gi37183171AQ89389.1 INSL5 [Homo sapiens]

MKGSIFTLFLFSVLFAISEVRSKESVRLCGLEYIRT-VIYICASSRWRRHLEGIPQAQQAETGNSFQL-PHKREFSEENP AQNLPKVDASGEDRLWGGQMPT-EELWKSKKHSVMSRQDLQTLCCTDGCSMTDLSALC

SEQ ID NO: 15

>giH4768935gbAAD29686.1AF133816 1 insulin-like peptide INSL5 [Homo sapiens]

MKGSIFTLFLFSVLFAISEVRSKESVRLCGLEYIRT-VIYICASSRWRRHLEGIPQAQQAETGNSFQL-PHKREFSE ENPAQNLPKVDASGEDRLWGGQMPT-EELWKSKKHSVMSRQDLQTLCCTDGCSMTDLSALC

SEQ ID NO: 16

>gik5059419gbAAD39003.1AF156094 1 insulin-like protein 6 [Homo sapiens]

MPRLLRLSLLWLGLLLVRFSRELSDISSARKLCGRYL-VKEIEKLCGHANWSQFR-FEEETPFSRLIAQASEKVEAY SPYQFESPQTASPAR-GRGTNPVSTSWEEAVNSWEMQSLPEYKDKKGYSPLGKTREFSSSHNINVYIHENAFFQKKRRNKIKTLSNLFWGHHPQRKRRGYSEKCCLTGCTKEEL-SIACLPYIDFKRLKEKRSSLVTKIY

---

The invention claimed is:

1. A formulation comprising microparticles comprising an aliphatic polyester and an antifibrotic agent, wherein (i) said microparticles have a diameter of 1-100 µm; (ii) the antifibrotic agent is relaxin and is present in an amount that is 0.01-33% of total mass; (iii) said aliphatic polyester is of molecular weight 10,000-200,000 Daltons; or (iv) the microparticles further comprise a vinyl polymer.

2. The formulation of claim 1, wherein said antifibrotic agent is an agonist of the receptor RXFP1.

3. The formulation of claim 1, wherein said antifibrotic agent is human relaxin-2 or an analog or variant.

4. The formulation of claim 1, wherein the aliphatic polyester is poly-lactide-co-glycolide or polycaprolactone.

5. The formulation of claim 1, wherein said aliphatic polyester is terminated by an ester functional group, an alkyl-ester functional group or a carboxylic acid functional group.

6. The formulation of claim 1, wherein said formulation comprises a vinyl polymer that is poly(vinyl alcohol) or poly(pyrrolidone).

7. The formulation of claim 1, wherein said formulation comprises a vinyl polymer that is of molecular weight 10,000-200,000 Daltons.

8. The formulation of claim 1, wherein the diameter of said microparticles is 1-75 µm; or 1-50 µm; or 5-50 µm; or 25-50 µm; or 30-50 µm; or 40-50 µm.

9. The formulation of claim 1, wherein said aliphatic polyester is poly-lactide-co-glycolide with a molar ratio of 15:85-25:75, lactide:glycolide.

10. The formulation of claim 1, wherein the formulation comprises the vinyl polymer in an amount of 0.01-0.1% of total mass.

11. The formulation of claim 1, wherein said antifibrotic agent is 0.005-5% of the total formulation mass.

12. The formulation of claim 1, wherein said formulation comprises microparticles suspended in a sodium chloride liquid solution or a sodium carboxymethylcellulose solution.

13. The formulation of claim 1, wherein said formulation is a sustained release formulation.

14. The formulation of claim 1, wherein the formulation is formulated for administration via inhalation as an aerosol, administration via intra-articular injection or administration via intramuscular injection.

15. The formulation of claim 1, wherein the formulation is administered to the subject such that the antifibrotic agent is administered to a subject at a dose between 1-2000 µg/kg body weight.

16. The formulation of claim 1, wherein said formulation is a sustained release formulation wherein the antifibrotic agent is released over an extended period time selected from the group consisting of between 1-5 days; between 2-5 days; between 1-2 days; between 2-3 days; between 3-4 days; between 4-5 days; between 3-10 days; between 1-15 weeks; between 2-10 weeks; between 4-8 weeks; and between 8-15 weeks.

* * * * *

SEQUENCE LISTING

<160> NUMBER OF SEQ ID NOS: 16

<210> SEQ ID NO 1
<211> LENGTH: 185
<212> TYPE: PRT
<213> ORGANISM: Homo sapiens

<400> SEQUENCE: 1

```
Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 2
<211> LENGTH: 185
<212> TYPE: PRT
<213> ORGANISM: Homo sapiens

<400> SEQUENCE: 2

```
Met Pro Arg Leu Phe Phe Phe His Leu Leu Gly Val Cys Leu Leu Leu
1               5                   10                  15
```

```
Asn Gln Phe Ser Arg Ala Val Ala Asp Ser Trp Met Glu Glu Val Ile
             20                  25                  30

Lys Leu Cys Gly Arg Glu Leu Val Arg Ala Gln Ile Ala Ile Cys Gly
         35                  40                  45

Met Ser Thr Trp Ser Lys Arg Ser Leu Ser Gln Glu Asp Ala Pro Gln
     50                  55                  60

Thr Pro Arg Pro Val Ala Glu Ile Val Pro Ser Phe Ile Asn Lys Asp
 65                  70                  75                  80

Ile Glu Thr Ile Asn Met Met Ser Glu Phe Val Ala Asn Leu Pro Gln
                 85                  90                  95

Glu Leu Lys Leu Ile Leu Ser Glu Met Gln Pro Ala Leu Pro Gln Leu
             100                 105                 110

Gln Gln His Val Pro Val Leu Lys Asp Ser Ser Leu Leu Phe Glu Glu
         115                 120                 125

Phe Lys Lys Leu Ile Arg Asn Arg Gln Ser Glu Ala Ala Asp Ser Ser
     130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                 165                 170                 175

Thr Lys Arg Ser Leu Ala Arg Phe Cys
             180                 185

<210> SEQ ID NO 3
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Pro Arg Leu Phe Phe Phe His Leu Gly Val Cys Leu Leu Leu
 1               5                  10                  15

Asn Gln Phe Ser Arg Ala Val Ala Asp Ser Trp Met Glu Glu Val Ile
             20                  25                  30

Lys Leu Cys Gly Arg Glu Leu Val Arg Ala Gln Ile Ala Ile Cys Gly
         35                  40                  45

Met Ser Thr Trp Ser Lys Arg Ser Leu Ser Gln Glu Asp Ala Pro Gln
     50                  55                  60

Thr Pro Arg Pro Val Ala Glu Ile Val Pro Ser Phe Ile Asn Lys Asp
 65                  70                  75                  80

Ile Glu Thr Ile Asn Met Met Ser Glu Phe Val Ala Asn Leu Pro Gln
                 85                  90                  95

Glu Leu Lys Leu Ile Leu Ser Glu Met Gln Pro Ala Leu Pro Gln Leu
             100                 105                 110

Gln Gln His Val Pro Val Leu Lys Asp Ser Ser Leu Leu Phe Glu Glu
         115                 120                 125

Phe Lys Lys Leu Ile Arg Asn Arg Gln Ser Glu Ala Ala Asp Ser Ser
     130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                 165                 170                 175

Thr Lys Arg Ser Leu Ala Arg Phe Cys
             180                 185
```

<210> SEQ ID NO 4
<211> LENGTH: 185
<212> TYPE: PRT
<213> ORGANISM: Homo sapiens

<400> SEQUENCE: 4

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Ile Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 5
<211> LENGTH: 185
<212> TYPE: PRT
<213> ORGANISM: Homo sapiens

<400> SEQUENCE: 5

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Ile Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
        180                 185

<210> SEQ ID NO 6
<211> LENGTH: 92
<212> TYPE: PRT
<213> ORGANISM: Homo sapiens

<400> SEQUENCE: 6

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
                20                  25                  30

Lys Leu Cys Gly Arg Glu Leu Val Arg Ala Gln Ile Ala Ile Cys Gly
            35                  40                  45

Met Ser Thr Trp Ser Lys Arg Ser Leu Ser Gln Glu Asp Ala Pro Gln
50                  55                  60

Thr Pro Arg Pro Val Ala Gly Ile Ser Ser Leu Leu Arg Arg Arg
65                  70                  75                  80

Leu Phe Glu Asp His Asp Gly Pro Ser Phe Leu Val
                85                  90

<210> SEQ ID NO 7
<211> LENGTH: 99
<212> TYPE: PRT
<213> ORGANISM: Homo sapiens

<400> SEQUENCE: 7

Met Leu Glu Phe Ile Ala Asn Leu Pro Pro Glu Leu Lys Ala Ala Leu
1               5                   10                  15

Ser Glu Arg Gln Pro Ser Leu Pro Glu Leu Gln Gln Tyr Val Pro Ala
                20                  25                  30

Leu Lys Asp Ser Asn Leu Ser Phe Glu Glu Phe Lys Lys Leu Ile Arg
            35                  40                  45

Asn Arg Gln Ser Glu Ala Ala Asp Ser Asn Pro Ser Glu Leu Lys Tyr
50                  55                  60

Leu Gly Leu Asp Thr His Ser Gln Lys Lys Arg Arg Pro Tyr Val Ala
65                  70                  75                  80

Leu Phe Glu Lys Cys Cys Leu Ile Gly Cys Thr Lys Arg Ser Leu Ala
                85                  90                  95

Lys Tyr Cys

<210> SEQ ID NO 8
<211> LENGTH: 142
<212> TYPE: PRT
<213> ORGANISM: Homo sapiens

<400> SEQUENCE: 8

Met Ala Arg Tyr Met Leu Leu Leu Leu Ala Val Trp Val Leu Thr
1               5                   10                  15

Gly Glu Leu Trp Pro Gly Ala Glu Ala Arg Ala Ala Pro Tyr Gly Val
                20                  25                  30

Arg Leu Cys Gly Arg Glu Phe Ile Arg Ala Val Ile Phe Thr Cys Gly

```
            35                  40                  45
Gly Ser Arg Trp Arg Arg Ser Asp Ile Leu Ala His Glu Ala Met Gly
    50                  55                  60
Asp Thr Phe Pro Asp Ala Asp Ala Asp Glu Asp Ser Leu Ala Gly Glu
65                  70                  75                  80
Leu Asp Glu Ala Met Gly Ser Ser Glu Trp Leu Ala Leu Thr Lys Ser
                85                  90                  95
Pro Gln Ala Phe Tyr Arg Gly Arg Pro Ser Trp Gln Gly Thr Pro Gly
                100                 105                 110
Val Leu Arg Gly Ser Arg Asp Val Leu Ala Gly Leu Ser Ser Ser Cys
            115                 120                 125
Cys Lys Trp Gly Cys Ser Lys Ser Glu Ile Ser Ser Leu Cys
        130                 135                 140

<210> SEQ ID NO 9
<211> LENGTH: 142
<212> TYPE: PRT
<213> ORGANISM: Homo sapiens

<400> SEQUENCE: 9

Met Ala Arg Tyr Met Leu Leu Leu Leu Ala Val Trp Val Leu Thr
1               5                   10                  15
Gly Glu Leu Trp Pro Gly Ala Glu Ala Arg Ala Ala Pro Tyr Gly Val
                20                  25                  30
Arg Leu Cys Gly Arg Glu Phe Ile Arg Ala Val Ile Phe Thr Cys Gly
            35                  40                  45
Gly Ser Arg Trp Arg Arg Ser Asp Ile Leu Ala His Glu Ala Met Gly
    50                  55                  60
Asp Thr Phe Pro Asp Ala Asp Ala Asp Glu Asp Ser Leu Ala Gly Glu
65                  70                  75                  80
Leu Asp Glu Ala Met Gly Ser Ser Glu Trp Leu Ala Leu Thr Lys Ser
                85                  90                  95
Pro Gln Ala Phe Tyr Arg Gly Arg Pro Ser Trp Gln Gly Thr Pro Val
                100                 105                 110
Val Leu Arg Gly Ser Arg Asp Val Leu Ala Gly Leu Ser Ser Ser Cys
            115                 120                 125
Cys Lys Trp Gly Cys Ser Lys Ser Glu Ile Ser Ser Leu Cys
        130                 135                 140

<210> SEQ ID NO 10
<211> LENGTH: 142
<212> TYPE: PRT
<213> ORGANISM: Homo sapiens

<400> SEQUENCE: 10

Met Ala Arg Tyr Met Leu Leu Leu Leu Ala Val Trp Val Leu Thr
1               5                   10                  15
Gly Glu Leu Trp Pro Gly Ala Glu Ala Arg Ala Ala Pro Tyr Gly Val
                20                  25                  30
Arg Leu Cys Gly Arg Glu Phe Ile Arg Ala Val Ile Phe Thr Cys Gly
            35                  40                  45
Gly Ser Arg Trp Arg Arg Ser Asp Ile Leu Ala His Glu Ala Met Gly
    50                  55                  60
Asp Thr Phe Pro Asp Ala Asp Ala Asp Glu Asp Ser Leu Ala Gly Glu
65                  70                  75                  80
Leu Asp Glu Ala Met Gly Ser Ser Glu Trp Leu Ala Leu Thr Lys Ser
```

```
                     85                  90                  95

Pro Gln Ala Phe Tyr Arg Gly Arg Pro Ser Trp Gln Gly Thr Pro Gly
                100                 105                 110

Val Leu Arg Gly Ser Arg Asp Val Leu Ala Gly Leu Ser Ser Ser Cys
                115                 120                 125

Cys Lys Trp Gly Cys Ser Lys Ser Glu Ile Ser Ser Leu Cys
            130                 135                 140

<210> SEQ ID NO 11
<211> LENGTH: 131
<212> TYPE: PRT
<213> ORGANISM: Homo sapiens

<400> SEQUENCE: 11

Met Asp Pro Arg Leu Pro Ala Trp Ala Leu Val Leu Leu Gly Pro Ala
1               5                   10                  15

Leu Val Phe Ala Leu Gly Pro Ala Pro Thr Pro Glu Met Arg Glu Lys
                20                  25                  30

Leu Cys Gly His His Glu Val Arg Ala Leu Val Arg Val Cys Gly Gly
            35                  40                  45

Pro Arg Trp Ser Thr Glu Ala Arg Arg Pro Ala Thr Gly Gly Asp Arg
        50                  55                  60

Glu Leu Leu Gln Trp Leu Glu Arg Arg His Leu Leu His Gly Leu Val
65                  70                  75                  80

Ala Asp Ser Asn Leu Thr Leu Gly Pro Gly Leu Gln Pro Leu Pro Gln
                85                  90                  95

Thr Ser His His His Arg His His Arg Ala Ala Ala Thr Asn Pro Ala
                100                 105                 110

Arg Tyr Cys Cys Leu Ser Gly Cys Thr Gln Gln Asp Leu Leu Thr Leu
            115                 120                 125

Cys Pro Tyr
        130

<210> SEQ ID NO 12
<211> LENGTH: 139
<212> TYPE: PRT
<213> ORGANISM: Homo sapiens

<400> SEQUENCE: 12

Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
                20                  25                  30

Pro Arg Phe Gly Lys His Leu Leu Ser Tyr Cys Pro Met Pro Glu Lys
            35                  40                  45

Thr Phe Thr Thr Thr Pro Gly Gly Trp Leu Leu Glu Ser Gly Arg Pro
        50                  55                  60

Lys Glu Met Val Ser Thr Ser Asn Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
                100                 105                 110

Lys Arg Ser Gly Arg His Arg Phe Asp Pro Phe Cys Cys Glu Val Ile
            115                 120                 125

Cys Asp Asp Gly Thr Ser Val Lys Leu Cys Thr
```

```
              130                 135

<210> SEQ ID NO 13
<211> LENGTH: 139
<212> TYPE: PRT
<213> ORGANISM: Homo sapiens

<400> SEQUENCE: 13

Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
            20                  25                  30

Pro Arg Phe Gly Lys His Leu Leu Ser Tyr Cys Pro Met Pro Glu Lys
        35                  40                  45

Thr Phe Thr Thr Thr Pro Gly Gly Trp Leu Leu Glu Ser Gly Arg Pro
    50                  55                  60

Lys Glu Met Val Ser Thr Ser Asn Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
        115                 120                 125

Cys Asp Asp Gly Thr Ser Val Lys Leu Cys Thr
    130                 135

<210> SEQ ID NO 14
<211> LENGTH: 135
<212> TYPE: PRT
<213> ORGANISM: Homo sapiens

<400> SEQUENCE: 14

Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
        35                  40                  45

His Leu Glu Gly Ile Pro Gln Ala Gln Gln Ala Glu Thr Gly Asn Ser
    50                  55                  60

Phe Gln Leu Pro His Lys Arg Glu Phe Ser Glu Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
        115                 120                 125

Thr Asp Leu Ser Ala Leu Cys
    130                 135

<210> SEQ ID NO 15
<211> LENGTH: 135
<212> TYPE: PRT
<213> ORGANISM: Homo sapiens

<400> SEQUENCE: 15
```

```
Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
            35                  40                  45

His Leu Glu Gly Ile Pro Gln Ala Gln Gln Ala Glu Thr Gly Asn Ser
        50                  55                  60

Phe Gln Leu Pro His Lys Arg Glu Phe Ser Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
            115                 120                 125

Thr Asp Leu Ser Ala Leu Cys
            130             135

<210> SEQ ID NO 16
<211> LENGTH: 213
<212> TYPE: PRT
<213> ORGANISM: Homo sapiens

<400> SEQUENCE: 16

Met Pro Arg Leu Leu Arg Leu Ser Leu Leu Trp Leu Gly Leu Leu Leu
1               5                   10                  15

Val Arg Phe Ser Arg Glu Leu Ser Asp Ile Ser Ser Ala Arg Lys Leu
            20                  25                  30

Cys Gly Arg Tyr Leu Val Lys Glu Ile Glu Lys Leu Cys Gly His Ala
            35                  40                  45

Asn Trp Ser Gln Phe Arg Phe Glu Glu Glu Thr Pro Phe Ser Arg Leu
        50                  55                  60

Ile Ala Gln Ala Ser Glu Lys Val Glu Ala Tyr Ser Pro Tyr Gln Phe
65                  70                  75                  80

Glu Ser Pro Gln Thr Ala Ser Pro Ala Arg Gly Arg Gly Thr Asn Pro
                85                  90                  95

Val Ser Thr Ser Trp Glu Glu Ala Val Asn Ser Trp Glu Met Gln Ser
            100                 105                 110

Leu Pro Glu Tyr Lys Asp Lys Lys Gly Tyr Ser Pro Leu Gly Lys Thr
            115                 120                 125

Arg Glu Phe Ser Ser Ser His Asn Ile Asn Val Tyr Ile His Glu Asn
            130                 135                 140

Ala Phe Phe Gln Lys Lys Arg Arg Asn Lys Ile Lys Thr Leu Ser Asn
145                 150                 155                 160

Leu Phe Trp Gly His His Pro Gln Arg Lys Arg Gly Tyr Ser Glu
                165                 170                 175

Lys Cys Cys Leu Thr Gly Cys Thr Lys Glu Glu Leu Ser Ile Ala Cys
            180                 185                 190

Leu Pro Tyr Ile Asp Phe Lys Arg Leu Lys Glu Lys Arg Ser Ser Leu
            195                 200                 205

Val Thr Lys Ile Tyr
            210
```